(12) United States Patent
Dehury et al.

(10) Patent No.: US 10,364,269 B2
(45) Date of Patent: Jul. 30, 2019

(54) PROCESSES FOR THE PREPARATION OF CARFILZOMIB OR PHARMACEUTICALLY ACCEPTABLE SALTS THEREOF

(71) Applicant: LAURUS LABS PRIVATE LIMITED, Hyderabad (IN)

(72) Inventors: Sanjay Kumar Dehury, Hyderabad (IN); Nagaraju Mekala, Hyderabad (IN); Jahangeer Baba Shaik, Hyderabad (IN); Srinivasa Rao Buddepu, Hyderabad (IN); Lakshmi Kanth Kola, Hyderabad (IN); Venkata Sunil Kumar Indukuri, Hyderabad (IN); Seeta Rama Anjaneyulu Gorantla, Hyderabad (IN); Satyanarayana Chava, Hyderabad (IN)

(73) Assignee: LAURUS LABS LIMITED, Hyderabad (IN)

( * ) Notice: Subject to any disclaimer, the term of this patent is extended or adjusted under 35 U.S.C. 154(b) by 60 days.

(21) Appl. No.: 15/573,912

(22) PCT Filed: May 21, 2016

(86) PCT No.: PCT/IB2016/052994
§ 371 (c)(1),
(2) Date: Nov. 14, 2017

(87) PCT Pub. No.: WO2016/185450
PCT Pub. Date: Nov. 24, 2016

(65) Prior Publication Data
US 2019/0085026 A1 Mar. 21, 2019

(30) Foreign Application Priority Data

May 21, 2015 (IN) ............. 2543/CHE/2015
May 25, 2015 (IN) ............. 2592/CHE/2015
Jun. 22, 2015 (IN) ............. 3106/CHE/2015

(51) Int. Cl.
| | | |
|---|---|---|
| C07K 5/103 | (2006.01) |
| A61K 47/42 | (2017.01) |
| C07C 271/22 | (2006.01) |
| C07D 303/36 | (2006.01) |
| C07C 271/16 | (2006.01) |
| C07C 271/18 | (2006.01) |
| A61K 9/00 | (2006.01) |
| A61K 38/07 | (2006.01) |

(52) U.S. Cl.
CPC ............ *C07K 5/1008* (2013.01); *A61K 47/42* (2013.01); *C07C 271/16* (2013.01); *C07C 271/18* (2013.01); *C07C 271/22* (2013.01); *C07D 303/36* (2013.01); *A61K 9/0019* (2013.01); *A61K 38/07* (2013.01)

(58) Field of Classification Search
CPC .............. A61K 31/444; A61K 31/7048; A61K 31/706; A61K 31/336; A61K 38/005; A61P 35/00; C07D 519/00; C12N 15/1137
See application file for complete search history.

(56) References Cited

U.S. PATENT DOCUMENTS

| | | | |
|---|---|---|---|
| 7,232,818 B2 | 6/2007 | Smyth et al. |
| 8,367,617 B2 | 2/2013 | Phiasivongsa et al. |
| 2005/0245435 A1 | 11/2005 | Smyth et al. |
| 2009/0105156 A1 | 4/2009 | Phiasivongsa et al. |

FOREIGN PATENT DOCUMENTS

| | | |
|---|---|---|
| CN | 103641890 A | 3/2014 |
| CN | 103804469 A | 5/2014 |
| CN | 103864889 A | 6/2014 |
| CN | 103864898 A | 6/2014 |
| CN | 103936282 A | 7/2014 |
| CN | 104086624 A | 10/2014 |
| CN | 104230857 | 12/2014 |
| CN | 104356197 A | 2/2015 |
| CN | 104557793 A | 4/2015 |
| CN | 104672179 A | 6/2015 |
| CN | 104672180 A | 6/2015 |
| CN | 104710507 A | 6/2015 |
| CN | 105017181 A | 11/2015 |
| CN | 105218488 A | 1/2016 |
| CN | 105273057 A | 1/2016 |
| CN | 105294501 A | 2/2016 |
| CN | 105440106 A | 3/2016 |
| WO | WO-2005/111009 A2 | 11/2005 |
| WO | WO-2009/045497 A1 | 4/2009 |
| WO | WO-2014/003203 A2 | 1/2014 |
| WO | WO-2015/0032621 A1 | 3/2015 |
| WO | WO-2015/0032622 A1 | 3/2015 |
| WO | WO-2016046843 A1 | 3/2016 |
| WO | WO-2016/069479 A1 | 5/2016 |

OTHER PUBLICATIONS

The International Search Report for PCT/IB2016/052994 dated Sep. 16, 2016.
Sin et al. "Total Synthese of the Potent Proteasome Inhibitor Epoxomicin: A Useful Tool for Understanding Proteasome Biology", Bioort. Med. Chem, Lett. 9 (1999) 2283-2288.
Pereira, et al. The Carmaphyscins: New Proteasome Inhibitors Exhibiting an α,β-Epoxyketone Warhead from a Marine Cyanobacterium, Chembiochem, Weinheim, V. 13, n. 6, p. 810-817, Apr. 2012.
Screen, et al. Nature of Pharmacophore Influences Active Site Specificity of Proteasome Inhibitors, Journal of Biological Chemistry, Dec. 17, 2010, vol. 285, No. 51, p. 40125-40134.
Wang, et al. "Manganese Catalysts with C1-Symmetrice N4 Ligand for Enantioselective Epoxidation of Olefins", chem. Eur. J. 2012, 18, 6750-6573.

Primary Examiner — Marcela M Cordero Garcia
Assistant Examiner — Jia-Hai Lee
(74) Attorney, Agent, or Firm — Blank Rome LLP

(57) ABSTRACT

The present invention relates to an improved process for the preparation of carfilzomib or a pharmaceutically acceptable salt thereof. The present invention also relates to a process for the preparation of amorphous form of carfilzomib.

31 Claims, 10 Drawing Sheets

PROCESSES FOR THE PREPARATION OF CARFILZOMIB OR PHARMACEUTICALLY ACCEPTABLE SALTS THEREOF

CROSS-REFERENCE TO RELATED APPLICATIONS

This application is a national phase application of and claims the benefit of International Application PCT/IB2016/052994, filed on 21 May 2016, which is based on and claims the benefit of Indian Provisional Application No. 2543/CHE/2015, filed on 21 May 2015 entitled "An improved process for the preparation of carfilzomib or pharmaceutically acceptable salts thereof", and claims the benefit of Indian Provisional Application No. 2592/CHE/2015, filed on 25 May 2015 entitled "An improved process for preparation of tert-butyl ((2S)-4-methyl-1-((2R)-2-methyloxirane-2-yl)-1-oxo-pentan-2-yl) carbamate", and claims the benefit of Indian Provisional Application No. 3106/CHE/2015, filed on 22 Jun. 2015 entitled "An improved process for the preparation of carfilzomib or pharmaceutically acceptable salts thereof", the contents of each of which are incorporated by reference herein.

FIELD OF THE INVENTION

The present invention generally relates to an improved process for the preparation of carfilzomib or a pharmaceutically acceptable salt thereof. The present invention also relates to process for preparation of amorphous form of carfilzomib.

The present invention further relates to a process for preparation of tert-butyl ((2S)-4-methyl-1-((2R)-2-methyl-oxirane-2-yl)-1-oxo-pentan-2-yl)-carbamate, a synthetic intermediate for preparation of carfilzomib.

BACKGROUND OF THE INVENTION

Carfilzomib is a tetrapeptide epoxyketone, also known as (2S)—N—((S)-1-((S)-4-methyl-1-((R)-2-methyloxiran2-yl)-1-oxopentan-2-yl-carbamoyl)-2-phenyl-ethyl)-2-((S)-2-(2-morpholinoacetamido)-4-phenylbutanamido)-4-methyl-pentanamide, is represented by the following structure of Formula I:

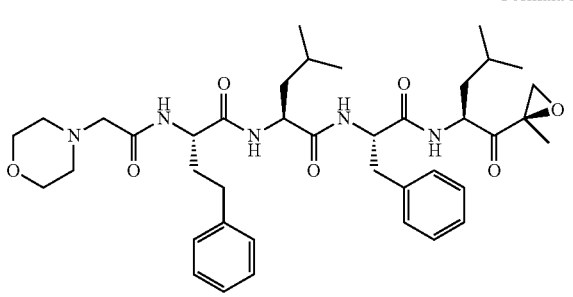

Formula I

Carfilzomib is marketed by Onyx Pharma under the trade name Kyprolis® is indicated for the treatment of patients with multiple myeloma who have received at least two prior therapies including bortezomib and an immunomodulatory agent and have demonstrated disease progression on or within 60 days of completion of the last therapy.

U.S. Pat. No. 7,232,818 ("the '818 patent") discloses a variety of peptide based compounds and their derivatives such as carfilzomib and its process for preparation thereof. The process disclosed in the '818 patent is schematically represented as follows:

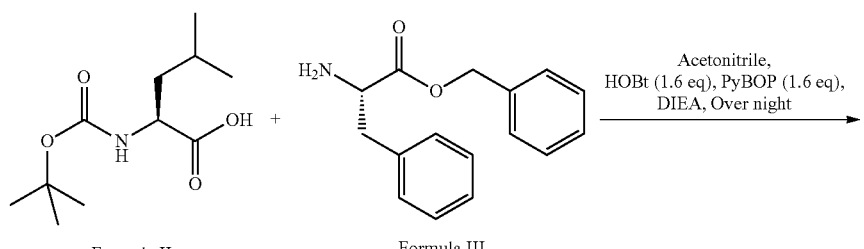

Formula II    Formula III

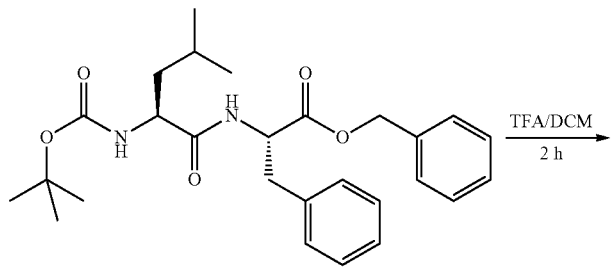

Formula IV

-continued
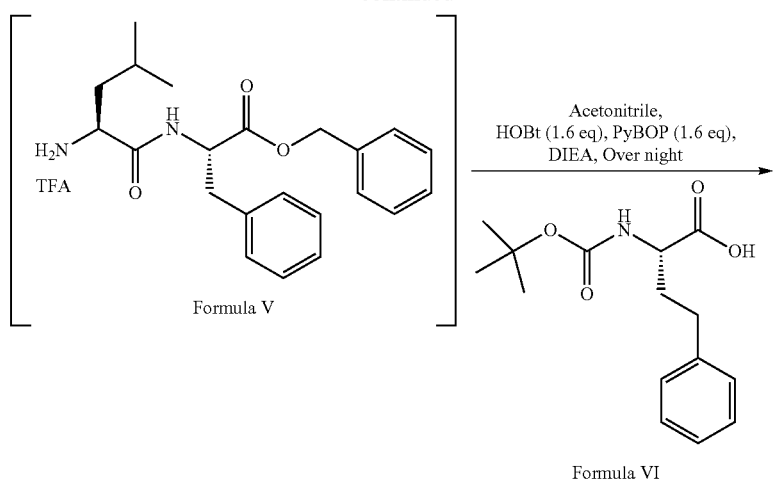
Formula V
Formula VI
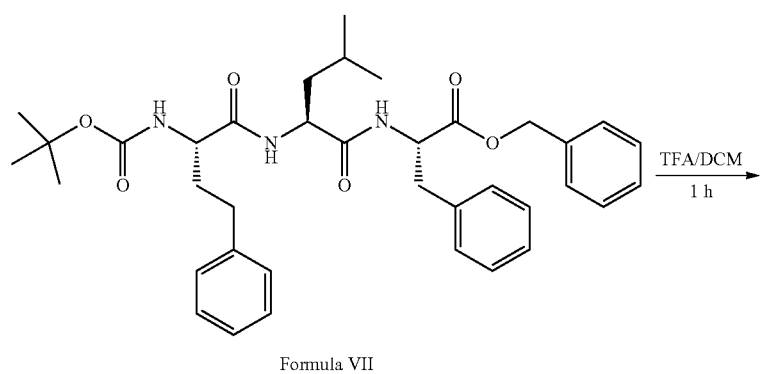
Formula VII
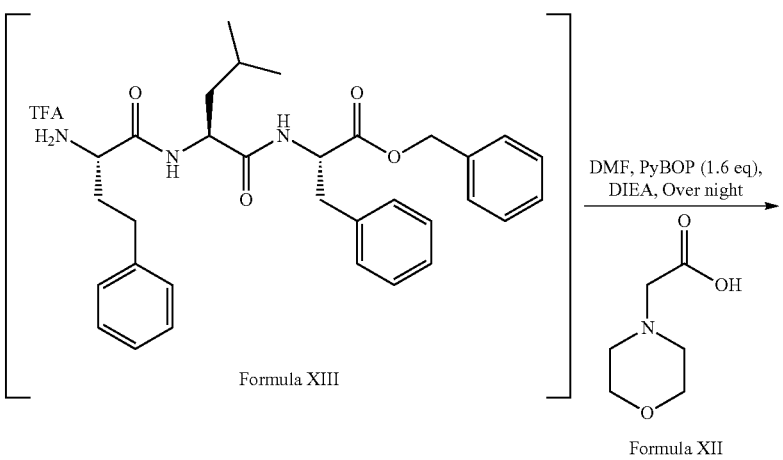
Formula XIII
Formula XII
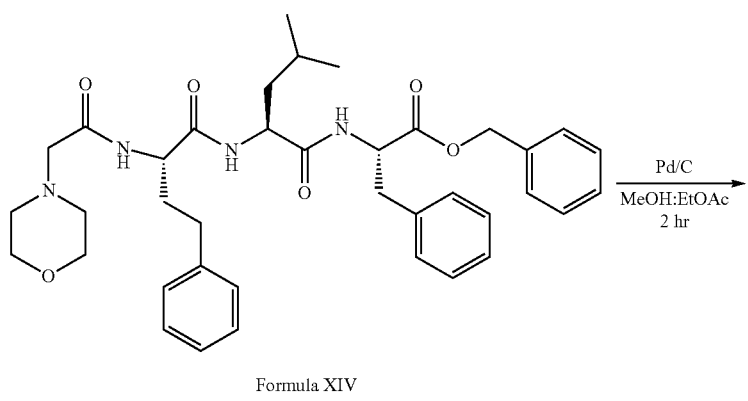
Formula XIV

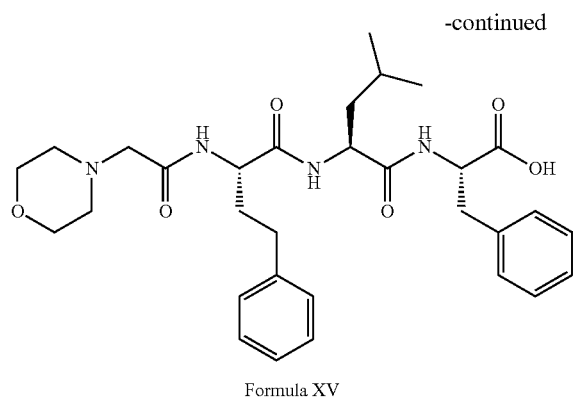

Formula XV

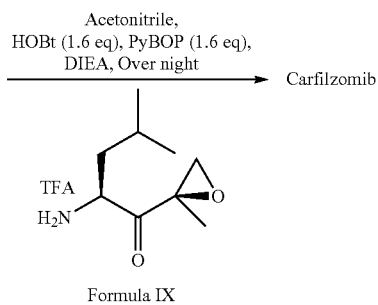

Formula IX

The synthesis of carfilzomib as disclosed in the '818 patent has certain drawbacks as it involves:
a) coupling of N-boc-leucine of Formula II with phenyl alanine benzyl ester of Formula III in presence of excess quantity of coupling agents such as PyBOP of about 1.6 w/w mole equivalents and an additive of HOBt of about 1.6 w/w mole equivalents per mole of Formula III, in higher volume of solvent such as acetonitrile of about 45 v for the preparation of compound of Formula IV;
b) coupling of trifluoro acetic acid salt of Formula V with a compound of Formula VI in presence of excess quantity of coupling agents such as PyBOP of about 1.6 w/w mole equivalents and an additive of HOBt of about 1.6 w/w mole equivalents per mole of Formula IV, in higher volume of solvent such as acetonitrile of about 22 v for the preparation of compound of Formula VII;
c) coupling of trifluoro acetic acid salt of Formula XIII with morpholine acetic acid of Formula XII in presence of excess quantity of coupling agents such as PyBOP of about 1.6 w/w mole equivalents and an additive of HOBt of about 1.6 w/w mole equivalents per mole of Formula VII, in higher volume of solvent such as dimethylformamide of about 24 v for the preparation of compound of Formula XIV; and
d) coupling of Formula XV with a compound of Formula IX in presence of excess quantity of coupling agents such as PyBOP of about 1.6 w/w mole equivalents per mole of Formula XV, in higher volume of solvent such as acetonitrile of about 50 v for the preparation of carfilzomib;

All the above mentioned amide coupling reactions involves use of excess quantity of coupling agent, excess quantity of an additive and solvent. Use of excess quantity of these reagents results to formation of higher quantity of unreacted HOBt, PyBOP and by product of tris(pyrrolidino phosphine) oxide thereby it necessitates separate purification techniques required for the high pure product, which contributes significant impact on the final yield and purity, thereby process not viable for large scale manufacturing. Further, the process involves long reaction times, which leads to an increase in the manufacturing cycle time and decrease in the product yield and quality.

Further, the '818 patent involves solvent extractions for isolation of intermediates and final product; which process also isolates unreacted coupling agents present in the reaction medium along with required intermediates and final product. Thereby additional purifications required to separate those unwanted coupling agents.

*Journal of biological chemistry* vol. 285, no. 51, pp. 40125-40134, 2010 discloses preparation of carfilzomib. The process disclosed in the article is schematically represented as follows:

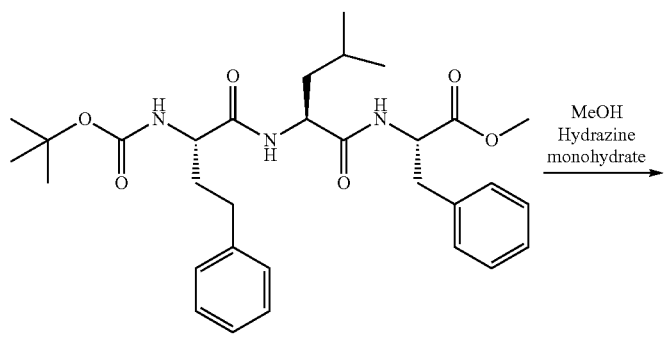

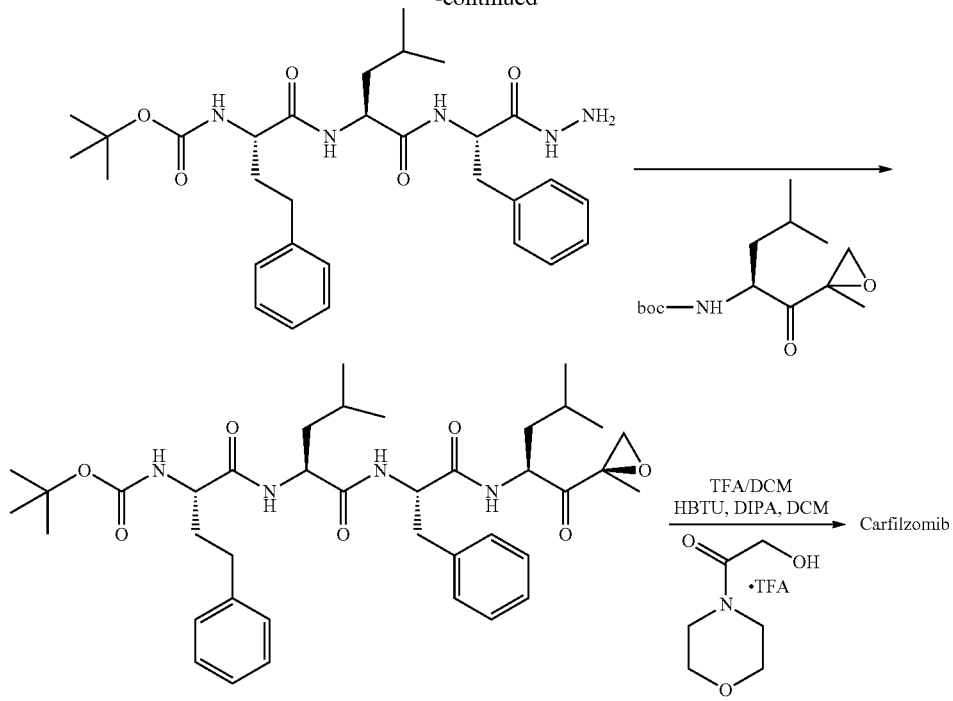
U.S. Pat. No. 8,367,617 ("the '617 patent") disclosed an alternate process for preparation of carfilzomib. The process disclosed in the '617 patent is schematically represented as follows:
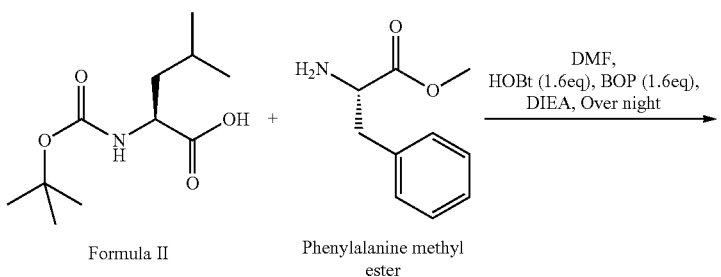
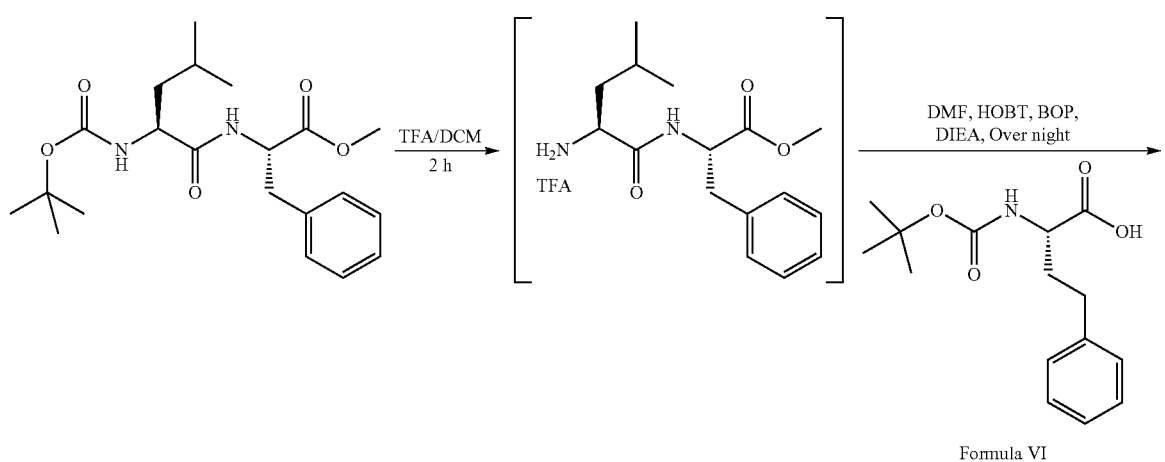

-continued
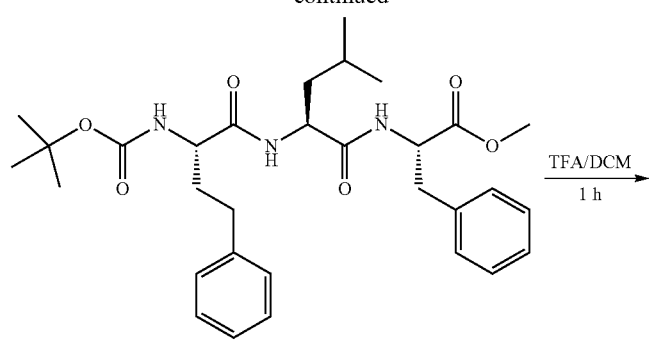
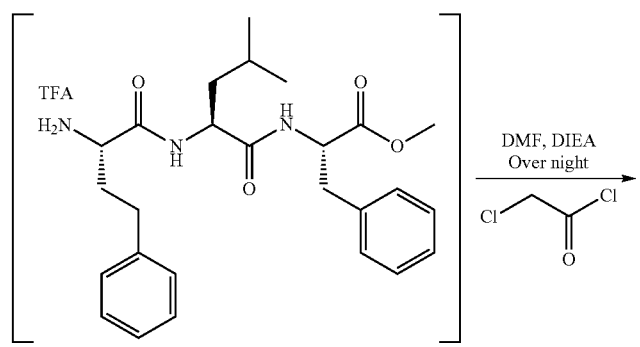
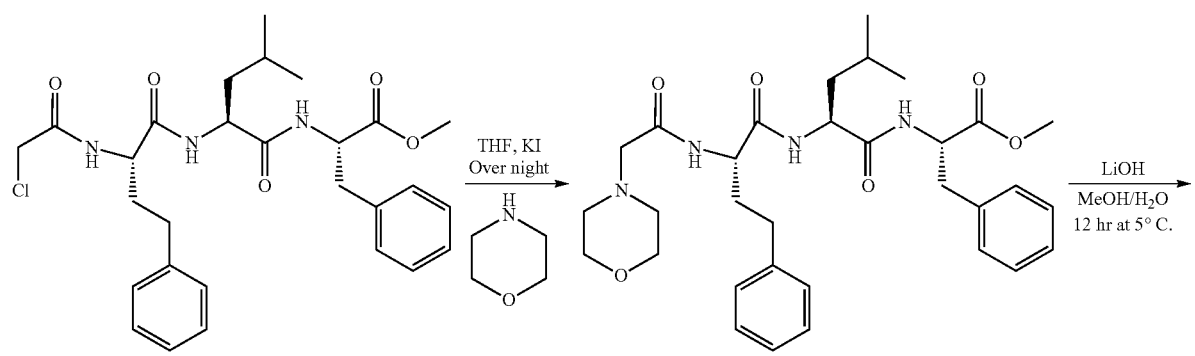
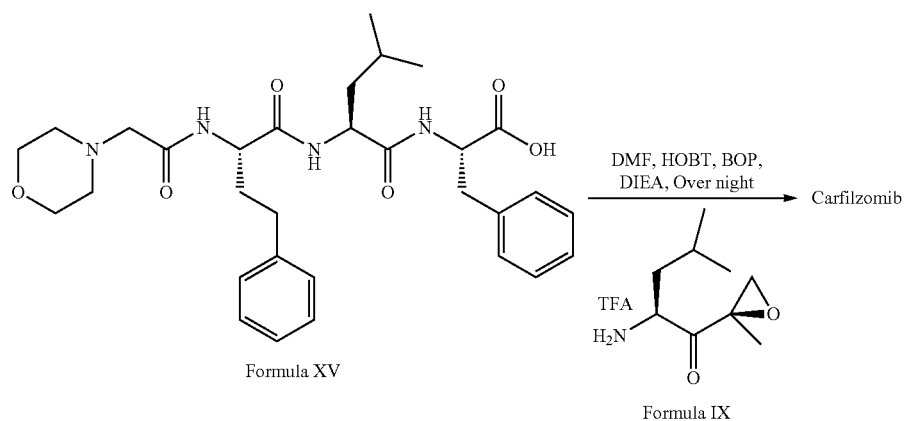 [SMILES: CC(C)C[C@H](NC(=O)[C@H](CCc1ccccc1)NC(=O)CN1CCOCC1)C(=O)N[C@@H](Cc1ccccc1)C(=O)O ; CC(C)C[C@H](N)C(=O)[C@@]1(C)CO1]

However, '617 patent disclosed process also involves use of excess quantity of coupling agents same as mentioned for '818 patent.

PCT publication No. 2015/010436 ("the '436 publication") discloses a process for preparation of carfilzomib. The process disclosed in the '436 publication is schematically represented as follows:

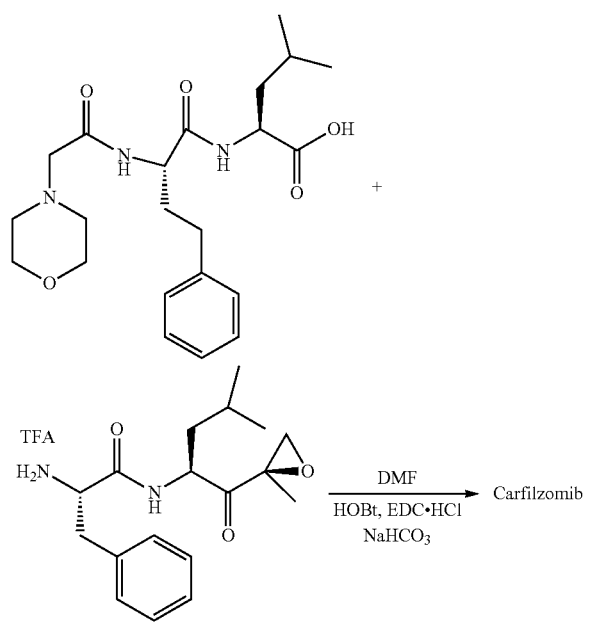

PCT publication No. 2015/032621 ("the '621 publication") discloses a process for preparation of carfilzomib. The process disclosed in the '621 publication is schematically represented as follows:

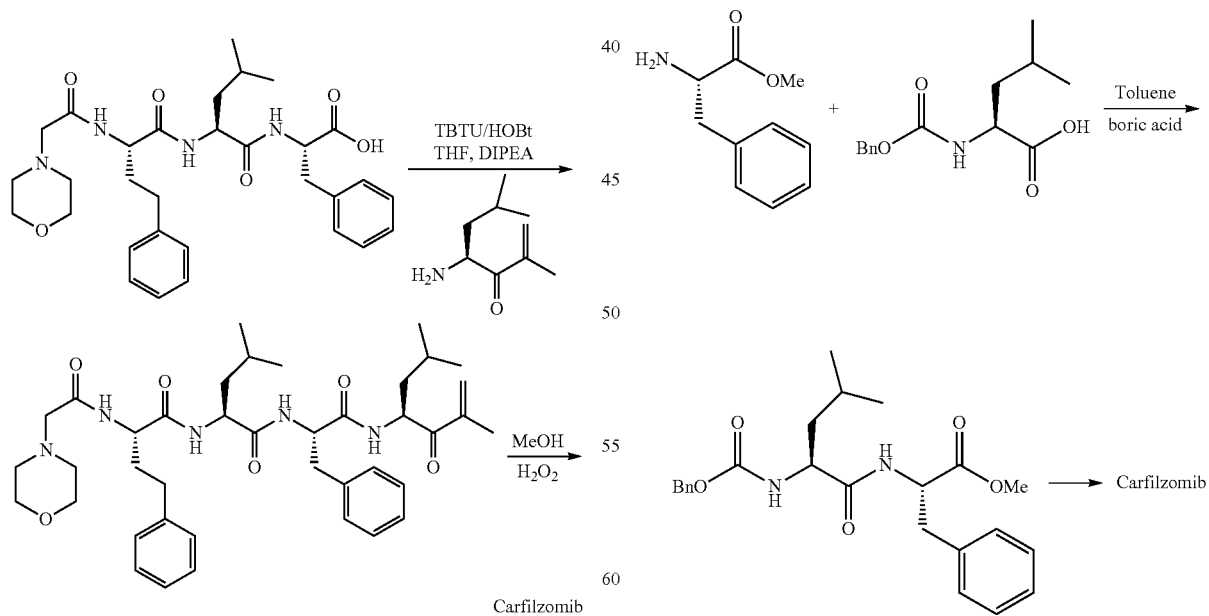

PCT publication No. 2015/032622 ("the '622 publication") discloses a process for preparation of carfilzomib. The process disclosed in the '622 publication is schematically represented as follows:

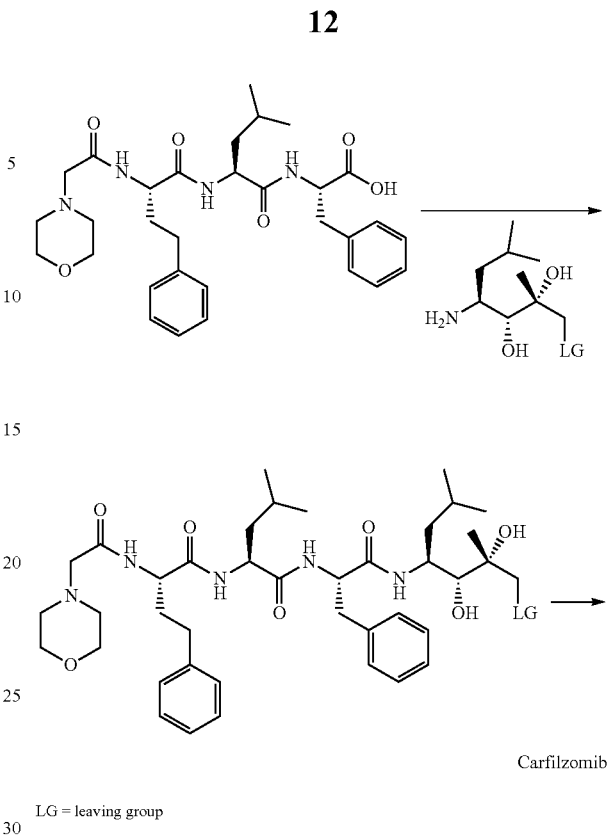

LG = leaving group

PCT publication No. 2015/121769 ("the '769 publication") discloses a process for preparation of carfilzomib intermediate. The process disclosed in the '769 publication is schematically represented as follows:

PCT publication No. 2016/046843 ("the '843 publication") discloses a process for preparation of carfilzomib. The process disclosed in the '843 publication is schematically represented as follows:

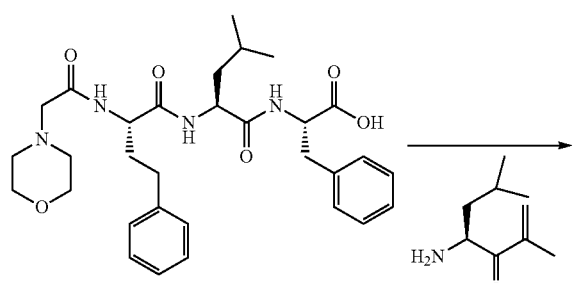

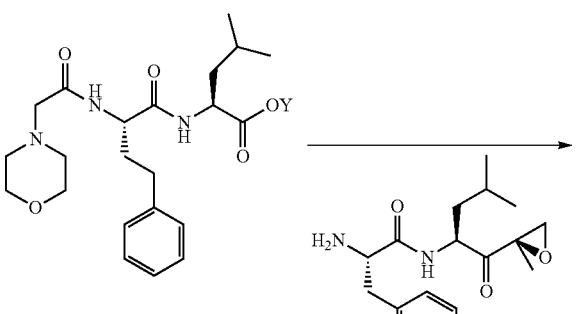

Carfilzomib

Y = pentafluorophenyl, trichlorophenyl, benzotriazole, azabenzotriazole, nitrophenyl, pentachlorophenyl & fluorenylmethyl Kyung et al., in *Bioorganic & Medicinal Chemistry Letters* 9 (1999) 2283-2288 discloses a process for the preparation of carfilzomib intermediate of Formula XVI starting from Weinrebamide of Formula XVII, which involves direct epoxidation of α,β-unsaturated ketone of Formula XVIII in presence of hydrogen peroxide to obtain diastereomeric mixture in compound of Formula XVI and Formula XVIa in a ratio of 1.7:1. However, this reference silent on isolation of intermediate compounds obtained from this process. The process disclosed by Kyung et al is schematically represented as follows:

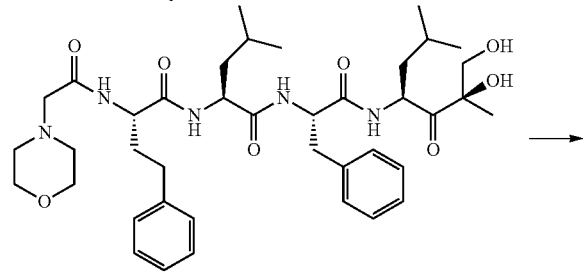

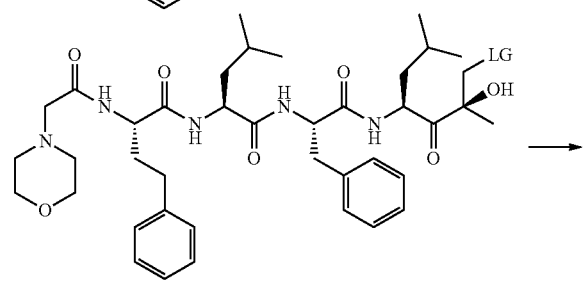

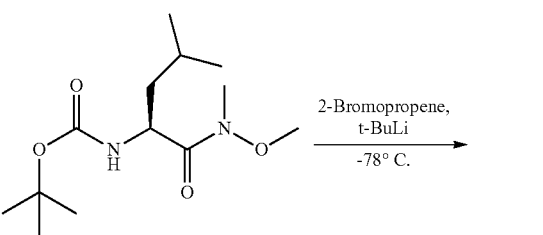

Formula XVII

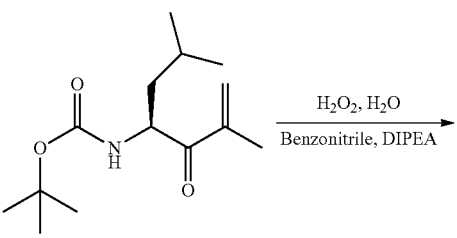

Formula XVIII

Carfilzomib

LG = leaving group

PCT publication No. 2016/069479 ("the '479 publication") discloses a process for preparation of carfilzomib. The process disclosed in the '479 publication is schematically represented as follows:

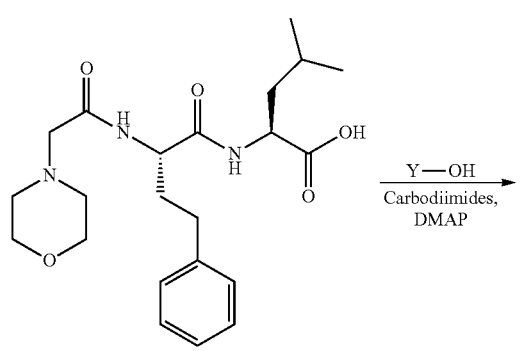

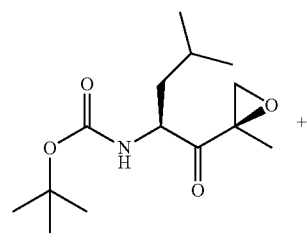

Formula XVI

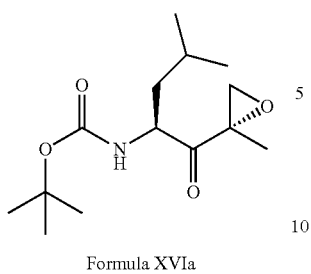

Formula XVIa

PCT publication No. 2005/111009 ("the '009 publication") discloses a process for preparation of carboxybenzyl (Cbz) protected compound of Formula XVI, by reduction of Cbz protected α,β-unsaturated ketone of Formula XVIII there by forming a diastereomeric mixture of allyl alcohol of Formula XIXa and Formula XIXb and epoxidation of allyl group of the obtained diastereomeric mixture of Formula XIX to obtain a diastereomeric mixture of compound of Formula XXa and Formula XXb, further oxidizing the hydroxy group of the obtained a diastereomeric mixture of Formula XX and the obtained compound was purified by flash chromatography to obtain diastereomeric mixture of compound of Formula XVI and Formula XVIa as a light yellow oil in a ratio of 9:1. The process disclosed in the '009 publication is schematically represented as follows:

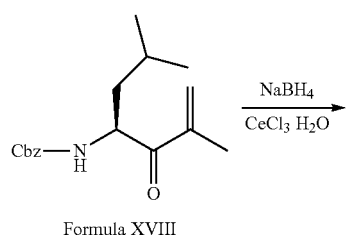

Formula XVIII

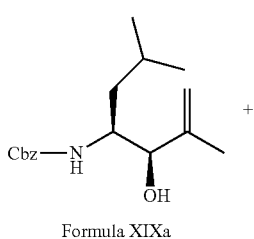

Formula XIXa

+

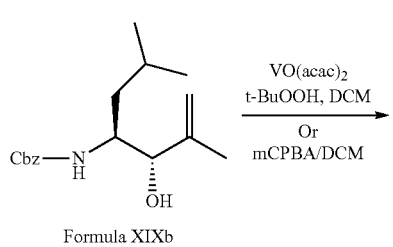

Formula XIXb

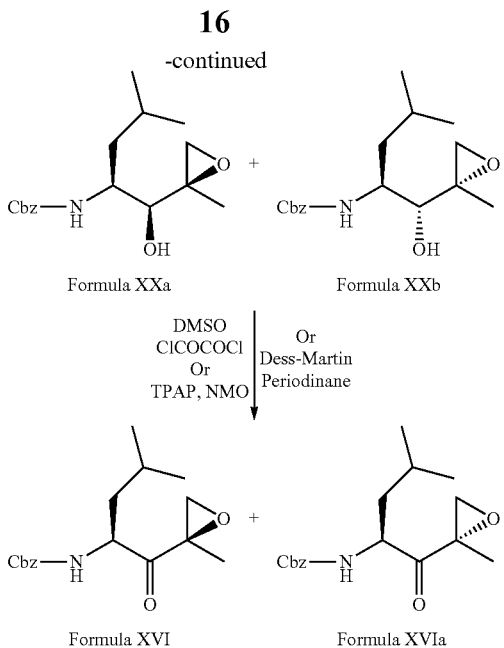

Formula XXa  Formula XXb

Formula XVI  Formula XVIa

PCT publication No. 2009/045497 ("the '497 publication") discloses a process for stereoselective epoxidation of α,β-unsaturated ketone of Formula XVIII in presence of sodium hypochlorite or calcium hypochlorite to obtain diastereomeric mixture of compound of Formula XVI and Formula XVIa. The process disclosed in the '497 publication is schematically represented as follows:

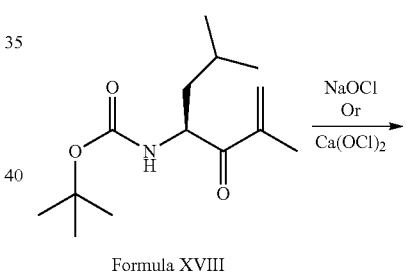

Formula XVIII

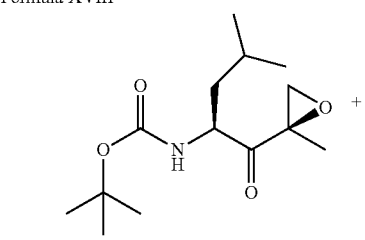

Formula XVI

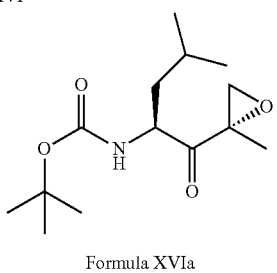

Formula XVIa

Pereira et al., in *ChemBioChem* 2012, 13, 810-817 discloses a process for the preparation of compound of Formula XVI starting from boc-Leucine. The process disclosed by Pereira et al is schematically represented as follows:

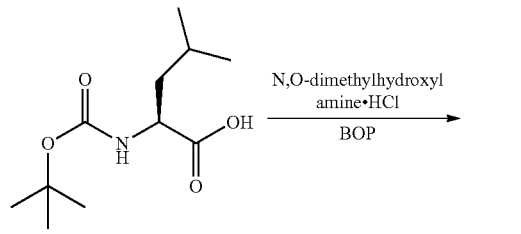

Boc-Leu

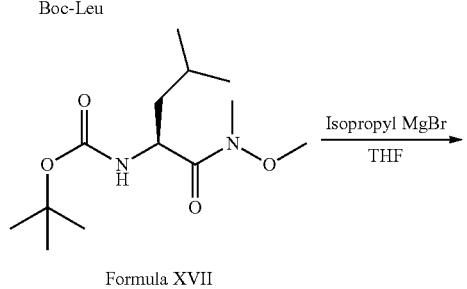

Formula XVII

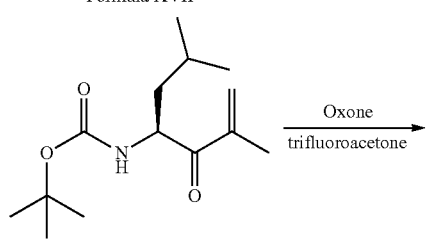

Formula XVIII

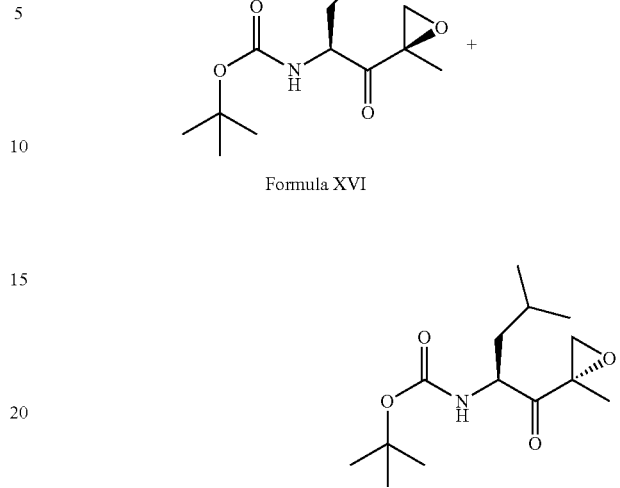

Formula XVI

Formula XVIa

PCT publication No. 2014/003203 ("the '203 publication") discloses a process for compound of Formula XVI, by reduction of compound of Formula XVIII in presence of amine borane complex and further converted in to diastereomeric mixture of compound of Formula XVI and Formula XVIa. The process disclosed in the '203 publication is schematically represented as follows:

Formula XVI

Wang et al., in *Chemistry—A European Journal* 2012, vol. 18, Issue 22, Page-6750-6753 discloses a process for epoxidation of Formula XVIII in presence of hydrogen peroxide to obtain diastereomeric mixture of compound of Formula XVI and Formula XVIa in 1:7 ratio. The process disclosed by Wang et al is schematically represented as follows:

Formula XVIII

Formula XIXa

Formula XIXb

-continued

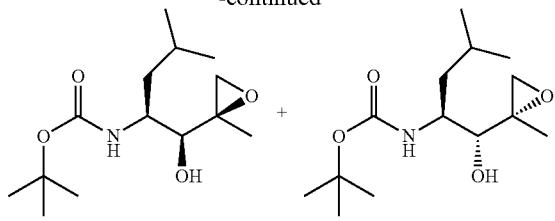

Formula XXa     Formula XXb

N-hydroxy-2-azaadamantane
Purification from EtOH:DMF:water

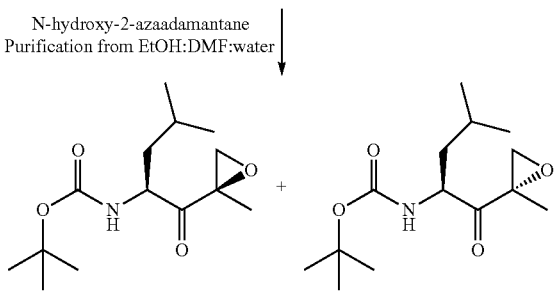

Formula XVI     Formula XVIa

As compound of Formula XVI and Formula XVIII have almost marginal polarity differences, compound of Formula XVI is readily isolated along with compound of Formula XVIII as an impurity in oily liquid state, thus compound of Formula XVIII is not possible to separate out from the mixture. Thereby unwanted formula XVIII is involved in the further sequential steps in preparation of carfilzomib, leads to formation of impurity of Formula 28.

Formula 28

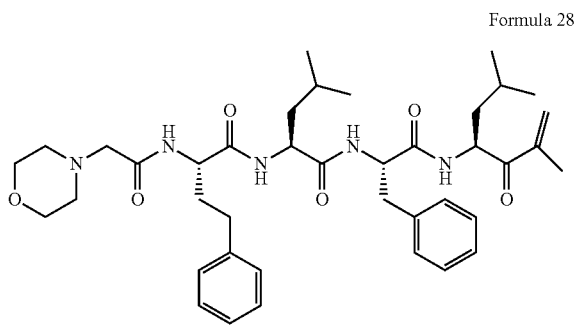 [SMILES: C=C(C)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1]

All the above described processes involve isolation of intermediate compound of Formula XVIII, Formula XIX and Formula XVI as an oily nature, which are having higher content of process impurities thereby using such impure intermediates in the preparation of carfilzomib leads to formation of impure product.

Further, numerous CN publication No.(s) 103641890, 103864889, 103864898, 103936828, 103804469, 104086624, 104230857, 104356197, 104557793, 104672179, 104672180, 104710507, 105017181, 105273057, 105294501, 105218488 and 105440106 discloses process for preparation of carfilzomib and its intermediates thereof.

Reported literatures on preparation of carfilzomib involves N-boc-L-leucine of Formula II, L-phenyl alanine benzyl ester of Formula III, N-boc-L-Homophenylalanine of Formula VI and Formula IX as intermediates, which contains traces of its corresponding D-isomers or isoleucine compounds as impurities which tends to react in the same sequential manner to generate the corresponding isomers as impurities, which requires repetitive purifications to separate from the final API.

Different isomers of a chiral drug molecule bind differently to target receptors, one isomer of a drug may have a desired beneficial effect while the other may cause serious and undesired side effects or sometimes even beneficial but entirely different effect, hence in the drug molecule the effective isomer is preferred in pure form, free of other undesired isomers, thus carfilzomib free of its other isomers would always be preferred.

Presence of impurities in a pharmaceutical compound is undesirable and health authorities in many jurisdictions (e.g. the Food and Drug Administration in the United States) have established guidelines relating to acceptable levels of impurities in pharmaceuticals. The need for and commercial utility of methods of reducing the level of impurities in any pharmaceutical are self-evident.

Based on the drawbacks mentioned above, there is a vital need to develop a process for the preparation of carfilzomib or a pharmaceutically acceptable salt thereof and its intermediates, which is readily amenable to large scale production with higher purity and yield.

Hence, present inventors focused research to simplify the process for the preparation of carfilzomib or a pharmaceutically acceptable salt thereof, which avoids mainly usage of excess quantity of reagents and solvents as compared to the prior-art processes, thereby making the process more suitable for commercial applications with higher purity, yield and obviate the problems associated with the reported process.

The present invention further relates to crystalline maleate salt of carfilzomib and its process for preparation thereof. The present invention furthermore relates to process for preparation of amorphous form of carfilzomib.

The present invention also relates to process for preparation of highly pure compound of Formula XVI and its intermediates in solid state, which is necessary for obtaining high pure carfilzomib API.

SUMMARY OF THE INVENTION

In accordance with one embodiment, the present invention provides an improved process for the preparation of carfilzomib of Formula I or a pharmaceutically acceptable salt thereof:

Formula I

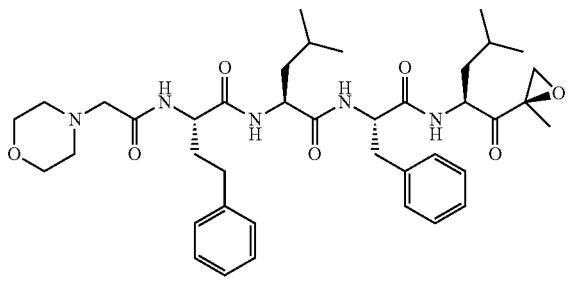

comprising:
a) reacting a compound of Formula II with a compound of Formula III or a salt thereof in presence of a coupling agent (C1), an additive (A1) and a base (B1) in a suitable solvent (S1) to obtain a compound of Formula IV, Formula II

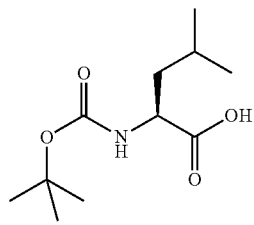

Formula III

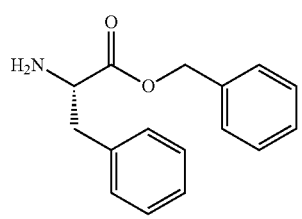

Formula IV

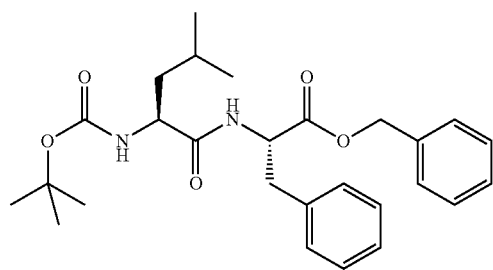

b) reacting the compound of Formula IV with a suitable acid to obtain a compound of Formula V or a salt thereof, Formula V

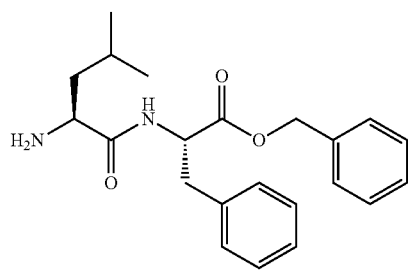

c) reacting the compound of Formula V or a salt thereof with a compound of Formula VI in presence of a coupling agent (C2), an additive (A2) and a base (B2) in a suitable solvent (S2) to obtain a compound of Formula VII, Formula VI

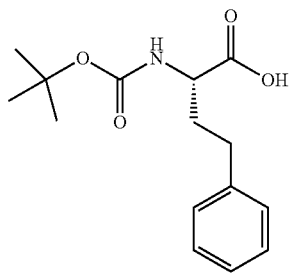

Formula VII

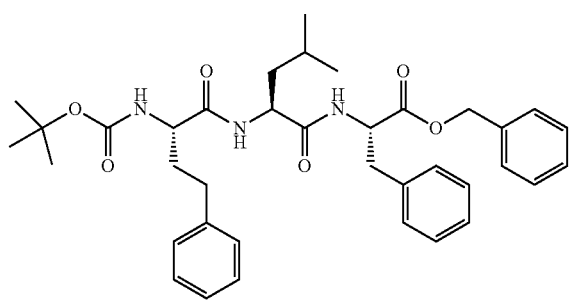

d) deprotecting the compound of Formula VII in presence of a suitable deprotecting agent to obtain a compound of Formula VIII, Formula VIII

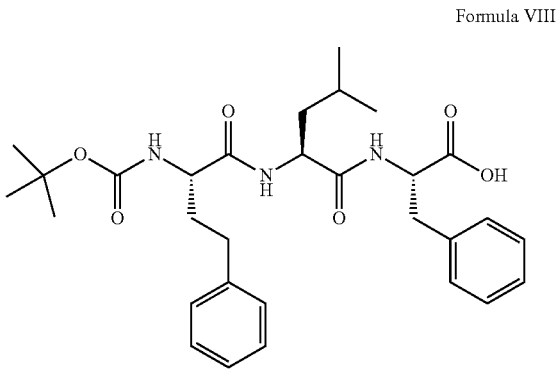 [SMILES: CC(C)C[C@H](NC(=O)[C@H](CCc1ccccc1)NC(=O)OC(C)(C)C)C(=O)N[C@@H](Cc1ccccc1)C(=O)O]

e) reacting the compound of Formula VIII with a compound of Formula IX or a salt thereof in presence of a coupling agent (C3), an additive (A3) and a base (B3) in a suitable solvent (S3) to obtain a compound of Formula X, Formula IX

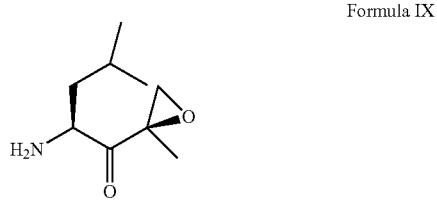

-continued

Formula X

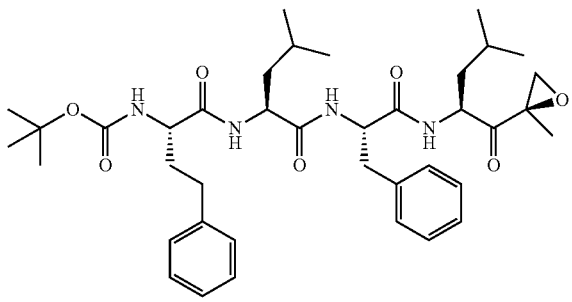

f) reacting the compound of Formula X with a suitable acid to obtain a compound of Formula XI or a salt thereof, and Formula XI

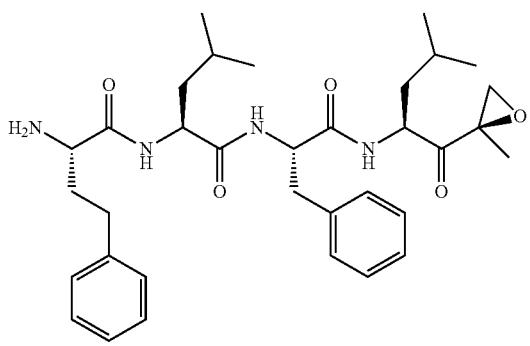

g) reacting the compound of Formula XI or a salt thereof with a compound of Formula XII or a salt thereof in presence of a coupling agent (C4), an additive (A4) and a base (B4) in a suitable solvent (S4) to obtain carfilzomib or a pharmaceutically acceptable salt thereof, Formula XII

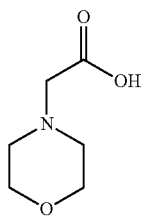

wherein the coupling agent (C1), (C2), (C3) and (C4) are used in an amount of about 0.9 to about 1.3 w/w mole equivalents per mole of Formula III, Formula IV, Formula VIII and Formula X respectively;
wherein the additive (A1), (A2), (A3) and (A4) are used in catalytic amount of about 0.05 to about 0.5 w/w mole equivalents per mole of Formula III, Formula IV, Formula VIII and Formula X respectively.

In accordance another embodiment, the present invention provides an improved process for the preparation of carfilzomib of Formula I or a pharmaceutically acceptable salt thereof; comprising:
a) reacting a compound of Formula VIII with a compound of Formula IX or a salt thereof in presence of a coupling agent (C3), an additive (A3) and a base (B3) in a suitable solvent (S3) to obtain a compound of Formula X,
b) reacting the compound of Formula X with a suitable acid to obtain a compound of Formula XI or a salt thereof, and
c) reacting the compound of Formula XI or a salt thereof with a compound of Formula XII or a salt thereof in presence of a coupling agent (C4), an additive (A4) and a base (B4) in a suitable solvent (S4) to obtain carfilzomib or a pharmaceutically acceptable salt thereof,
wherein the coupling agent (C3) and (C4) are used in an amount of about 0.9 to about 1.3 w/w mole equivalents per mole of Formula VIII and Formula X respectively;
wherein the additive (A3) and (A4) are used in catalytic amount of about 0.05 to about 0.5 w/w mole equivalents per mole of Formula VIII and Formula X respectively.

In accordance another embodiment, the present invention provides an improved process for the preparation of carfilzomib of Formula I or a pharmaceutically acceptable salt thereof; comprising:
a) reacting a compound of Formula X with a suitable acid to obtain a compound of Formula XI or a salt thereof, and
b) reacting the compound of Formula XI or a salt thereof with a compound of Formula XII or a salt thereof in presence of a coupling agent (C4), an additive (A4) and a base (B4) in a suitable solvent (S4) to obtain carfilzomib or a pharmaceutically acceptable salt thereof,
wherein the coupling agent C4 is used in an amount of about 0.9 to about 1.3 w/w mole equivalents per mole of Formula X;
wherein the additive A4 is used in catalytic amount of about 0.05 to about 0.5 w/w mole equivalents per mole of Formula X.

In accordance another embodiment, the present invention provides an improved process for the preparation of carfilzomib of Formula I or a pharmaceutically acceptable salt thereof; comprising: reacting a compound of Formula XI or a salt thereof with a compound of Formula XII or a salt thereof in presence of a coupling agent (C4), an additive (A4) and a base (B4) in a suitable solvent (S4) to obtain carfilzomib or a pharmaceutically acceptable salt thereof.

In accordance with another embodiment, the present invention provides an improved process for preparation of carfilzomib of Formula I or a pharmaceutically acceptable salt thereof; comprising: reacting a compound of Formula XI or a salt thereof with a compound of Formula XII or a salt thereof in presence of a coupling agent (C4), an additive (A4) and a base (B4) in a suitable solvent (S4) to obtain carfilzomib or a pharmaceutically acceptable salt thereof; wherein the coupling agent (C4) is used in an amount of about 0.9 to about 1.3 w/w mole equivalents per mole of Formula X; wherein the additive (A4) is used in catalytic amount of about 0.05 to about 0.5 w/w mole equivalents per mole of Formula X.

In accordance another embodiment, the present invention provides an improved process for preparation of carfilzomib of Formula I or a pharmaceutically acceptable salt thereof comprising:
a) reacting a compound of Formula II with a compound of Formula III or a salt thereof in presence of a coupling agent (C1), an additive (A1) and a base (B1) in a suitable solvent (S1) to obtain a compound of Formula IV, wherein the coupling agent (C1) is used in an amount of about 0.9 to about 1.3 w/w mole equivalents per mole of Formula III; wherein the additive (A1) is used in catalytic amount of about 0.05 to about 0.5 w/w mole equivalents per mole of Formula III, and b) converting the compound of Formula IV into compound of Formula I or a pharmaceutically acceptable salt thereof.

In accordance with another embodiment, the present invention provides an improved process for preparation of carfilzomib of Formula I or a pharmaceutically acceptable salt thereof; comprising:

a) reacting a compound of Formula V with a compound of Formula VI in presence of a coupling agent (C2), an additive (A2) and a base (B2) in a suitable solvent (S2) to obtain a compound of Formula VII, wherein the coupling agent (C2) is used in an amount of about 0.9 to about 1.3 w/w mole equivalents per mole of Formula IV; wherein the additive (A2) is used in catalytic amount of about 0.05 to about 0.5 w/w mole equivalents per mole of Formula IV, and b) converting the compound of Formula VII into compound of Formula I or a pharmaceutically acceptable salt thereof.

In accordance with another embodiment, the present invention provides an improved process for preparation of carfilzomib of Formula I or a pharmaceutically acceptable salt thereof; comprising:

a) reacting a compound of Formula VIII with a compound of Formula IX or a salt thereof in presence of a coupling agent (C3), an additive (A3) and a base (B3) in a suitable solvent (S3) to obtain a compound of Formula X; wherein the coupling agent (C3) is used in an amount of about 0.9 to about 1.3 w/w mole equivalents per mole of Formula VIII; wherein the additive (A3) is used in catalytic amount of about 0.05 to about 0.5 w/w mole equivalents per mole of Formula VIII, and b) converting the compound of Formula X into compound of Formula I or a pharmaceutically acceptable salt thereof.

In accordance with another embodiment, the present invention provides a process for purification of compound of Formula X, comprising:

a) dissolving compound of Formula X in one or more suitable solvent at a temperature of about 30° C. to about reflux temperature, b) cooling the obtained solution to less than 10° C., and c) filtering the compound of Formula X.

In another embodiment, the present invention provides a process for purification of carfilzomib, comprising:

a) providing a solution of carfilzomib in one or more organic solvents, b) adding maleic acid to the step a) solution, c) isolating the carfilzomib maleic acid salt, d) neutralizing the carfilzomib maleic acid salt in a suitable solvent using a base, e) concentrating the step d) solution under vacuum to obtain a residue, f) dissolving the step e) residue in a suitable solvent, g) adding the step f) solution to an anti-solvent, or vice-versa, and h) isolating the pure carfilzomib.

In accordance with another embodiment, the present invention provides a process for preparation of amorphous Form of carfilzomib, comprising:

a) providing a solution of carfilzomib pharmaceutically acceptable salt in a suitable solvent, b) neutralizing the step a) solution with a base, c) concentrating the step b) solution under vacuum to obtain a residue, d) dissolving the step c) residue in a suitable solvent, e) adding the step d) solution to an anti-solvent, or vice-versa and f) isolating the amorphous form of carfilzomib.

In accordance with another embodiment, the present invention provides a process for preparation of amorphous Form of carfilzomib, comprising:

a) providing a solution of carfilzomib maleate salt in methylene chloride, b) neutralizing the step a) solution with a base, c) concentrating the step b) solution under vacuum to obtain a residue, d) dissolving the step c) residue in methanol, e) adding the step d) solution to water, or vice-versa and f) isolating the amorphous form of carfilzomib.

In accordance with another embodiment, the present invention provides a process for preparation of crystalline maleate salt of carfilzomib, comprising:

a) providing a solution of carfilzomib in one or more organic solvents, b) adding maleic acid to the step a) solution, and c) isolating the carfilzomib maleate salt.

In accordance with another embodiment, the present invention provides an improved process for the preparation of carfilzomib of Formula I or a pharmaceutically acceptable salt thereof:

Formula I

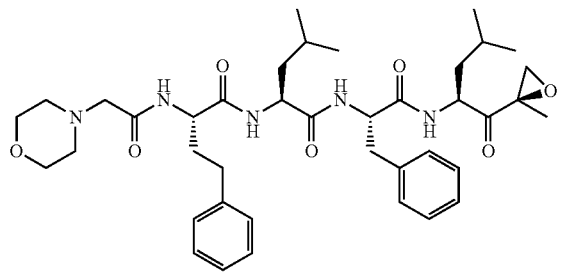

comprising:

a1) reacting a compound of Formula II with a compound of Formula III or a salt thereof in presence of a coupling agent (C1), an additive (A1) and a base (B1) in a suitable solvent (S1) to obtain a compound of Formula IV, Formula II

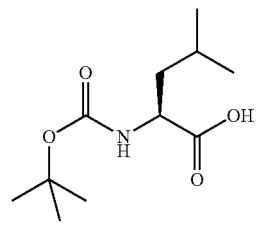

Formula III

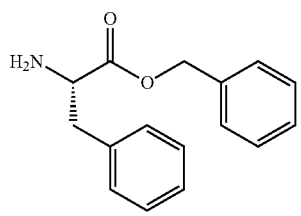

Formula IV

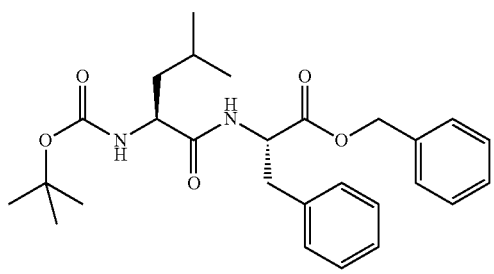

b1) reacting the compound of Formula IV with a suitable acid to obtain a compound of Formula V or a salt thereof, Formula V

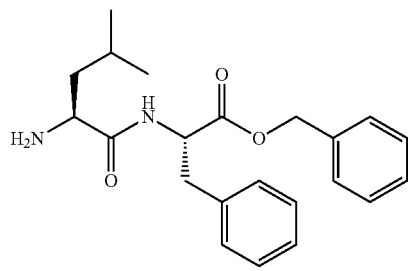

c1) reacting the compound of Formula V or a salt thereof with a compound of Formula VI in presence of a coupling agent (C2), an additive (A2) and a base (B2) in a suitable solvent (S2) to obtain a compound of Formula VII, Formula VI

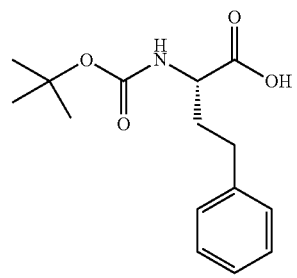

Formula VII

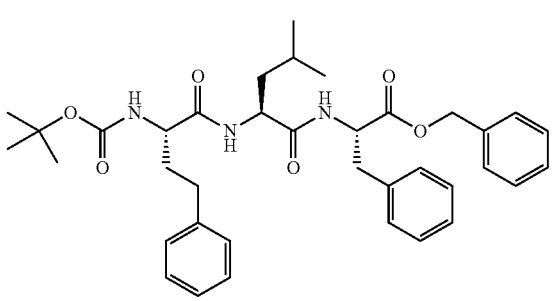

d1) reacting the compound of Formula VII with a suitable acid to obtain a compound of Formula XIII or a salt thereof, Formula XIII

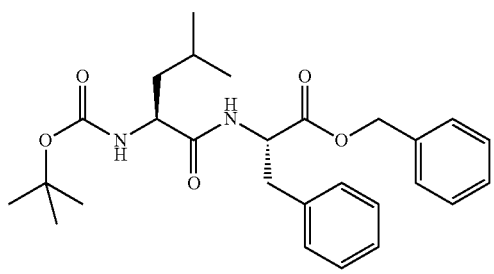

e1) reacting the compound of Formula XIII or a salt thereof with a compound of Formula XII in presence of a coupling agent (C5), an additive (A5) and a base (B5) in a suitable solvent (S5) to obtain a compound of Formula XIV, Formula XII

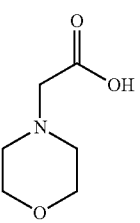

Formula XIV

f1) deprotecting the compound of Formula XIV in presence of a suitable deprotecting agent to obtain a compound of Formula XV, and Formula XV

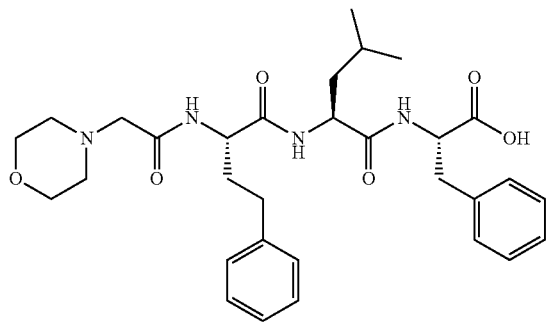

g1) reacting the compound of Formula XV with a compound of Formula IX or a salt thereof in presence of a coupling agent (C6), an additive (A6) and a base (B6) in a suitable solvent (S6) to obtain carfilzomib or a pharmaceutically acceptable salt thereof, Formula IX

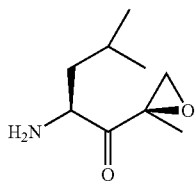

wherein the coupling agent (C1), (C2), (C5) and (C6) are used in an amount of about 0.9 to about 1.3 w/w mole equivalents per mole of Formula III, Formula IV, Formula VII and Formula XV respectively;
wherein the additive (A1), (A2), (A5) and (A6) are used in catalytic amount of about 0.05 to about 0.5 w/w mole equivalents per mole of Formula III, Formula IV, Formula VII and Formula XV respectively.

In accordance with another embodiment, the present invention provides an improved process for preparation of carfilzomib of Formula I or a pharmaceutically acceptable salt thereof; comprising:
a1) reacting a compound of Formula XIII or a salt thereof with a compound of Formula XII in presence of a coupling agent (C5), an additive (A5) and a base (B5) in a suitable solvent (S5) to obtain a compound of Formula XIV, wherein the coupling agent (C5) is used in an amount of about 0.9 to about 1.3 w/w mole equivalents per mole of Formula VII; wherein the additive (A5) is used in catalytic amount of about 0.05 to about 0.5 w/w mole equivalents per mole of Formula VII, and
b1) converting the compound of Formula XIV into compound of Formula I or a pharmaceutically acceptable salt thereof.

In accordance with another embodiment, the present invention provides an improved process for preparation of carfilzomib of Formula I or a pharmaceutically acceptable salt thereof; comprising: reacting a compound of Formula XV with a compound of Formula IX or a salt thereof in presence of a coupling agent (C6), an additive (A6) and a base (B6) in a suitable solvent (S6) to obtain carfilzomib or a pharmaceutically acceptable salt thereof; wherein the coupling agent (C6) is used in an amount of about 0.9 to about 1.3 w/w mole equivalents per mole of Formula XV; wherein the additive (A6) is used in catalytic amount of about 0.05 to about 0.5 w/w mole equivalents per mole of Formula XV.

In accordance with another embodiment, the present invention provides a process for the purification of tert-butyl ((2S)-4-methyl-1-((2R)-2-methyloxirane-2-yl)-1-oxo-pentan-2-yl)-carbamate of Formula XVI, Formula XVI

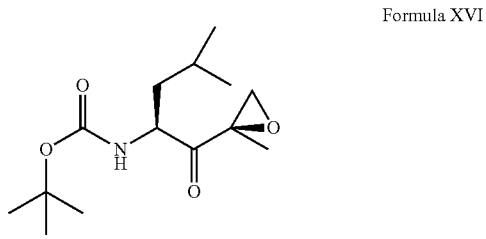 [SMILES: CC(C)C[C@H](NC(=O)OC(C)(C)C)C(=O)[C@@]1(C)CO1]

comprising:
i) providing a solution of tert-butyl ((2S)-4-methyl-1-((2R)-2-methyloxirane-2-yl)-1-oxo-pentan-2-yl)-carbamate of Formula XVI in a suitable solvent,
ii) cooling the step i) solution to less than 5° C.,
iii) optionally adding seed compound of Formula XVI to the step ii) solution, and
iv) isolating the pure compound of Formula XVI; wherein the suitable solvent is selected from aliphatic hydrocarbons, cyclic hydrocarbons, ethers and the like and mixture thereof.

In accordance with another embodiment, the present invention provides a process for the purification of tert-butyl ((2S)-4-methyl-1-((2R)-2-methyloxirane-2-yl)-1-oxo-pentan-2-yl)-carbamate of Formula XVI having less than 0.1% by HPLC of compound of Formula XVIII, comprising:
i) providing a solution of tert-butyl ((2S)-4-methyl-1-((2R)-2-methyloxirane-2-yl)-1-oxo-pentan-2-yl)-carbamate of Formula XVI in a suitable solvent,
ii) cooling the step i) solution to less than 5° C.,
iii) optionally adding seed compound of Formula XVI to the step ii) solution, and
iv) isolating the pure compound of Formula XVI; wherein the suitable solvent is selected from aliphatic hydrocarbons, cyclic hydrocarbons, ethers and the like and mixture thereof.

In accordance with another embodiment, the present invention provides a process for the preparation of tert-butyl ((2 S)-4-methyl-1-((2R)-2-methyloxirane-2-yl)-1-oxo-pentan-2-yl)-carbamate of Formula XVI, Formula XVI

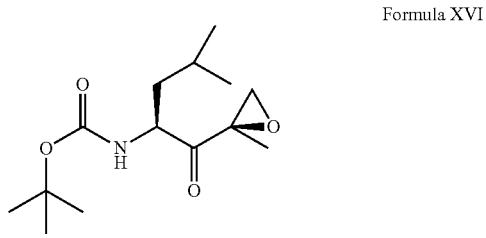 [SMILES: CC(C)C[C@H](NC(=O)OC(C)(C)C)C(=O)[C@@]1(C)CO1]

comprising:
i) reacting a compound of Formula XVII with alkyl magnesium halide to obtain a compound of Formula XVIII as a crystalline solid, Formula XVII

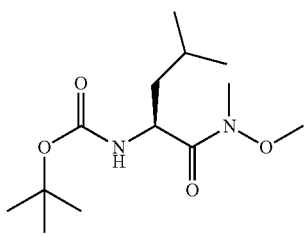

Formula XVIII

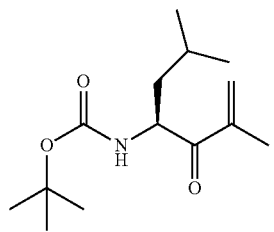

ii) reducing the compound of Formula XVIII in presence of a suitable reducing agent to obtain a diastereomeric mixture of compound of Formula XIXa and Formula XIXb as a crystalline solid, Formula XIXa

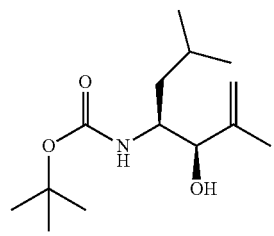

Formula XIXb

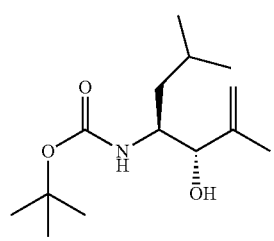

iii) epoxidation and followed by oxidation of the diastereomeric mixture of compound of Formula XIXa and Formula XIXb to obtain a diastereomeric mixture of compound of Formula XVI and Formula XVIa, Formula XVI

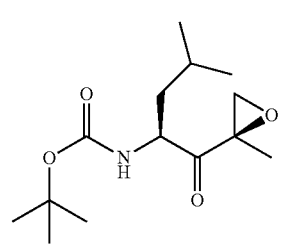

Formula XVIa

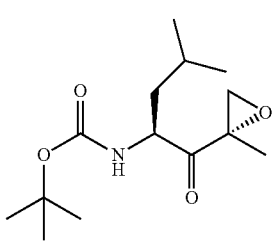

iv) separating the compound of Formula XVI from the diastereomeric mixture of compound of Formula XVI and Formula XVIa by chromatography, v) crystallizing the compound of Formula XVI from a suitable solvent, wherein the suitable solvent is selected from aliphatic hydrocarbons, cyclic hydrocarbons, ethers and the like and mixture thereof, and vi) isolating the compound of Formula XVI as a crystalline solid.

In accordance with another embodiment, the present invention provides a process for preparation of tert-butyl ((2 S)-4-methyl-1-((2R)-2-methyloxirane-2-yl)-1-oxo-pentan-2-yl)-carbamate of Formula XVI, Formula XVI

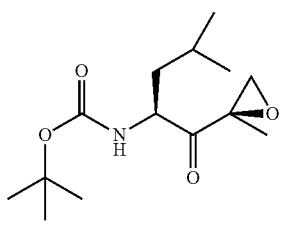

comprising:
i) reacting a compound of Formula XVII with alkyl magnesium halide to obtain a compound of Formula XVIII,
ii) crystallizing the compound of Formula XVIII from a suitable solvent system to obtain crystalline compound of Formula XVIII, Formula XVII

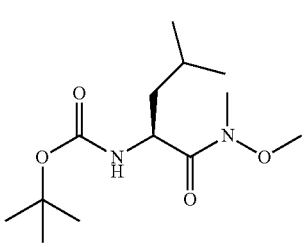

Formula XVIII

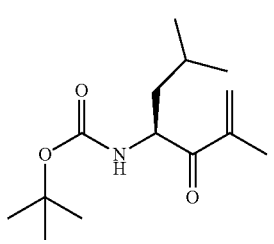

iii) reducing the crystalline compound of Formula XVIII in presence of a suitable reducing agent to obtain a diastereomeric mixture of compound of Formula XIXa and Formula XIXb, iv) crystallizing the mixture of compound of Formula XIXa and Formula XIXb from a suitable solvent system to obtain a mixture of crystalline compound of Formula XIXa and Formula XIXb, Formula XIXa

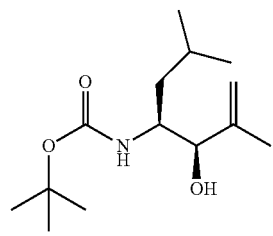

Formula XIXb

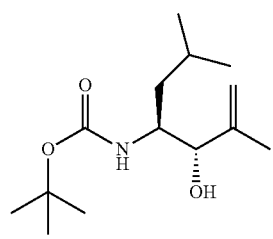

v) epoxidation and followed by oxidation of diastereomeric mixture of crystalline compound of Formula XIXa and Formula XIXb to obtain a diastereomeric mixture of compound of Formula XVI and Formula XVIa, Formula XVI

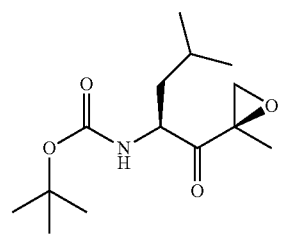

Formula XVIa

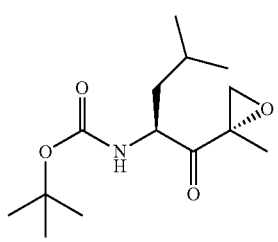

vi) separating the compound of Formula XVI from the diastereomeric mixture of compound of Formula XVI and Formula XVIa by chromatography, and vii) crystallizing the compound of Formula XVI from a suitable solvent system to obtain crystalline compound of Formula XVI.

In accordance with another embodiment, the present invention provides a process for the preparation of compound of Formula XVIII as crystalline solid, comprising:

i) providing a solution of compound of Formula XVIII in a suitable solvent, ii) optionally cooling the step i) solution to less than 20° C., iii) adding an anti-solvent to the step ii) solution, and iv) isolating the crystalline compound of Formula XVIII; wherein the suitable solvent is selected from the group comprising alcohols, ketones, esters, nitriles and the like and mixture thereof; and the anti-solvent is selected from the group comprising aliphatic hydrocarbons, cyclic hydrocarbons, ethers and the like and water and mixture thereof.

In accordance with another embodiment, the present invention provides a process for the preparation of diastereomeric mixture of compound of Formula XIXa and Formula XIXb as a crystalline solid, comprising:

i) providing a solution of diastereomeric mixture of a compound of Formula XIXa and Formula XIXb in a suitable solvent, ii) cooling the step i) solution to less than 10° C., iii) adding an anti-solvent to the step ii) solution, and iv) isolating the crystalline compound of Formula XIX; wherein the suitable solvent is selected from the group comprising alcohols, ketones, esters, nitriles and the like and mixture thereof; and the anti-solvent is selected from the group comprising aliphatic hydrocarbons, cyclic hydrocarbons, ethers and the like and water and mixture thereof.

In accordance with another embodiment, the present invention provides an improved process for the preparation of carfilzomib, comprising preparing the tert-butyl ((2S)-4-methyl-1-((2R)-2-methyloxirane-2-yl)-1-oxo-pentan-2-yl)-carbamate of Formula XVI as process described above, and converting the tert-butyl ((2S)-4-methyl-1-((2R)-2-methyloxirane-2-yl)-1-oxo-pentan-2-yl)-carbamate of Formula XVI in to carfilzomib.

In accordance with another embodiment, the present invention provides an improved process for the preparation of carfilzomib having less than 0.1% of Formula 28 by HPLC, comprising:

i) providing a solution of tert-butyl ((2S)-4-methyl-1-((2R)-2-methyloxirane-2-yl)-1-oxo-pentan-2-yl)-carbamate of Formula XVI in a suitable solvent, ii) cooling the step i) solution to less than 5° C., iii) optionally adding seed compound of Formula XVI to the step ii) solution, iv) isolating the pure compound of Formula XVI having less than 0.1% by HPLC of compound of Formula XVIII; and v) converting the pure compound of Formula XVI into carfilzomib; wherein the suitable solvent is selected from aliphatic hydrocarbons, cyclic hydrocarbons, ethers and the like and mixture thereof.

In accordance with another embodiment, the present invention provides compound of Formula XVI containing less than 0.1% of compound of Formula XVIII as measured by HPLC.

In accordance with another embodiment, the present invention provides crystalline tert-butyl ((2S)-4-methyl-1-((2R)-2-methyloxirane-2-yl)-1-oxo-pentan-2-yl)-carbamate of Formula XVI characterized by a powder X-Ray diffraction (PXRD) pattern substantially in accordance with FIG. 8.

In accordance with another embodiment, the present invention provides crystalline tert-butyl ((4S)-2,6-dimethyl-3-oxo hept-1-en-4-yl))carbamate of Formula XVIII characterized by a powder X-Ray diffraction (PXRD) pattern substantially in accordance with FIG. 9.

In accordance with another embodiment, the present invention provides crystalline tert-butyl N-[(3R/S,4S)-3-hydroxy-2,6-dimethylhept-1-en-4-yl]carbamate of Formula XIX characterized by a powder X-Ray diffraction (PXRD) pattern substantially in accordance with FIG. 10.

In accordance with another embodiment, the present invention provides carfilzomib containing less than 0.05% as measured by HPLC of one or more of impurities of Formula 1 to Formula 41; preferably 0.03% as measured by HPLC.

In accordance with another embodiment, the present invention provides a compound of Formula 41:

Formula 41

In accordance with another embodiment, the present invention provides amorphous compound of Formula IV.

In accordance with another embodiment, the present invention provides amorphous compound of Formula IV characterized by a powder X-Ray diffraction (PXRD) pattern substantially in accordance with FIG. 1.

In accordance with another embodiment, the present invention provides amorphous compound of Formula VII.

In accordance with another embodiment, the present invention provides amorphous compound of Formula VII characterized by a powder X-Ray diffraction (PXRD) pattern substantially in accordance with FIG. 2.

In accordance with another embodiment, the present invention provides amorphous compound of Formula VIII.

In accordance with another embodiment, the present invention provides amorphous compound of Formula VIII characterized by a powder X-Ray diffraction (PXRD) pattern substantially in accordance with FIG. 3.

In accordance with another embodiment, the present invention provides crystalline compound of Formula X.

In accordance with another embodiment, the present invention provides crystalline compound of Formula X characterized by a powder X-Ray diffraction (PXRD) pattern substantially in accordance with FIG. 4.

In accordance with another embodiment, the present invention provides amorphous compound of Formula XI trifluoro acetic acid salt.

In accordance with another embodiment, the present invention provides amorphous compound of Formula XI trifluoro acetic acid salt characterized by a powder X-Ray diffraction (PXRD) pattern substantially in accordance with FIG. 5.

In accordance with another embodiment, the present invention provides amorphous compound of Formula XI free amine.

In accordance with another embodiment, the present invention provides amorphous compound of Formula XI free amine characterized by a powder X-Ray diffraction (PXRD) pattern substantially in accordance with FIG. 6.

In accordance with another embodiment, the present invention provides crystalline carfilzomib maleate salt.

In accordance with another embodiment, the present invention provides crystalline carfilzomib maleate salt characterized by a powder X-Ray diffraction (PXRD) pattern substantially in accordance with FIG. 7.

In accordance with another embodiment, the present invention provides a pharmaceutical composition comprising carfilzomib or a pharmaceutically acceptable salt thereof prepared by the processes of the present invention and at least one pharmaceutically acceptable excipient.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
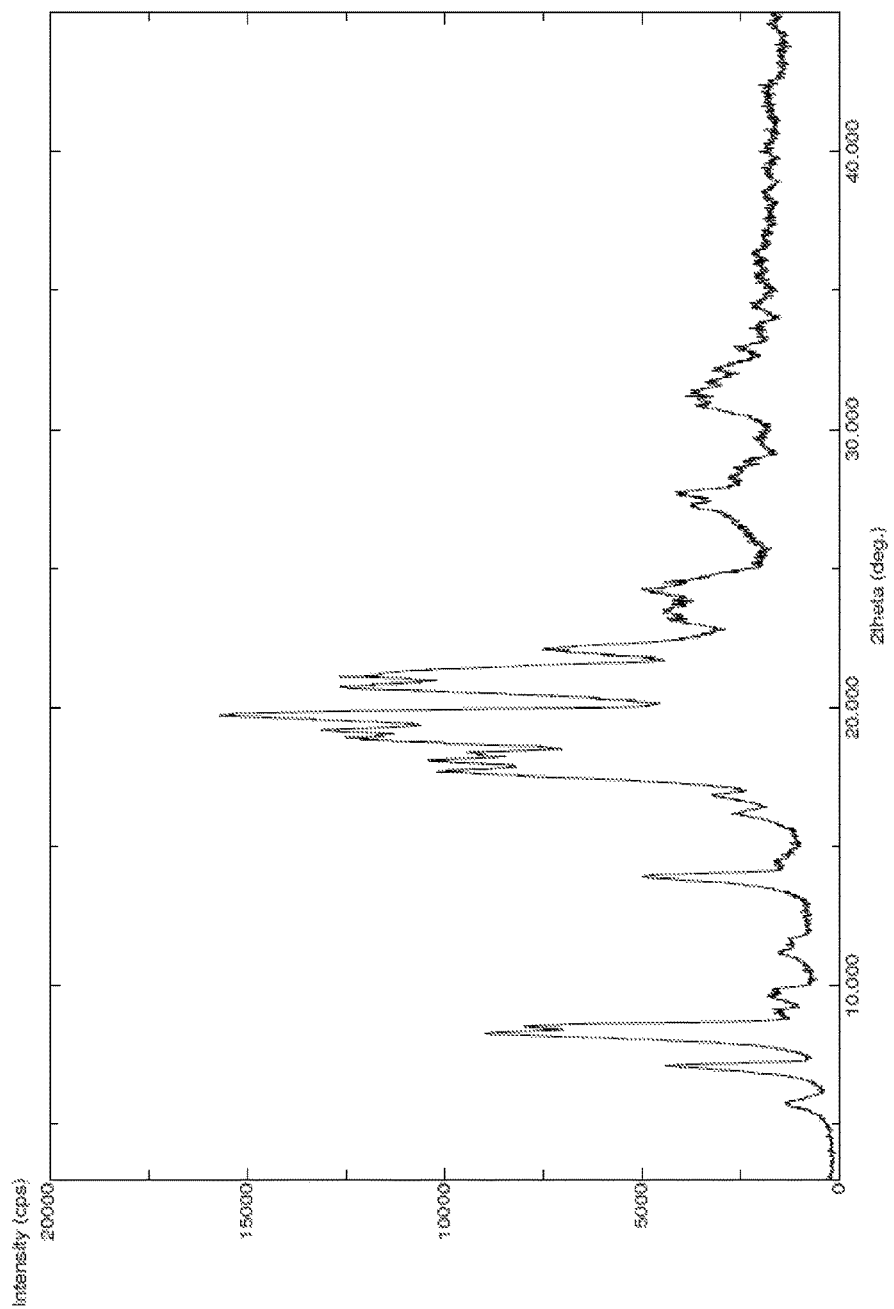
FIG. 1 is the characteristic powder X-ray diffraction (XRD) pattern of amorphous compound of Formula IV.

The present invention encompasses an improved process for preparation of carfilzomib or a pharmaceutically acceptable salt thereof. The present invention also relates to a process for preparation of carfilzomib amorphous form.

The present invention further relates to carfilzomib maleate salt, a process for its preparation and its use as intermediate in the preparation of carfilzomib.

In accordance with one embodiment, the present invention provides an improved process for the preparation of carfilzomib of Formula I or a pharmaceutically acceptable salt thereof:

Formula I

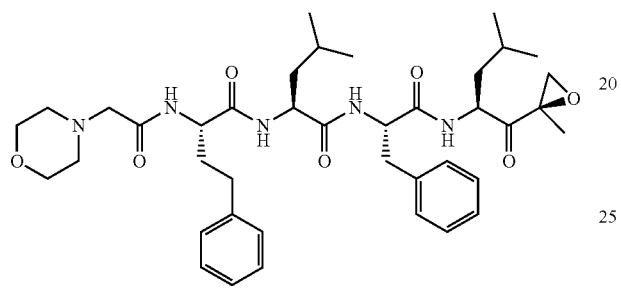

comprising:
a) reacting a compound of Formula II with a compound of Formula III or a salt thereof in presence of a coupling agent (C1), an additive (A1) and a base (B1) in a suitable solvent (S1) to obtain a compound of Formula IV, Formula II

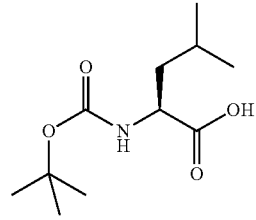

Formula III

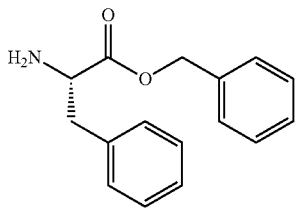

Formula IV

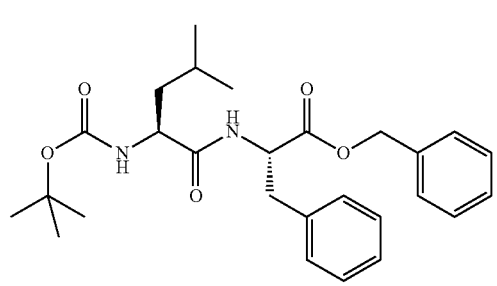

b) reacting the compound of Formula IV with a suitable acid to obtain a compound of Formula V or a salt thereof, Formula V

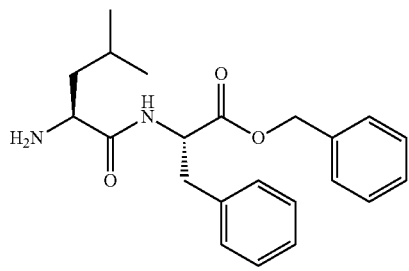

c) reacting the compound of Formula V or a salt thereof with a compound of Formula VI in presence of a coupling agent (C2), an additive (A2) and a base (B2) in a suitable solvent (S2) to obtain a compound of Formula VII, Formula VI

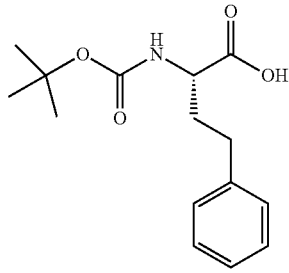

Formula VII

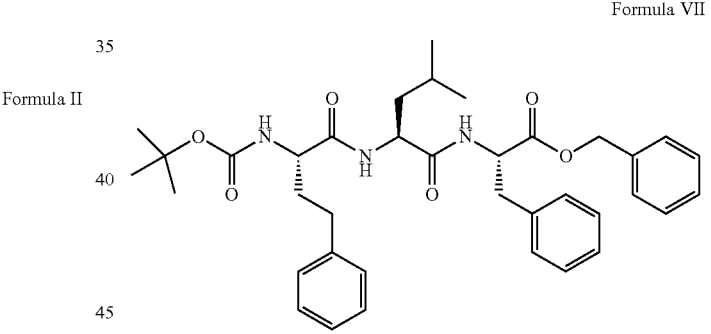

d) deprotecting the compound of Formula VII in presence of a suitable deprotecting agent to obtain a compound of Formula VIII, Formula VIII

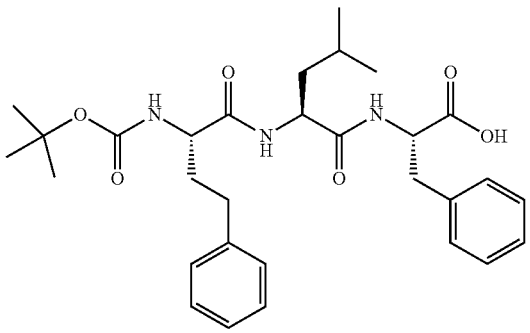

e) reacting the compound of Formula VIII with a compound of Formula IX or a salt thereof in presence of a coupling agent (C3), an additive (A3) and a base (B3) in a suitable solvent (S3) to obtain a compound of Formula X, Formula IX

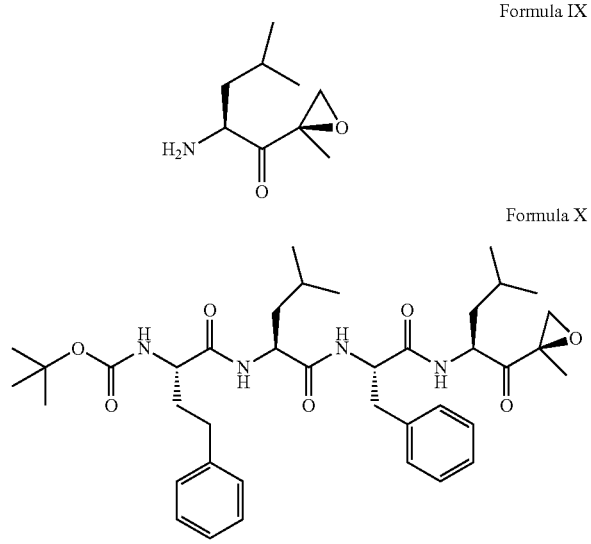

f) reacting the compound of Formula X with a suitable acid to obtain a compound of Formula XI or a salt thereof, and Formula XI g) reacting the compound of Formula XI or a salt thereof with a compound of Formula XII or a salt thereof in presence of a coupling agent (C4), an additive (A4) and a base (B4) in a suitable solvent (S4) to obtain carfilzomib or a pharmaceutically acceptable salt thereof, Formula XII wherein the coupling agent (C1), (C2), (C3) and (C4) are used in an amount of about 0.9 to about 1.3 w/w mole equivalents per mole of Formula III, Formula IV, Formula VIII and Formula X respectively;

wherein the additive (A1), (A2), (A3) and (A4) are used in catalytic amount of about 0.05 to about 0.5 w/w mole equivalents per mole of Formula III, Formula IV, Formula VIII and Formula X respectively.

The compound of Formula II, L-phenyl alanine benzyl ester of Formula III or a salt thereof, N-boc-homophenylalanine of Formula VI and morpholine acetic acid of Formula XII are known in the art and can be procured from commercially available sources.

The suitable salt of compounds of Formula III, Formula V, Formula IX, Formula XI or Formula XII employed in the aforementioned process is a salt of a mineral or organic acid, such as HCl, HBr, HI, HNO$_3$, H$_2$SO$_4$, acetic acid, trifluoro acetic acid, formic acid and the like.

The '818 patent process involves peptide coupling reactions using excess quantity of coupling agents, additives and solvents. The use of excess quantity of such coupling reagents contaminate in each step with the required product, also involves formation of by-product such as tris(pyrrolidino phosphine) oxide and it necessitates separate purification techniques to separate out unwanted coupling agents and/or by-products, which contributes significant impact on the final yield and purity, which makes the process not viable for large scale manufacturing. Further, the process involves long reaction times, which leads to an increase in the manufacturing cycle time and decrease in the product yield and quality.

Further reported literatures on preparation of carfilzomib involves N-boc-L-leucine of Formula II, L-phenyl alanine benzyl ester of Formula III, N-boc-L-homophenylalanine of Formula VI and Formula IX as intermediates, which contains traces of its corresponding D-isomers or its isoleucine compounds as impurities which tends to react in the same sequential manner to generate the corresponding isomers of Formula 1-41 as impurities, which requires repetitive purifications to separate from the final API.

Formula 1

Formula 2

Formula 3
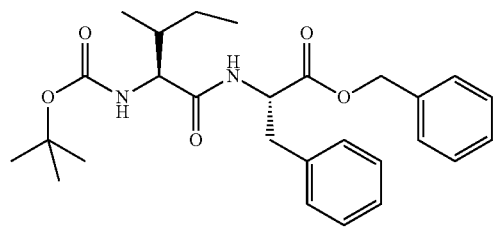
Formula 4
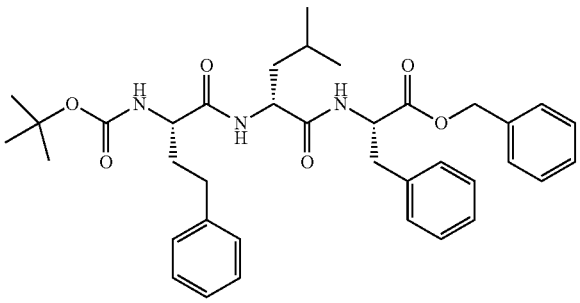
Formula 5
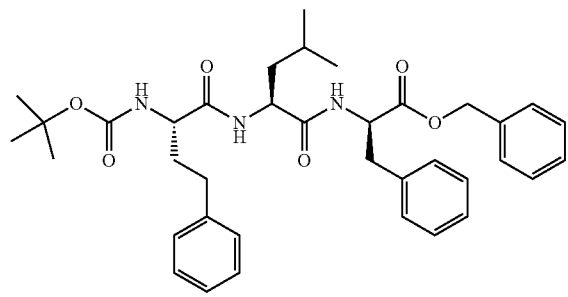
Formula 6
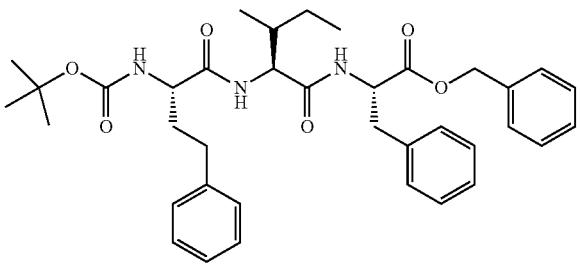
Formula 7
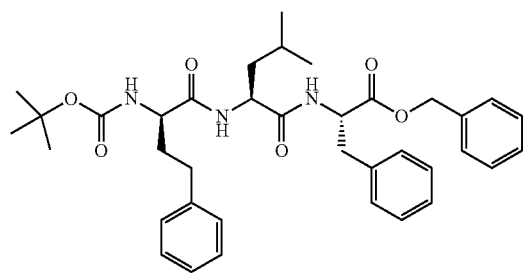
Formula 8
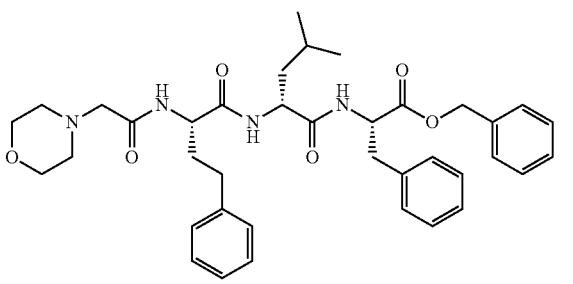
Formula 9
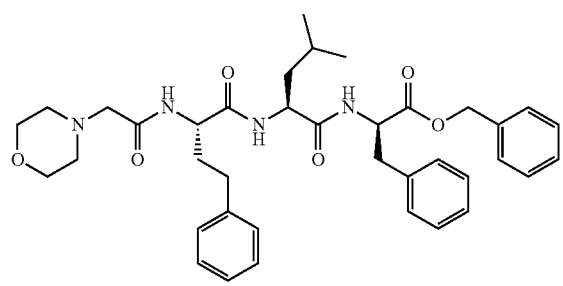
Formula 10
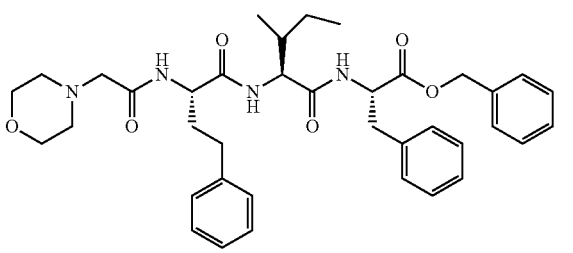
Formula 11
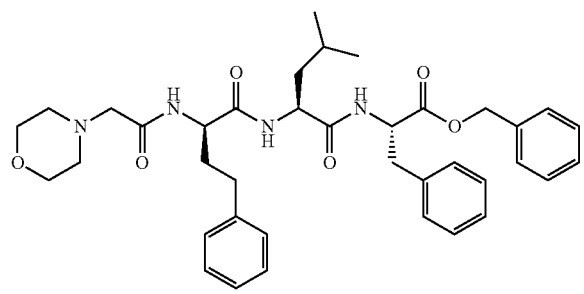
Formula 12
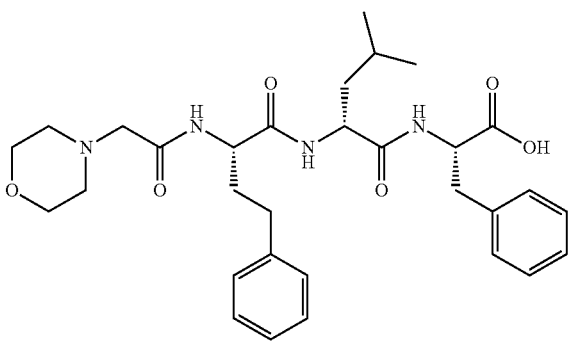

-continued
Formula 13
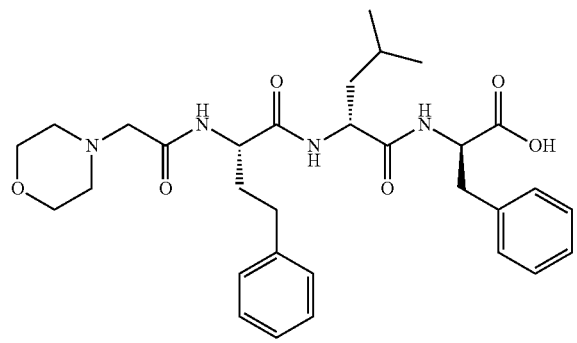
Formula 14
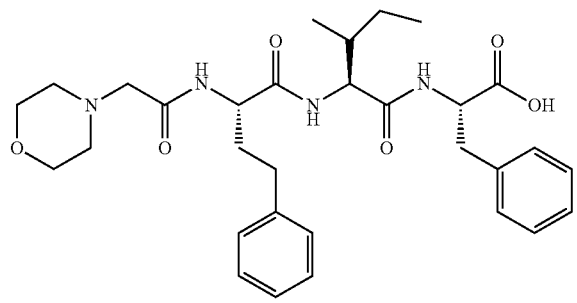
Formula 15
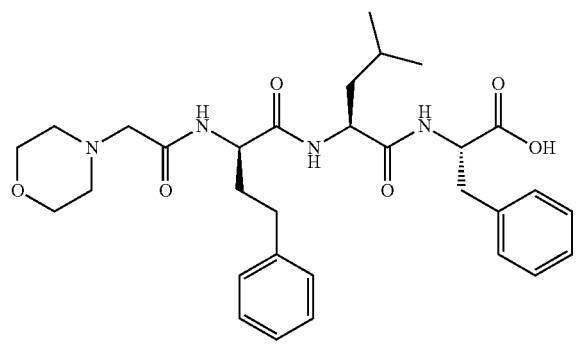
Formula 16
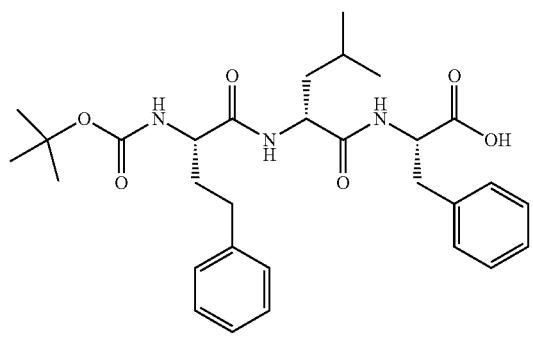
Formula 17
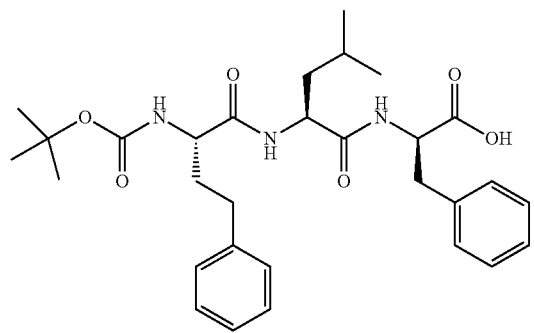
Formula 18
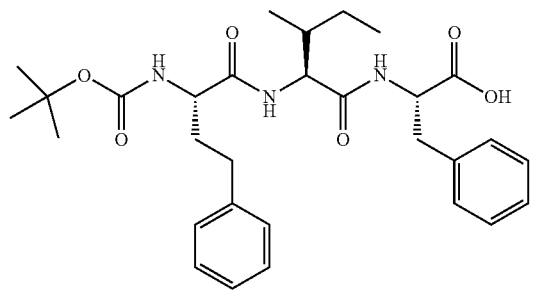
Formula 19
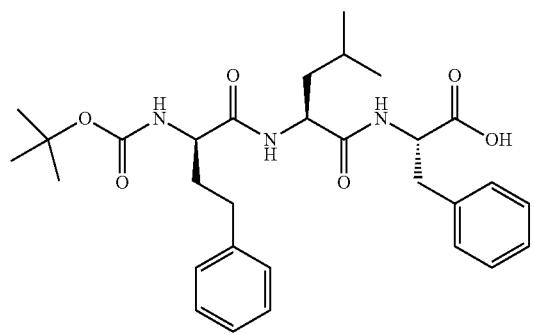
Formula 20
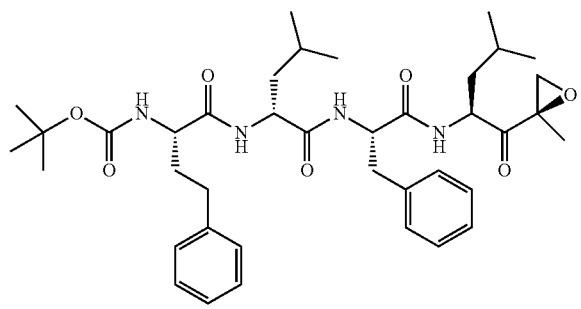

-continued
Formula 21
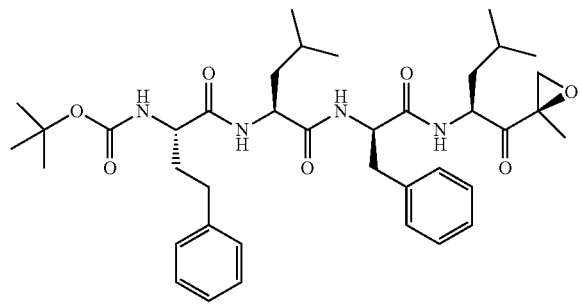
Formula 22
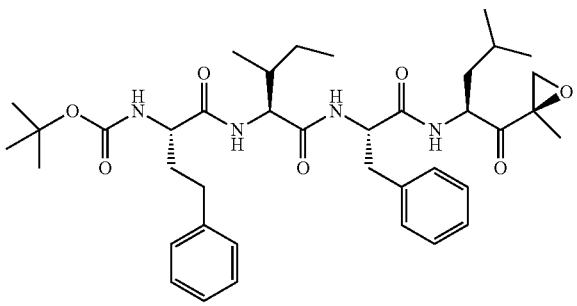
Formula 23
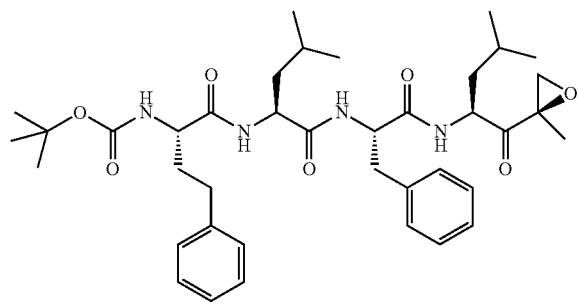
Formula 24
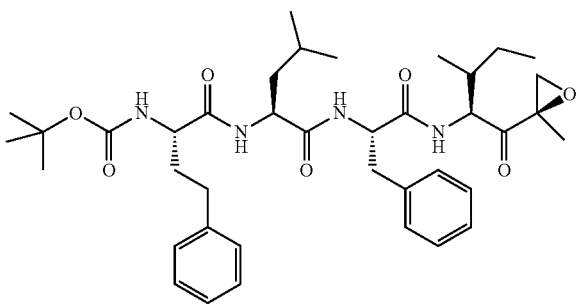
Formula 25
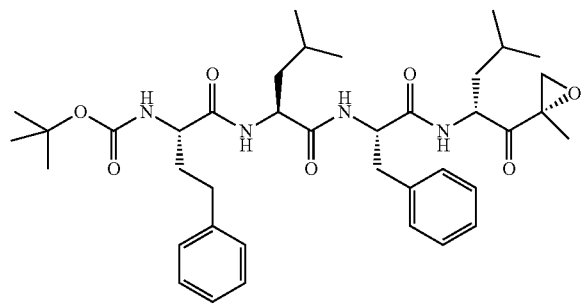
Formula 26
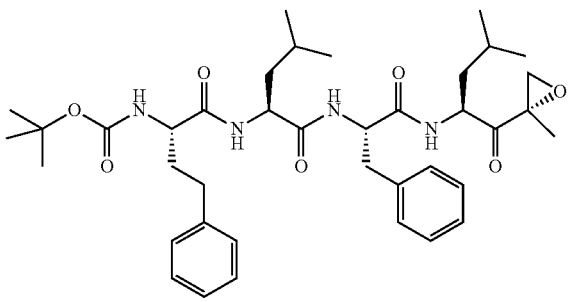
Formula 27
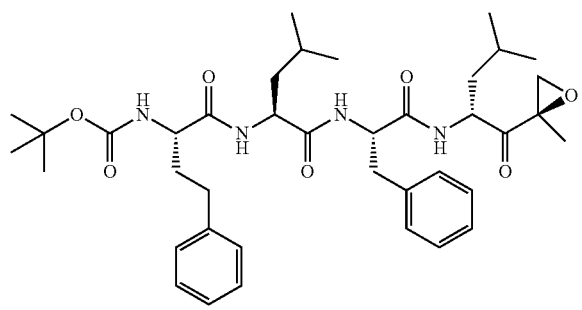
Formula 28
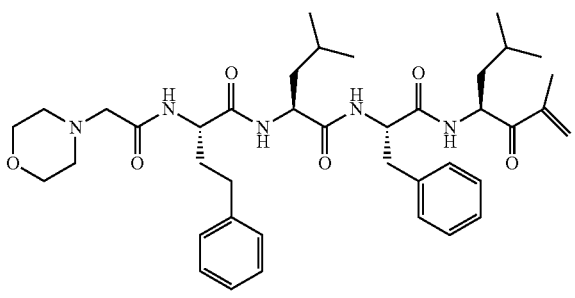
Formula 29
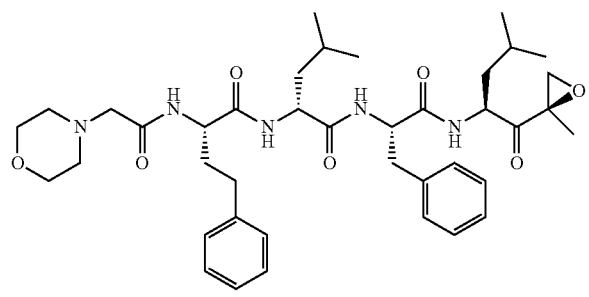
Formula 30
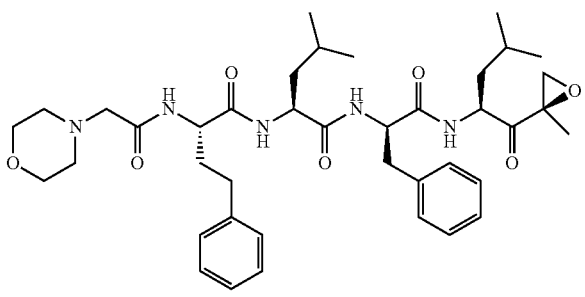

Formula 31
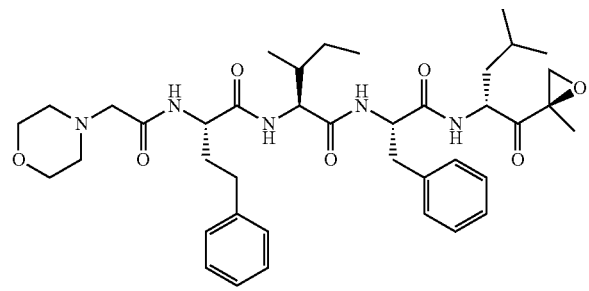
Formula 32
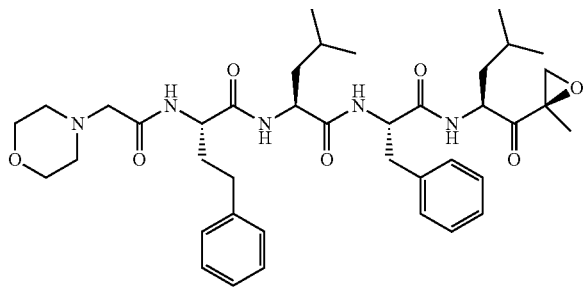
Formula 33
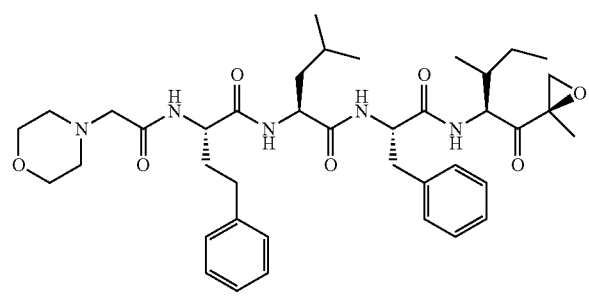
Formula 34
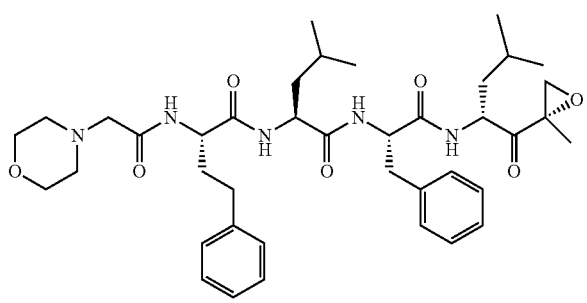
Formula 35
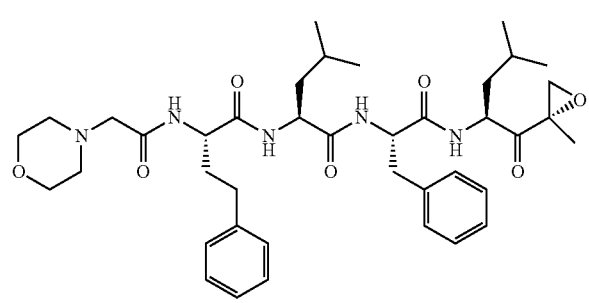
Formula 36
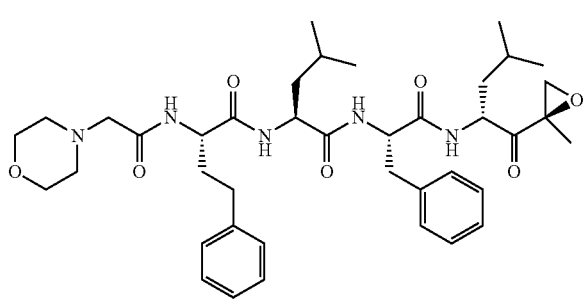
Formula 37
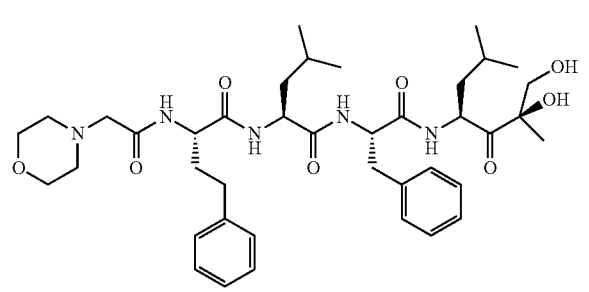
Formula 38
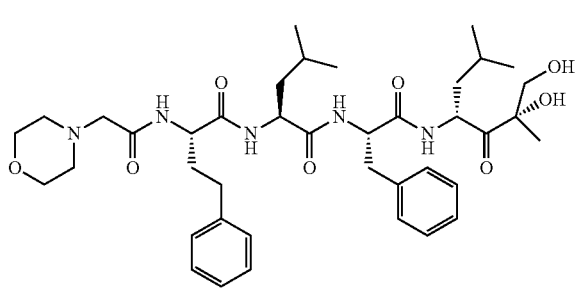
Formula 39
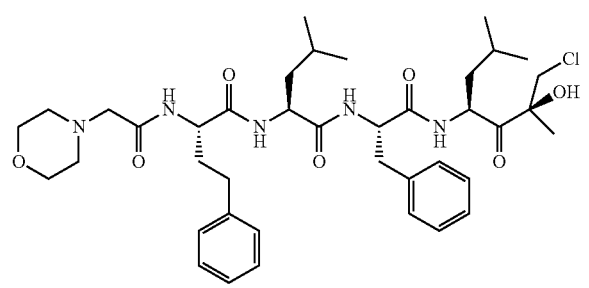
Formula 40
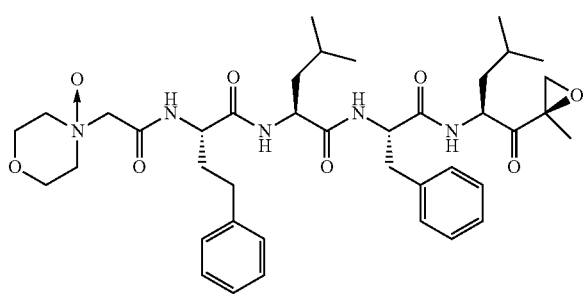

-continued

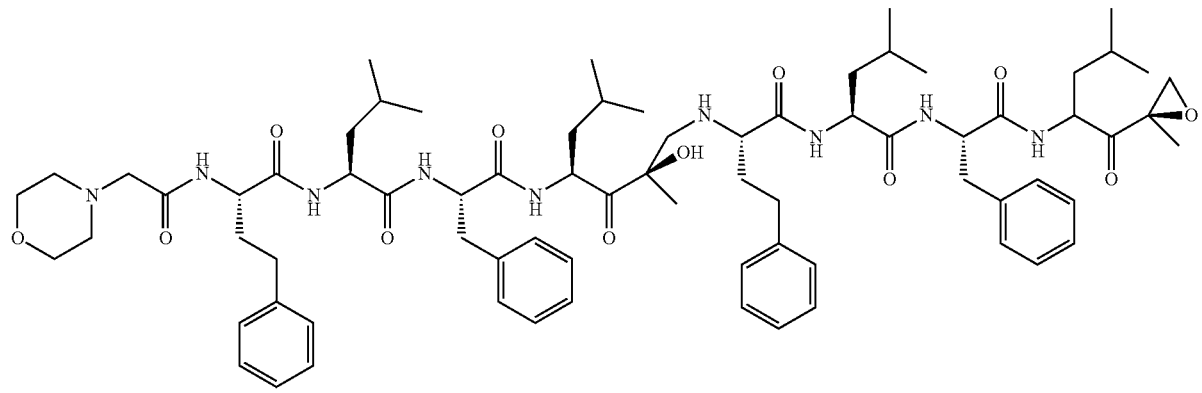

Formula 41

To overcome the difficulties associated with the processes described above, the inventors of the present invention have surprisingly found that use of less quantity of coupling agent and an additive substantially reduces the reaction time cycle, for instance about 3-6 hours against about overnight as reported thereby reduces the formation of by products for example tris(pyrrolidino phosphine) oxide, other process impurities and minimizing the contamination of un-reacted coupling agents such as HOBt, PyBOP. The present process also involves, the raw materials used for preparation of carfilzomib such as N-boc-L-leucine of Formula II, L-phenyl alanine benzyl ester of Formula III, N-boc-L-homophenylalanine of Formula VI and Formula IX are having less than 0.1% of its corresponding isomers thereby increasing the isomeric purity of carfilzomib by avoiding the formation of undesired carfilzomib isomers as an impurities.

Step a):

The step a) of the aforementioned process involves reaction of a compound of Formula II with a compound of Formula III or a salt thereof in presence of a coupling agent (C1), an additive (A1) and a base (B1) in a suitable solvent (S1) to obtain a compound of Formula IV.

In a preferred embodiment, the present invention provides an improved process for preparation of carfilzomib of Formula I or a pharmaceutically acceptable salt thereof, comprising: reacting a compound of Formula II with a compound of Formula III or a salt thereof in presence of a coupling agent (C1), an additive (A1) and a base (B1) in a suitable solvent (S1) to obtain a compound of Formula IV, wherein the coupling agent (C1) is used in an amount of about 0.9 to about 1.3 w/w mole equivalents per mole of Formula III; wherein the additive (A1) is used in catalytic amount of about 0.05 to about 0.5 w/w mole equivalents per mole of Formula III.

In a preferred embodiment, the N-boc-L-leucine of Formula II is having less than 0.1% of its corresponding D-isomer and isoleucine of Formula A and Formula B; the L-phenyl alanine benzyl ester of Formula III is having less than 0.1% by HPLC of its corresponding D-isomer of Formula C:

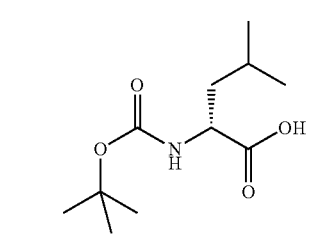

Formula A

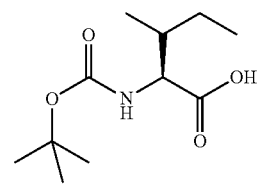

Formula B

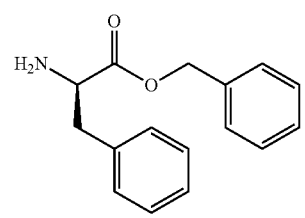

Formula C

The coupling agent (C1) used herein for reaction of compound of Formula II with a compound of Formula III or a salt thereof, preferably hydrochloride salt, is selected from the group consisting of benzotriazol-1-yl-oxytripyrrolidinophosphonium hexafluorophosphate (PyBOP), benzotriazol-1-yloxy-tris (dimethylamino)-phosphonium hexafluorophosphate (BOP), bromo-tripyrrolidino-phosphonium hexafluorophosphate (PyBrOP), Propylphosphonic anhydride (T3P), N-(3-dimethylaminopropyl)-N'-ethylcarbodiimide (EDC), 1,1'-Carbonyldiimidazole (CDI), diisopropylcarbodiimide (DCI), dicyclohexyl carbodiimide (DCC) and the like and mixture thereof; preferably benzotriazol-1-yl-oxytripyrrolidinophosphonium hexafluorophosphate (PyBOP).

The additive (A1) used herein for reaction of compound of Formula II with a compound of Formula III or a salt thereof, preferably hydrochloride salt, is selected from the group consisting of 1-Hydroxybenzotriazole (HOBt), 1-Hydroxy-7-aza-1H-benzotriazole (HOAt), 2-(1H-Benzotriazol-1-yl)-N,N,N',N'-tetramethylaminium tetrafluoroborate/ hexa fluoro phosphate (TBTU), 2-(7-Aza-1H-benzotriazol-1-yl)-N,N,N',N'-tetramethylaminium hexafluorophosphate) (HATU) and the like and mixture thereof; preferably 1-Hydroxybenzotriazole (HOBt).

In a preferred embodiment, the coupling agent (C1) used herein is benzotriazol-1-yl-oxytripyrrolidinophosphonium hexafluorophosphate (PyBOP) and is used in an amount of about 1.2 w/w mole equivalents per mole of Formula III; additive (A1) used herein is 1-hydroxybenzotriazole (HOBt) and is used in an amount of about 0.1 w/w mole equivalents per mole of Formula III.

Exemplary bases (B1) used herein for the reaction of compound of Formula II with a compound of Formula III or a salt thereof, preferably hydrochloride salt includes but are not limited to diisopropylethyl amine, Imidazole or its salts, 1,8-Diazabicyclo[5.4.0]undec-7-en (DBU), tertiary amines or its hydro halide salts thereof selected from the group consisting of triethyl amine-hydrochloride and the like and mixtures thereof; preferably diisopropylethyl amine.

The reaction of compound of Formula II with a compound of Formula III or a salt thereof, is advantageously carried out in a solvent (S1). Suitable solvent include, but are not limited to ethers, esters, halogenated hydrocarbons, amides, aromatic solvents, nitriles, or mixtures thereof. The ether includes, but are not limited to tetrahydrofuran, 2-methyltetrahydrofuran and the like; esters include, but are not limited to methyl acetate, ethyl acetate, propyl acetate, butyl acetate and the like; halogenated hydrocarbons include, but are not limited to methylene chloride, ethylene chloride, chloroform and the like; amides includes, but are not limited to dimethyl formamide, dimethyl acetamide, N-methyl pyrrolidinone and the like; aromatic solvents include, but are not limited to toluene, chlorobenzene and the like; nitriles include, but are not limited to acetonitrile, propionitrile, benzonitrile and the like and mixtures thereof; preferably dimethyl formamide.

The reaction temperature should be sufficient to effect the coupling reaction. Typically the reaction temperature can be from about −10° C. to about reflux temperature. Preferably the reaction temperature is about 25° C. to about 50° C. The reaction may take from about 0.5 hours to about 6 hours depending upon the coupling agent and additive, solvent and temperature chosen, preferably about 1 hour to 4 hours.

After completion of the reaction, the compound of Formula IV is advantageously isolated by quenching the step a) reaction mass in to water to precipitate compound of Formula IV as solid. The precipitated compound of Formula IV may be separated by methods known in the art, for example filtration.

The resultant product may optionally be further dried using conventional methods known in the art at a temperature ranging from about 40° C. to about 60° C. The compound of Formula IV, obtained by the aforementioned process have a chemical purity of at least about 95%, as measured by HPLC, preferably at least about 98%, as measured by HPLC and more preferably at least about 99.5%, as measured by HPLC; and contains less than 0.5% of total impurities, which include byproducts of HOBt, PyBOP, tris(pyrrolidino phosphine) oxide, isomer impurities of Formula 1, Formula 2 and Formula 3 as measured by HPLC; preferably less than 0.3%, as measured by HPLC.

In another embodiment, the obtained compound of Formula IV having less than 0.1%, as measured by HPLC of each of impurity of Formula 1, Formula 2 or Formula 3; preferably less than 0.05%, as measured by HPLC; more preferably less than 0.03%, as measured by HPLC.

In another embodiment, the compound of Formula IV obtained by the process described above is in amorphous in nature.

In another embodiment, the present invention provides amorphous compound of Formula IV characterized by a powder X-Ray diffraction (PXRD) pattern substantially in accordance with FIG. 1.

Step b):

The step b) of the aforementioned process involves deprotection of amine protecting group of Formula IV with a suitable acid to obtain a compound of Formula V or a salt thereof.

The suitable acid used herein for step b) is selected from the group consisting of hydrochloric acid, hydrobromic acid, sulfuric acid, phosphoric acid, acetic acid, trifluoro acetic acid, trichloro acetic acid, methane sulfonic acid and the like and mixture thereof; preferably trifluoro acetic acid.

The deprotection reaction of compound of Formula IV with a suitable acid can be carried out in a suitable organic solvent. The suitable organic solvent includes but is not limited to alcohols, ketones, ethers, halogenated hydrocarbons and mixtures thereof. The alcohols include, but are not limited to methanol, ethanol, isopropanol and the like; ketones include, but are not limited to acetone, methyl isobutyl ketone, methyl ethyl ketone and the like; ethers include, but are not limited to tetrahydrofuran, dimethyl ether, diisopropyl ether, methyl tertiary butyl ether, 1,4-dioxane and the like; halogenated hydrocarbons include, but are not limited to methylene chloride, ethylene chloride and the like and mixture thereof preferably methylene chloride.

The reaction can be carried out at a temperature of about 0° C. to reflux temperature; preferably at 0° C. to about 50° C. After completion of the reaction, the reaction mass can be basified with a suitable aqueous base such as sodium carbonate, potassium carbonate and the like and then extracting the product with water immiscible organic solvent such as ethyl acetate, methylene chloride and the like; preferably methylene chloride. The free base of compound of Formula V can be isolated from the resultant water immiscible organic solvent by subjecting to evaporation under vacuum.

Step c):

The step c) of the aforementioned process involves reaction of the compound of Formula V or a salt thereof; preferably free base, with a compound of Formula VI in presence of a coupling agent (C2), an additive (A2) and a base (B2) in a suitable solvent (S2) to obtain a compound of Formula VII.

In a preferred embodiment, the present invention provides an improved process for preparation of carfilzomib of Formula I or a pharmaceutically acceptable salt thereof, comprising: reacting a compound of Formula V with a compound of Formula VI in presence of a coupling agent (C2), an additive (A2) and a base (B2) in a suitable solvent (S2) to obtain a compound of Formula VII, wherein the coupling agent (C2) is used in an amount of about 0.9 to about 1.3 w/w mole equivalents per mole of Formula IV; wherein the additive (A2) is used in catalytic amount of about 0.05 to about 0.5 w/w mole equivalents per mole of Formula IV.

In a preferred embodiment, the N-boc-L-homophenylalanine of Formula VI is having less than 0.1% of its corresponding D-isomer of Formula D:

Formula D

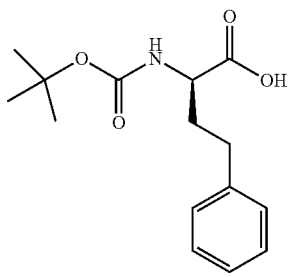

The coupling agent (C2), an additive (A2), base (B2) and solvent (S2) are used herein for reaction of compound of Formula V with a compound of Formula VI is same as used for step a) as mentioned above.

In a preferred embodiment, the coupling agent (C2) used herein is benzotriazol-1-yl-oxytripyrrolidinophosphonium hexafluorophosphate (PyBOP) and is used in an amount of about 1.2 w/w mole equivalents per mole of Formula IV; additive (A2) used herein is 1-Hydroxybenzotriazole (HOBt) and is used in an amount of about 0.1 w/w mole equivalents per mole of Formula IV.

The reaction temperature should be sufficient to effect coupling reaction. Typically the reaction temperature is from about −10° C. to about reflux temperature. Preferably the reaction temperature is about 25° C. to about 50° C. The reaction may take from about 0.5 hours to about 6 hours depending upon the coupling agent and additive, solvent and temperature chosen, preferably about 1 hour to 4 hours.

After completion of the reaction, the compound of Formula VII is advantageously isolated by quenching the step c) reaction mass in to water to precipitate compound of Formula IV as solid. The precipitated compound of Formula VII can be separated by methods known in the art, for example filtration.

The resultant product may optionally be dried using conventional methods at a temperature ranging from about 40° C. to about 60° C. The compound of Formula VII, obtained by the aforementioned process, have a chemical purity of at least about 95%, as measured by HPLC, preferably at least about 98%, as measured by HPLC and more preferably at least about 99.5%, as measured by HPLC; and contains less than 0.5% of total impurities, which include byproducts HOBt, PyBOP, tris(pyrrolidino phosphine) oxide, isomeric impurities of Formula 4, Formula 5, Formula 6 and Formula 7 as measured by HPLC; preferably less than 0.3%, as measured by HPLC.

In another embodiment, the obtained compound of Formula VII having less than 0.1%, as measured by HPLC of each of impurity of Formula 4, Formula 5, Formula 6 or Formula 7; preferably less than 0.05%, as measured by HPLC; more preferably less than 0.03%, as measured by HPLC.

In another embodiment, the compound of Formula VII obtained by the process described above is in amorphous in nature.

Figure 2:
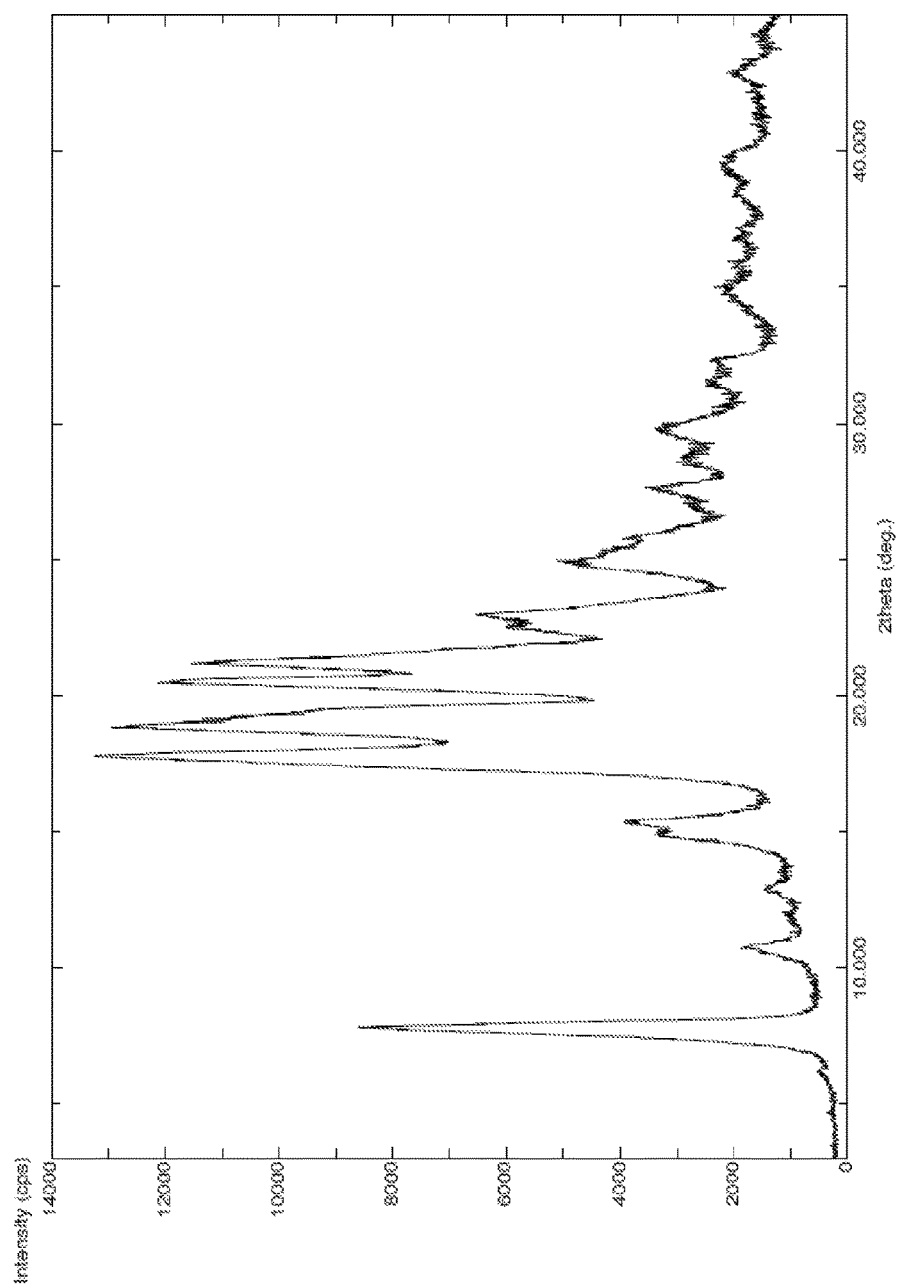
FIG. 2 is the characteristic powder X-ray diffraction (XRD) pattern of amorphous compound of Formula VII.

In another embodiment, the present invention provides amorphous compound of Formula VII characterized by a powder X-Ray diffraction (PXRD) pattern substantially in accordance with FIG. 2.

Step d):

The step d) of the aforementioned process involves deprotection of benzyl protecting group of the compound of Formula VII in presence of a suitable deprotecting agent to obtain a compound of Formula VIII.

The suitable deprotecting agent used herein for deprotection of the compound of Formula VII is include, but is not limited to palladium on carbon/ammonium formate, palladium on carbon/ammonium acetate, palladium on carbon/hydrogen gas, palladium hydroxide/hydrogen gas, raney nickel/hydrogen gas, platinum oxide/hydrogen gas, zinc/hydrogen gas and the like; preferably palladium on carbon/hydrogen gas.

The deprotection may be carried out in a suitable solvent, which include alcohols, esters, ethers, halogenated hydrocarbons, acetic acid, water and mixtures thereof. The alcohols include, but are not limited to methanol, ethanol, isopropanol and the like; esters include, but are not limited to methyl acetate, ethyl acetate, propyl acetate, butyl acetate and the like; ethers include, but are not limited to tetrahydrofuran and the like; halogenated hydrocarbons include, but are not limited to methylene chloride, ethylene chloride and the like, and water and mixture thereof; preferably a mixture of methanol and methylene chloride.

The deprotection reaction may be carried out at a temperature of about 0° C. to reflux temperature; preferably at 0° C. to about 50° C. After completion of the reaction, the reaction mass may be filtered and resulting compound of Formula VIII may be isolated by subjecting the filtrate to evaporation under vacuum to obtain a residue. Optionally the obtained residue is treated with a suitable solvent such as n-heptane and stirred for about 2 hours and the resultant compound of Formula VIII may be isolated by techniques known in the art, for example filtration.

Optionally resulting Formula VIII may be purified by dissolving in a suitable organic solvent such as ethyl acetate, methylene chloride, 2-methyl tetrahydrofuran at a temperature of about 0° C. to reflux temperature; preferably at 25° C. to about 50° C. The pure compound of Formula VIII may be precipitated from the solution by either addition of suitable anti-solvent to the Formula VIII solution obtained as above, (or) addition of Formula VIII solution obtained as above into a suitable anti-solvent at a temperature of less than about 25° C. The suitable anti-solvent include, but are not limited to dimethyl ether, diethyl ether, diisopropyl ether, hexane, heptane, propane, cyclopropane, cyclobutane, cyclopentane, cyclohexane, methyl cyclohexane, cycloheptane, cyclooctane and the like and mixture thereof; preferably Formula VIII is dissolved in ethyl acetate and precipitated by adding in to antisolvent of heptane and the resultant compound of Formula VIII may be isolated by techniques known in the art, for example filtration.

The resultant product may optionally be further dried by the known techniques at a temperature ranging from about 40° C. to about 60° C. The resulting Formula VIII, obtained by the aforementioned process, have a chemical purity of at least about 95%, as measured by HPLC, preferably at least about 98%, as measured by HPLC and more preferably at least about 99.0%, as measured by HPLC; and having less than 0.1%, as measured by HPLC of each of impurity of Formula 16, Formula 17, Formula 18 or Formula 19; preferably less than 0.05%, as measured by HPLC; more preferably less than 0.03%, as measured by HPLC.

In another embodiment, the obtained compound of Formula VIII having less than 0.1%, as measured by HPLC of each of impurity of Formula 16, Formula 17, Formula 18 or Formula 19; preferably less than 0.05%, as measured by HPLC; more preferably less than 0.03%, as measured by HPLC.

In another embodiment, the compound of Formula VIII obtained by the process described above is in an amorphous nature.

Figure 3:
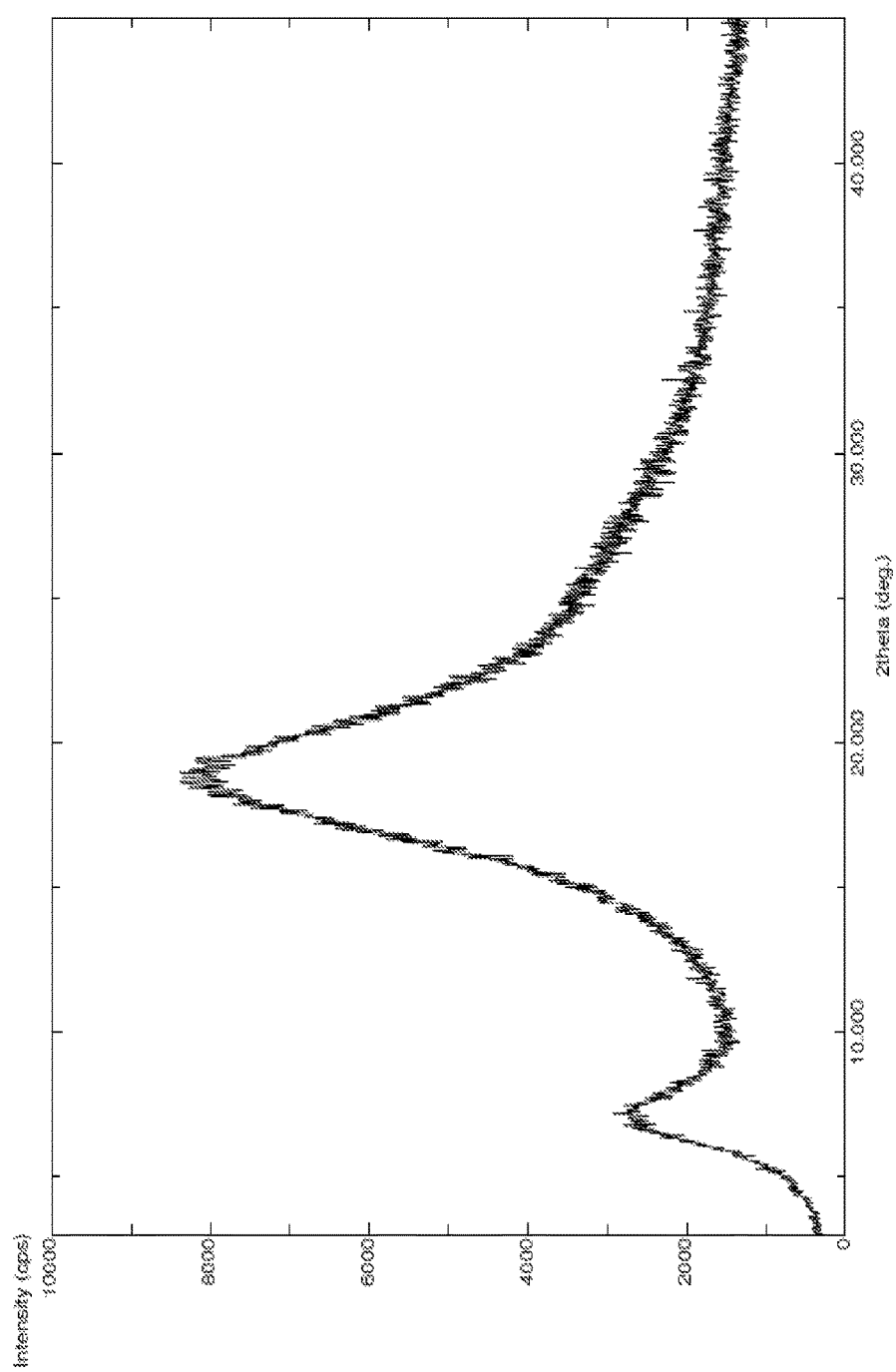
FIG. 3 is the characteristic powder X-ray diffraction (XRD) pattern of amorphous compound of Formula VIII.

In another embodiment, the present invention provides amorphous compound of Formula VIII characterized by a powder X-Ray diffraction (PXRD) pattern substantially in accordance with FIG. 3.

Step e):

The step e) of the aforementioned process involves reaction of the compound of Formula VIII with a compound of Formula IX or a salt thereof in presence of a coupling agent (C3), an additive (A3) and a base (B3) in a suitable solvent (S3) to obtain a compound of Formula X.

In a preferred embodiment, the present invention provides an improved process for preparation of carfilzomib of Formula I or a pharmaceutically acceptable salt thereof, comprising: reacting a compound of Formula VIII with a compound of Formula IX or a salt thereof in presence of a coupling agent (C3), an additive (A3) and a base (B3) in a suitable solvent (S3) to obtain a compound of Formula X; wherein the coupling agent (C3) is used in an amount of about 0.9 to about 1.3 w/w mole equivalents per mole of Formula VIII; wherein the additive (A3) is used in catalytic amount of about 0.05 to about 0.5 w/w mole equivalents per mole of Formula VIII.

In a preferred embodiment, the compound of Formula IX having less than 0.1% of its corresponding isomers or its impurities of Formula E, Formula F, Formula G, Formula H, Formula I and Formula J:

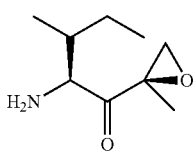

Formula E

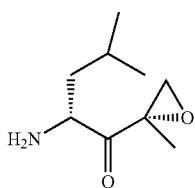

Formula F

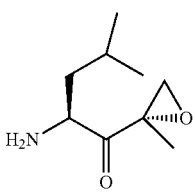

Formula G

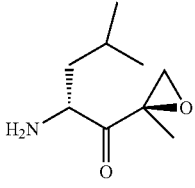

Formula H

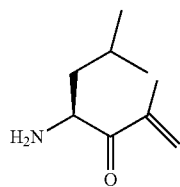

Formula I

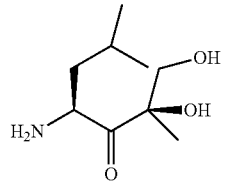

Formula J

The coupling agent (C3), an additive (A3), base (B3) and solvent (S3) are used herein for reaction of compound of Formula VIII with a compound of Formula IX or a salt thereof; preferably free base, is same as used for step a) as mentioned above.

In a preferred embodiment, the coupling agent (C3) used herein is benzotriazol-1-yl-oxytripyrrolidinophosphonium hexafluorophosphate (PyBOP) and is used in an amount of about 1.2 w/w mole equivalents per mole of Formula VIII; additive (A3) used herein is 1-Hydroxybenzotriazole (HOBt) and is used in an amount of about 0.1 w/w mole equivalents per mole of Formula VIII.

The reaction temperature should be sufficient to effect coupling reaction. Typically the reaction temperature is from about −10° C. to about reflux temperature. Preferably the reaction temperature is about 25° C. to about 50° C. The reaction may take from about 0.5 hours to about 6 hours depending upon the coupling agent and additive, solvent and temperature chosen, preferably about 1 hour to 4 hours.

After completion of the reaction, the compound of Formula X is advantageously isolated by quenching the step e) reaction mass in to water to precipitate compound of Formula X as solid. The precipitated compound of Formula X may be separated by methods known in the art, for example filtration.

The present invention provides a compound of Formula X prepared by the process described as above having a purity of at least about 90%, as measured by HPLC, preferably at least about 95% as measured by HPLC, and more preferably at least about 97.0%, as measured by HPLC; and contains less than 3% of total impurities, which includes byproducts of HOBt, PyBOP, tris(pyrrolidino phosphine) oxide; isomeric impurities of Formula 20, Formula 21, Formula 22, Formula 23, Formula 24, Formula 25, Formula 26 or Formula 27 as measured by HPLC.

In another embodiment, the compound of Formula X thus obtained may be purified by treating the compound of Formula X in a suitable solvent.

In accordance with another embodiment, the present invention provides a process for purification of compound of Formula X, comprising:
 a) dissolving compound of Formula X in one or more suitable solvent at a temperature of about 30° C. to about reflux temperature,
 b) cooling the obtained solution to less than 10° C., and
 c) filtering the compound of Formula X.

The one or more suitable solvent used herein for purification of compound of Formula X include but is not limited to alcohols, esters, ethers, nitriles, ketones, halogenated hydrocarbons and mixtures thereof. The alcohols include, but are not limited to methanol, ethanol, isopropanol, n-propanol, t-butanol and the like; esters include, but are not limited to methyl acetate, ethyl acetate, isopropyl acetate and the like; ethers include, but are not limited to tetrahydrofuran, 2-methyltetrahydrofuran and the like; nitriles include, but are not limited to acetonitrile, propionitrile and the like; ketones include, but are not limited to acetone, methyl ethyl ketone, methyl isobutyl ketone and the like; halogenated hydrocarbons include, but are not limited to methylene chloride and the like and mixtures thereof; preferably ethyl acetate.

The solution may be heated to dissolve the compound of Formula X. The temperature suitable for dissolving compound of Formula X depends on the solvent used and the amount of compound of Formula X in the solution. Typically, the solution is heated at a temperature of at least about 30° C. to about reflux; preferably at 50° C. to about 80° C. The resultant reaction solution may be cooled at a temperature from about 10° C. or less such that the compound of Formula X can be isolated by conventional techniques, for example filtration.

The present invention provides a compound of Formula X prepared by the purification as described above having a purity of at least about 97%, as measured by HPLC, preferably at least about 98% as measured by HPLC, and more preferably at least about 99.5%, as measured by HPLC; and contains less than 0.5% of total impurities, which include byproducts of HOBt, PyBOP, tris(pyrrolidino phosphine) oxide; isomeric impurities of Formula 20, Formula 21, Formula 22, Formula 23, Formula 24, Formula 25, Formula 26 or Formula 27 as measured by HPLC; preferably less than 0.3%, as measured by HPLC.

In another embodiment, the obtained compound of Formula X having less than 0.1%, as measured by HPLC of each of impurity of Formula 20, Formula 21, Formula 22, Formula 23, Formula 24, Formula 25, Formula 26 or Formula 27; preferably less than 0.05%, as measured by HPLC; more preferably less than 0.03%, as measured by HPLC.

Step f):

The step f) of the aforementioned process involves deprotection of amine protecting group of Formula X with a suitable acid to obtain a compound of Formula XI or a salt thereof is may be carried out in a suitable organic solvent.

The suitable acid and suitable organic solvent are used herein for deprotection of amine protecting group of Formula X is same as used for step b) as mentioned above.

The deprotection reaction may be carried out at a temperature of about 0° C. to reflux temperature; preferably at 0° C. to about 50° C. After completion of the reaction, the reaction mass may be basified with a suitable aqueous base such as sodium carbonate, potassium carbonate and the like and then extracting the product with water immiscible organic solvent such as ethyl acetate, methylene chloride and the like. The free base of compound of Formula XI may be isolated from the resultant water immiscible organic solvent by subjecting to evaporation under vacuum; or the reaction mass may be isolated as solid compound preferably by directly evaporating the acid salt of compound of Formula XI containing reaction solution to obtain solid acid salt of compound of Formula XI.

In a preferred embodiment, the compound of Formula XI is isolated as trifluoro acetic salt and is in an amorphous in nature.

In another embodiment, the present invention provides amorphous Form of trifluoro acetic acid salt of Formula XI.

Figure 5:
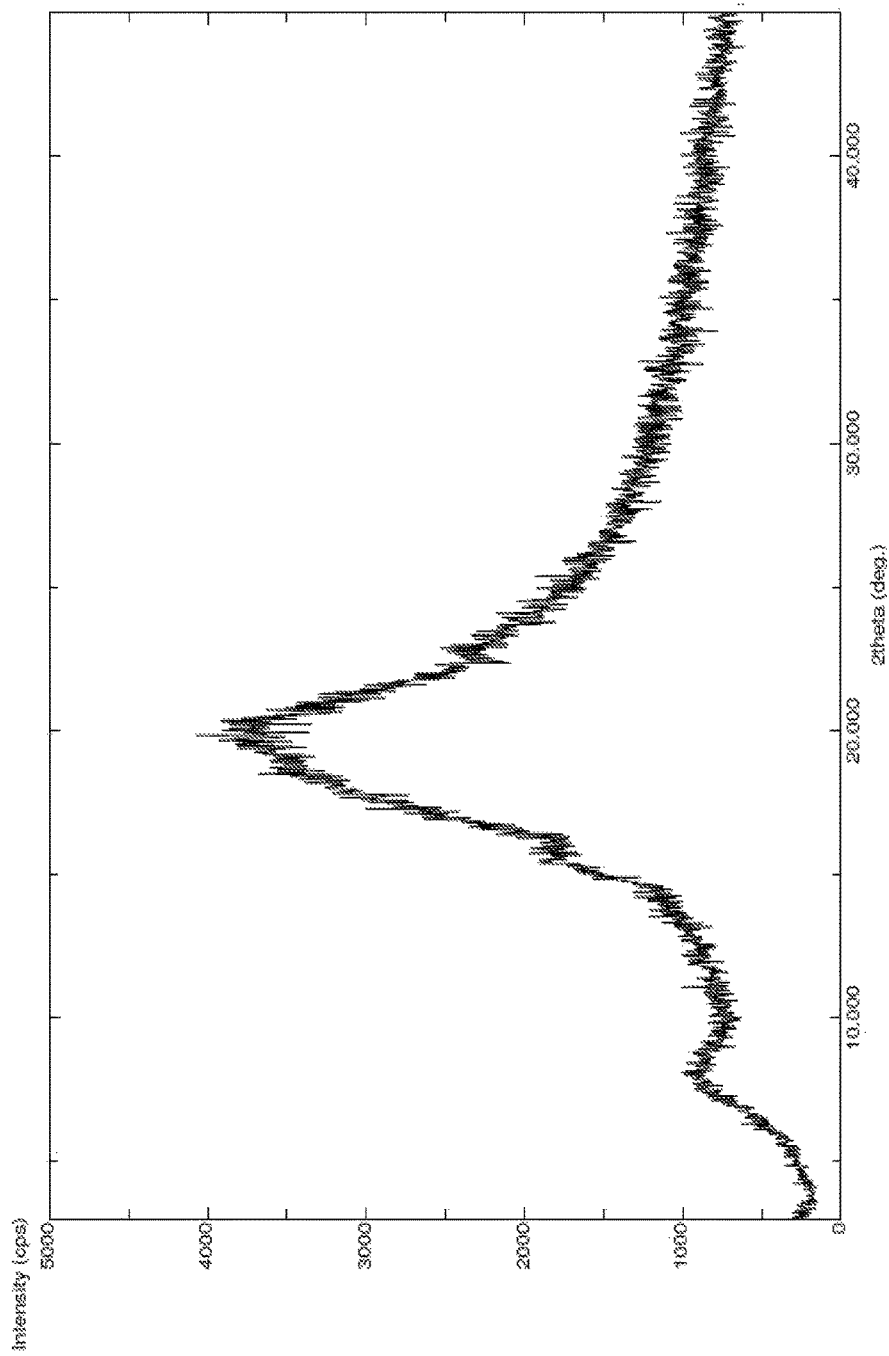
FIG. 5 is the characteristic powder X-ray diffraction (XRD) pattern of amorphous compound of Formula XI trifluoro acetic acid salt.

In another embodiment, the present invention provides amorphous Form of trifluoro acetic acid salt of Formula XI characterized by a powder X-Ray diffraction (PXRD) pattern substantially in accordance with FIG. 5.

In a preferred embodiment, the compound of Formula XI is isolated as its free base and is in amorphous in nature.

In another embodiment, the present invention provides amorphous form of Formula XI free amine.

Figure 6:
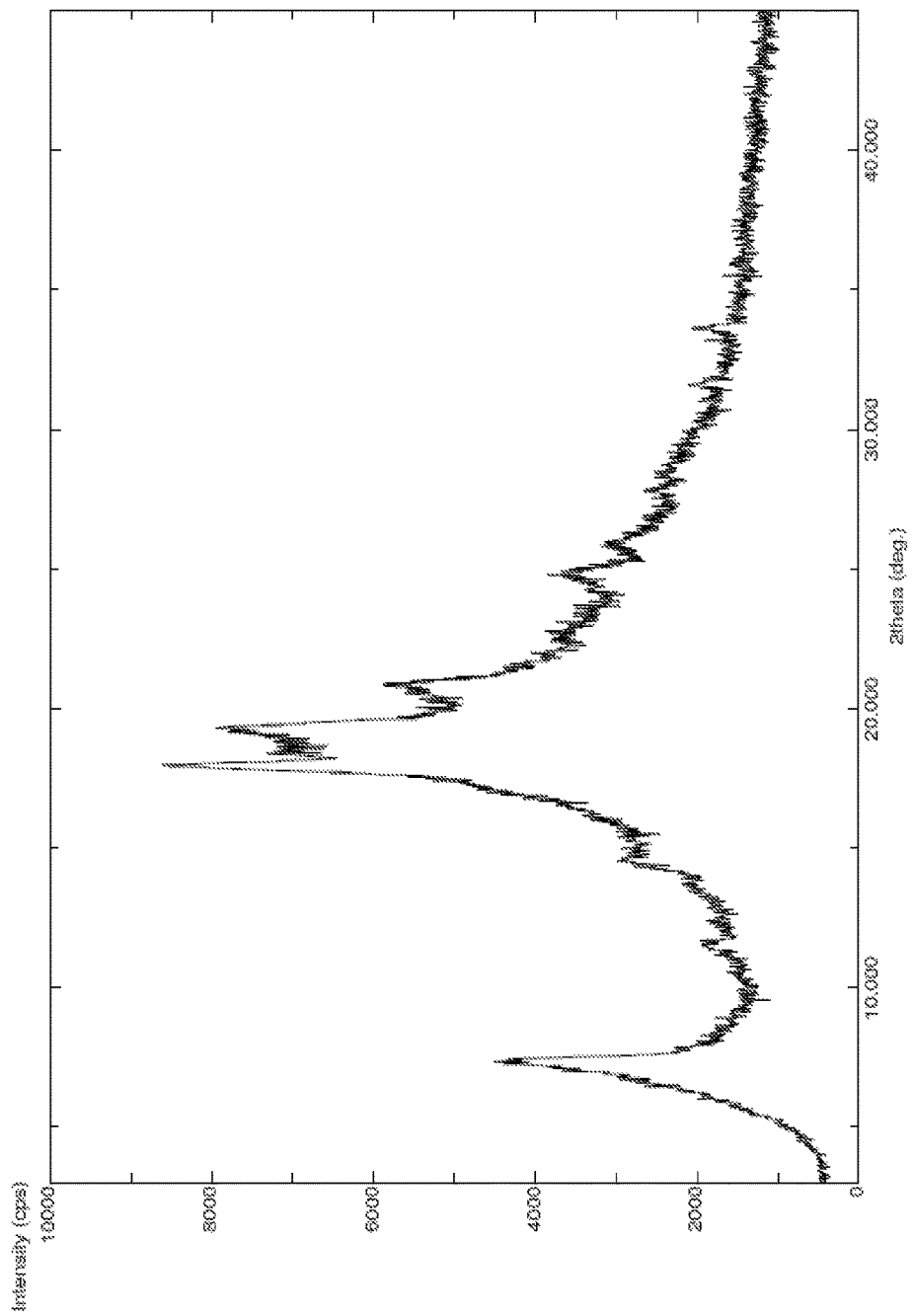
FIG. 6 is the characteristic powder X-ray diffraction (XRD) pattern of amorphous compound of Formula XI free amine.

In another embodiment, the present invention provides amorphous Form of Formula XI free amine characterized by a powder X-Ray diffraction (PXRD) pattern substantially in accordance with FIG. 6.

Step g):

The step g) of the aforementioned process involves reaction of compound of Formula XI or a salt thereof with a compound of Formula XII or a salt thereof in presence of a coupling agent (C4), an additive (A4) and a base (B4) in a suitable solvent (S4) to obtain carfilzomib of Formula I.

In a preferred embodiment, the present invention provides an improved process for preparation of carfilzomib of Formula I or a pharmaceutically acceptable salt thereof, comprising: reacting a compound of Formula XI or a salt thereof with a compound of Formula XII or a salt thereof in presence of a coupling agent (C4), an additive (A4) and a base (B4) in a suitable solvent (S4) to obtain carfilzomib or a pharmaceutically acceptable salt thereof; wherein the coupling agent (C4) is used in an amount of about 0.9 to about 1.3 w/w mole equivalents per mole of Formula X; wherein the additive (A4) is used in catalytic amount of about 0.05 to about 0.5 w/w mole equivalents per mole of Formula X.

The coupling agent (C4), an additive (A4), base (B4) and solvent (S4) are used herein for reaction of compound of Formula XI or a salt thereof, preferably free base with a compound of Formula XII or a salt thereof; preferably hydrochloride salt, is same as used for step a) as mentioned above.

In a preferred embodiment, the coupling agent (C4) used herein is benzotriazol-1-yl-oxytripyrrolidinophosphonium hexafluorophosphate (PyBOP) and is used in an amount of about 1.2 w/w mole equivalents per mole of Formula X; additive (A4) used herein is 1-Hydroxybenzotriazole (HOBt) and is used in an amount of about 0.1 w/w mole equivalents per mole of Formula X.

The reaction temperature should be sufficient to effect coupling reaction. Typically the reaction temperature may be from about −10° C. to about reflux temperature. Preferably the reaction temperature is about 25° C. to about 50° C. The reaction may take from about 0.5 hours to about 6 hours depending upon the coupling agent and additive, solvent and temperature chosen, preferably about 1 hour to 4 hours.

After completion of the reaction, the carfilzomib of Formula I is isolated by quenching the step g) reaction mass in to water to precipitate carfilzomib as solid. The precipitated carfilzomib of Formula I may be separated by methods known in the art, for example filtration.

The present invention provides carfilzomib prepared by the process described as above having a purity of at least about 98%, as measured by HPLC, preferably at least about 99% as measured by HPLC.

Alternatively, the resultant carfilzomib of Formula I can be converted in to its pharmaceutically acceptable salt thereof.

The present inventors have surprisingly found that, isolation of carfilzomib as its pharmaceutically acceptable salt thereof enhances purity by removing the impurities formed during the preparation and isomer impurities, if any.

In another embodiment, the present invention provides a process for purification of carfilzomib, comprising:
- a) providing a solution of carfilzomib in one or more organic solvents,
- b) adding maleic acid to the step a) solution,
- c) isolating the carfilzomib maleic acid salt,
- d) neutralizing the carfilzomib maleic acid salt in a suitable solvent using a base,
- e) concentrating the step d) solution under vacuum to obtain a residue,
- f) dissolving the step e) residue in a suitable solvent,
- g) adding the step f) solution to an anti-solvent, or vice-versa, and
- h) isolating the pure carfilzomib.

The one or more organic solvents for providing a solution of carfilzomib include, but are not limited to alcohols, esters, ethers, nitriles, halogenated solvents and mixtures thereof. The alcohols includes, but are not limited to methanol, ethanol, isopropanol and the like; esters such as methyl acetate, ethyl acetate, isopropyl acetate and the like; ethers such as tetrahydrofuran, methyl tertiary butyl ether and the like; nitriles such as acetonitrile, propionitrile and the like; halogenated solvents such as methylene chloride, chloroform and the like and mixture thereof preferable a mixture of acetonitrile and tetrahydrofuran.

The suitable temperature for dissolving carfilzomib includes a temperature of about 25° C. to reflux; preferably at about 25° C. to about 35° C.

Then the crystalline carfilzomib maleate salt can be recovered by any conventional techniques known in the art, for example filtration. Typically, if stirring is involved, the temperature during stirring can range from about 25° C. to about 35° C. and the resultant product may optionally be further dried. Drying can be suitably carried out in a tray dryer, vacuum oven, air oven and the like. The drying can be carried out at a temperature ranging from about 40° C. to about 60° C. A high purity level of the resulting carfilzomib, obtained by the aforementioned process, may have a chemical purity of at least about 98%, as measured by HPLC, preferably at least about 99%, as measured by HPLC and more preferably at least about 99.9%, as measured by HPLC and contains less than 0.1%, as measured by HPLC of each of impurity of Formula 28, Formula 29, Formula 30, Formula 31, Formula 32, Formula 33, Formula 34, Formula 35, Formula 36, Formula 37, Formula 38, Formula 39, Formula 40 or Formula 41; preferably less than 0.05%, as measured by HPLC; more preferably less than 0.03%, as measured by HPLC.

The step of neutralizing the carfilzomib maleic acid salt involves treating the carfilzomib maleic acid salt with a suitable base, where in the base includes but are not limited to sodium carbonate, potassium carbonate, sodium bicarbonate, potassium bicarbonate, ammonium hydroxide and mixtures thereof; preferably sodium bicarbonate.

The step of neutralizing the carfilzomib maleic acid salt may be carried out in a suitable solvent. The suitable solvent includes but is not limited to esters, halogenated solvents, aromatic hydrocarbons and mixtures thereof. The esters such as methyl acetate, ethyl acetate, isopropyl acetate and the like; halogenated solvents such as methylene chloride, chloroform and the like; aromatic hydrocarbons include, but are not limited to toluene, xylene and the like, water and mixture thereof; preferable methylene chloride, water or mixtures thereof.

Then the product containing organic layer may be separated and followed by concentrating under vacuum at a temperature of about 25° C. to about 65° C.; preferably at about 30° C. to about 45° C. to obtain carfilzomib as a residue.

The residue so obtained is dissolved in a suitable solvent to obtain a solution at a suitable temperature. Typically, the solution is heated at a temperature of at least about 30° C. to about reflux temperature, wherein the suitable solvent includes, but are not limited to alcohols such as methanol, ethanol, isopropanol, n-propanol, n-butanol, t-butanol and the like and mixtures thereof preferably methanol. The carfilzomib may be precipitated by adding the step f) solution to an anti-solvent of water at a temperature of about 0° C. to about 35° C.; preferably at less than 10° C.

The carfilzomib can be recovered by any conventional techniques known in the art, for example filtration. Typically, if stirring is involved, the temperature during stirring can range from about 0° C. to about 30° C., preferably at less than 10° C. and the resultant product may optionally be further dried. Drying can be suitably carried out in a tray dryer, vacuum oven, air oven and the like. The drying can be carried out at a temperature ranging from about 35° C. to about 60° C. A high purity level of the resulting amorphous carfilzomib, obtained by the aforementioned process, may have a chemical purity of at least about 98%, as measured by HPLC, preferably at least about 99%, as measured by HPLC and more preferably at least about 99.9%, as measured by HPLC and contains less than 0.1%, as measured by HPLC of each of impurity of Formula 28, Formula 29, Formula 30, Formula 31, Formula 32, Formula 33, Formula 34, Formula 35, Formula 36, Formula 37, Formula 38, Formula 39, Formula 40 or Formula 41; preferably less than 0.05%, as measured by HPLC; more preferably less than 0.03%, as measured by HPLC.

Carfilzomib recovered using the purification process of the present invention is in substantially amorphous form.

In another embodiment, the present invention provides carfilzomib obtained by the aforementioned process, containing less than 0.05% as measured by HPLC of one or more of impurities of Formula 1 to Formula 41; preferably 0.03% as measured by HPLC.

In another embodiment, the present invention provides carfilzomib maleate salt.

In another embodiment, the present invention provides crystalline carfilzomib maleate salt.

Figure 7:
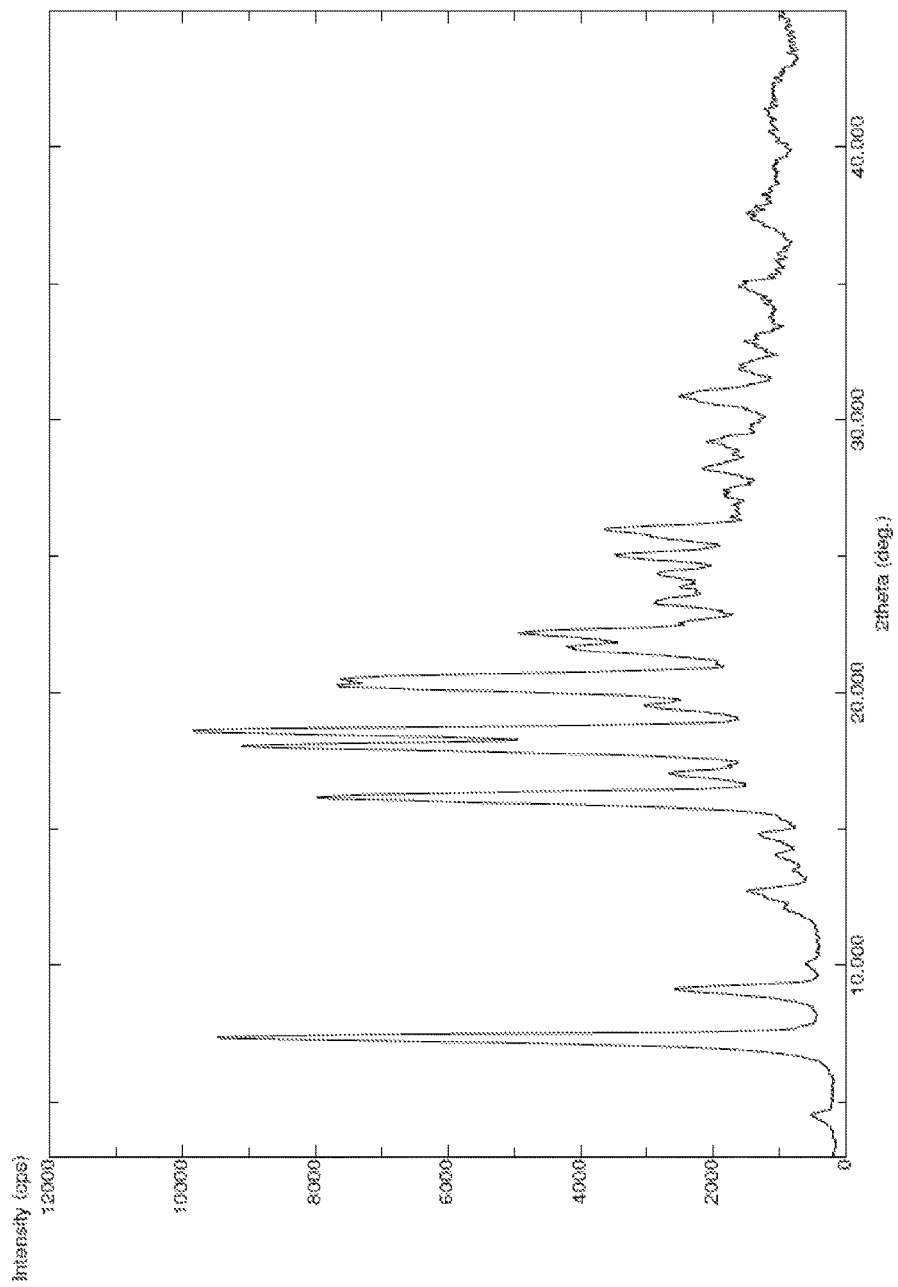
FIG. 7 is the characteristic powder X-ray diffraction (XRD) pattern of crystalline carfilzomib maleate salt.

In another embodiment, the present invention provides crystalline carfilzomib maleate salt characterized by a powder X-Ray diffraction (PXRD) pattern substantially in accordance with FIG. 7.

In another embodiment, the present invention provides a process for preparation of amorphous Form of carfilzomib, comprising:
- a) providing a solution of carfilzomib pharmaceutically acceptable salt in a suitable solvent,
- b) neutralizing the step a) solution with a base,
- c) concentrating the step b) solution under vacuum to obtain a residue,
- d) dissolving the step c) residue in a suitable solvent,
- e) adding the step d) solution to an anti-solvent, or vice-versa, and
- f) isolating the amorphous form of carfilzomib.

Any form of carfilzomib salt or a solution of carfilzomib salt obtained from previous processing steps can be used as starting material in the process of making the amorphous carfilzomib of the present invention.

The carfilzomib salt used to prepare carfilzomib amorphous form is any salt of carfilzomib; preferably maleate salt of carfilzomib.

The step a) process involves providing a solution of maleate salt of carfilzomib in a suitable solvent at a temperature of about 25° C. to about 35° C. The suitable solvent of step a) includes, but is not limited to esters, halogenated solvents, aromatic hydrocarbons, water and mixtures thereof. The esters such as methyl acetate, ethyl acetate, isopropyl acetate and the like; halogenated solvents such as methylene chloride, chloroform and the like; aromatic hydrocarbons include, but are not limited to toluene, xylene and the like mixtures thereof and mixture thereof preferable methylene chloride, water and mixture thereof.

The step b) process involves neutralizing the step a) solution with a base, where in the base includes but are not limited to sodium carbonate, potassium carbonate, sodium bicarbonate, potassium bicarbonate, ammonium hydroxide and mixtures thereof; preferably sodium bicarbonate.

Then the product containing organic layer may be separated and followed by concentrating under vacuum at a temperature of about 25° C. to about 65°; preferably at about 30° C. to about 45° C. to obtain carfilzomib as a residue.

The residue so obtained is dissolved in a suitable solvent to obtain a solution at a suitable temperature. Typically, the solution is heated at a temperature of at least about 30° C. to about reflux temperature, wherein the suitable solvent includes, but are not limited to methanol, ethanol, isopropanol, n-propanol, n-butanol, t-butanol and the like and mixtures thereof; preferably methanol. The carfilzomib amorphous Form may be precipitated by adding the step d) solution to an anti-solvent of water at a temperature of about 0° C. to about 35°; preferably at less than 10° C.

The carfilzomib amorphous Form can be recovered by any conventional techniques known in the art, for example filtration. Typically, if stirring is involved, the temperature during stirring can range from about 0° C. to about 30° C., preferably at less than 10° C. and the resultant product may optionally be further dried. Drying can be suitably carried out in a tray dryer, vacuum oven, air oven and the like. The drying can be carried out at a temperature ranging from about 35° C. to about 60° C. A high purity level of the resulting amorphous carfilzomib, obtained by the aforementioned process, may have a chemical purity of at least about 98%, as measured by HPLC, preferably at least about 99%, as measured by HPLC and more preferably at least about 99.9%, as measured by HPLC and contains less than 0.1%, as measured by HPLC of each of impurity of Formula 28, Formula 29, Formula 30, Formula 31, Formula 32, Formula 33, Formula 34, Formula 35, Formula 36, Formula 37, Formula 38, Formula 39, Formula 40 or Formula 41; preferably less than 0.05%, as measured by HPLC; more preferably less than 0.03%, as measured by HPLC.

In another embodiment, the present invention provides carfilzomib obtained by the aforementioned process, containing less than 0.05% as measured by HPLC of one or more of impurities of Formula 1 to Formula 41; preferably 0.03% as measured by HPLC.

In another embodiment, the present invention provides an improved process for the preparation of carfilzomib of Formula I or a pharmaceutically acceptable salt thereof:

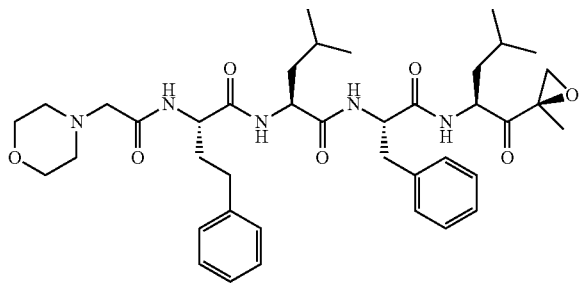

Formula I comprising:
   a1) reacting a compound of Formula II with a compound of Formula III or a salt thereof in presence of a coupling agent (C1), an additive (A1) and a base (B1) in a suitable solvent (S1) to obtain a compound of Formula IV,

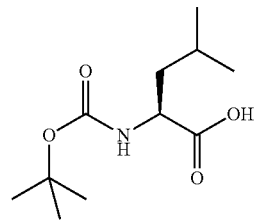

Formula II

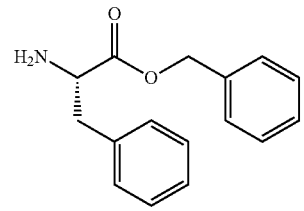

Formula III

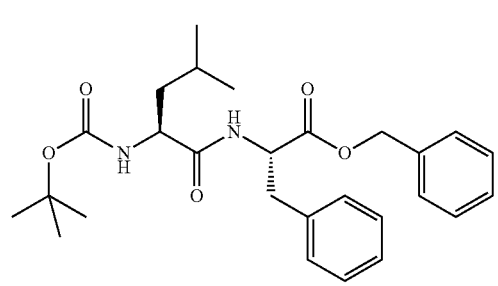

Formula IV b1) reacting the compound of Formula IV with a suitable acid to obtain a compound of Formula V or a salt thereof, Formula V

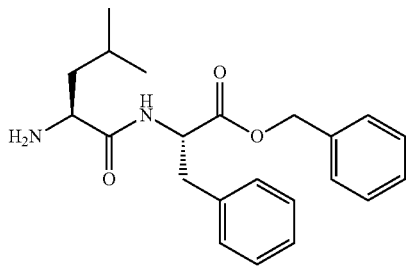

c1) reacting the compound of Formula V or a salt thereof with a compound of Formula VI in presence of a coupling agent (C2), an additive (A2) and a base (B2) in a suitable solvent (S2) to obtain a compound of Formula VII, Formula VI

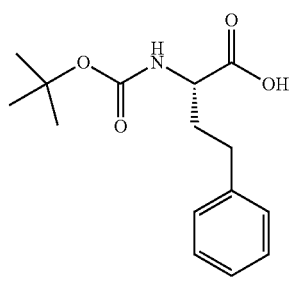

Formula VII

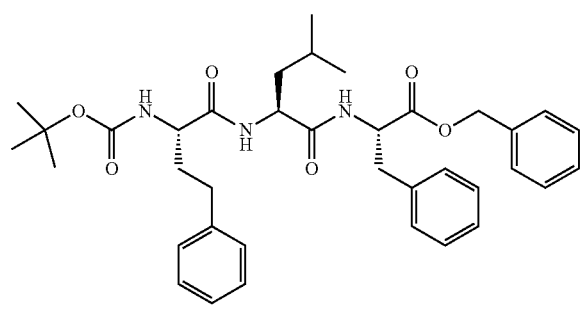

d1) reacting the compound of Formula VII with a suitable acid to obtain a compound of Formula XIII or a salt thereof, Formula XIII

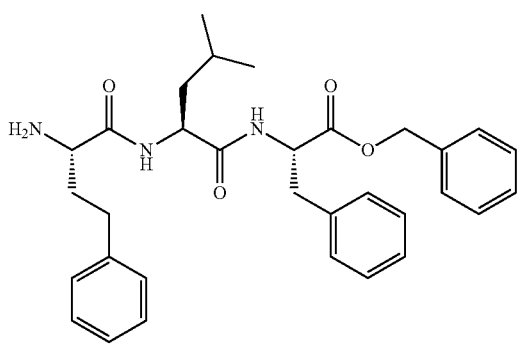

e1) reacting the compound of Formula XIII or a salt thereof with a compound of Formula XII in presence of a coupling agent (C5), an additive (A5) and a base (B5) in a suitable solvent (S5) to obtain a compound of Formula XIV, Formula XII

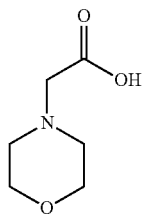

Formula XIV

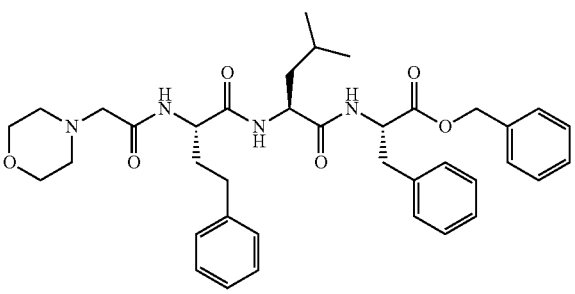

f1) deprotecting the compound of Formula XIV in presence of a suitable deprotecting agent to obtain a compound of Formula XV, and Formula XV

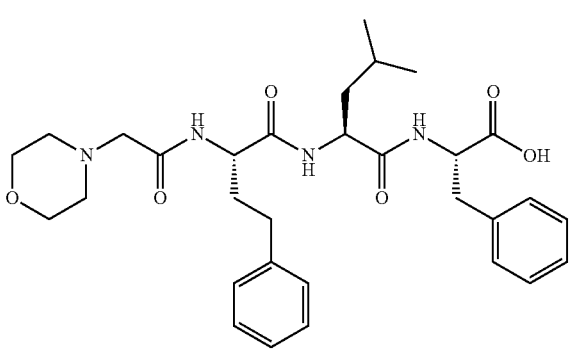

g1) reacting the compound of Formula XV with a compound of Formula IX or a salt thereof in presence of a coupling agent (C6), an additive (A6) and a base (B6) in a suitable solvent (S6) to obtain carfilzomib or a pharmaceutically acceptable salt thereof, Formula IX

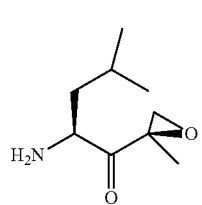

wherein the coupling agent (C1), (C2), (C5) and (C6) are used in an amount of about 0.9 to about 1.3 w/w mole equivalents per mole of Formula III, Formula IV, Formula VII and Formula XV respectively; wherein the additive (A1), (A2), (A3) and (A4) are used in catalytic amount of about 0.05 to about 0.5 w/w mole equivalents per mole of Formula III, Formula IV, Formula VII and Formula XV respectively.

The compound of Formula II, L-phenyl alanine benzyl ester of Formula III or a salt thereof, N-boc-homophenyl-alanine of Formula VI and morpholine acetic acid of Formula XII are known in the art and can be procured from commercially available sources.

The suitable salt of compounds of Formula III, Formula V or Formula IX employed in the aforementioned process is a salt of a mineral or organic acid, such as HCl, HBr, HI, $HNO_3$, $H_2SO_4$, acetic acid, trifluoro acetic acid, formic acid and the like.

The aforementioned process of step a1), step b2) and step c3) of converting compound of Formula II to compound of Formula VII can be carried out by the process described as above in the present specification.

Step d1):

The step d1) of the aforementioned process involves deprotection of amine protecting group of Formula VII with a suitable acid to obtain a compound of Formula XIII or a salt thereof.

The suitable acid used herein for step d1) is selected from the group consisting of hydrochloric acid, hydrobromic acid, sulfuric acid, phosphoric acid, acetic acid, trifluoro acetic acid, trichloro acetic acid, methane sulfonic acid and the like and mixture thereof; preferably trifluoro acetic acid.

The deprotection reaction of compound of Formula VII with a suitable acid may be carried out in a suitable organic solvent. The suitable organic solvent includes but is not limited to alcohols, ketones, ethers, halogenated hydrocarbons and mixtures thereof. The alcohols include, but are not limited to methanol, ethanol, isopropanol and the like; ketones include, but are not limited to acetone, methyl isobutyl ketone, methyl ethyl ketone and the like; ethers include, but are not limited to tetrahydrofuran, dimethyl ether, diisopropyl ether, methyl tertiary butyl ether, 1,4-dioxane and the like; halogenated hydrocarbons include, but are not limited to methylene chloride, ethylene chloride and the like and mixture thereof; preferably methylene chloride.

The deprotection reaction may be carried out at a temperature of about 0° C. to reflux temperature; preferably at 0° C. to about 50° C. After completion of the reaction, the reaction mass may be basified with a suitable aqueous base such as sodium carbonate, potassium carbonate and the like and then extracting the product with water immiscible organic solvent such as ethyl acetate, methylene chloride and the like. The free base of compound of Formula XIII may be isolated from the resultant water immiscible organic solvent by subjecting to evaporation under vacuum.

Step e1):

The step e1) of the aforementioned process involves reaction of the compound of Formula XIII or a salt thereof with a compound of Formula XII in presence of a coupling agent (C5), an additive (A5) and a base (B5) in a suitable solvent (S5) to obtain a compound of Formula XIV.

In a preferred embodiment, the present invention provides an improved process for preparation of carfilzomib of Formula I or a pharmaceutically acceptable salt thereof, comprising: reacting a compound of Formula XIII or a salt thereof; preferably free base, with a compound of Formula XII in presence of a coupling agent (C5), an additive (A5) and a base (B5) in a suitable solvent (S5) to obtain a compound of Formula XIV, wherein the coupling agent (C5) is used in an amount of about 0.9 to about 1.3 w/w mole equivalents per mole of Formula VII; wherein the additive (A5) is used in catalytic amount of about 0.05 to about 0.5 w/w mole equivalents per mole of Formula VII.

The coupling agent (C5) used herein for reaction of compound of Formula XIII or a salt thereof; preferably free base with a compound of Formula XII is selected from the group consisting of benzotriazol-1-yl-oxytripyrrolidino-phosphonium hexafluorophosphate (PyBOP), benzotriazol-1-yloxy-tris (dimethylamino)-phosphonium hexafluoro-phosphate (BOP), bromo-tripyrrolidino-phosphonium hexafluorophosphate (PyBrOP), Propylphosphonic anhydride (T3P), N-(3-dimethylaminopropyl)-N'-ethylcarbodiimide (EDC), 1,1'-Carbonyldiimidazole (CDI), diisopropylcarbodiimide (DCI), dicyclohexyl carbodiimide (DCC) and the like and mixture thereof; preferably benzotriazol-1-yl-oxytripyrrolidinophosphonium hexafluorophosphate (PyBOP).

The additive (A5) used herein for reaction of compound of Formula XIII or a salt thereof; preferably free base with a compound of Formula XII is selected from the group consisting of 1-Hydroxybenzotriazole (HOBt), 1-Hydroxy-7-aza-1H-benzotriazole (HOAt), 2-(1H-Benzotriazol-1-yl)-N,N,N',N'-tetramethylaminium tetrafluoroborate/hexa fluoro phosphate (TBTU), 2-(7-Aza-1H-benzotriazol-1-yl)-N,N,N',N'-tetramethylaminium hexafluorophosphate) (HATU) and the like and mixture thereof; preferably is 1-Hydroxybenzotriazole (HOBt).

In a preferred embodiment, the coupling agent (C5) used herein is benzotriazol-1-yl-oxytripyrrolidinophosphonium hexafluorophosphate (PyBOP) and is used in an amount of about 1.2 w/w mole equivalents Formula VII; additive (A5) used herein is 1-Hydroxybenzotriazole (HOBt) and is used in an amount of about 0.1 w/w mole equivalents per mole of Formula VII.

Exemplary bases (B5) used herein for reaction of compound of Formula XIII or a salt thereof; preferably free base with a compound of Formula XII includes but are not limited to diisopropylethyl amine, Imidazole or its salts, 1,8-Diaz-abicyclo[5.4.0]undec-7-en (DBU), tertiary amines or its hydro halide salts thereof selected from the group consisting of triethyl amine-hydrochloride and the like and mixtures thereof; preferably diisopropylethyl amine.

The reaction of compound of Formula XIII or a salt thereof; preferably free base with a compound of Formula XII is advantageously carried out in a solvent (S5). Suitable solvent include, but are not limited to ethers, esters, halogenated hydrocarbons, amides, aromatic solvents, nitriles, or mixtures thereof. The ether includes, but are not limited to tetrahydrofuran, 2-methyltetrahydrofuran and the like; esters include, but are not limited to methyl acetate, ethyl acetate, propyl acetate, butyl acetate and the like; halogenated hydrocarbons include, but are not limited to methylene chloride, ethylene chloride and the like; amides includes, but are not limited to dimethyl formamide, dimethyl acetamide, N-methyl pyrrolidinone and the like; aromatic solvents include, but are not limited to toluene, chlorobenzene and the like; nitriles include, but are not limited to acetonitrile, propionitrile and the like and mixtures thereof; preferably dimethyl formamide and acetonitrile.

The reaction temperature should be sufficient to effect coupling reaction. Typically the reaction temperature may be from about −10° C. to about reflux temperature. Preferably the reaction temperature is about 25° C. to about 50° C. The reaction may take from about 0.5 hours to about 6 hours depending upon the coupling agent and additive, solvent and temperature chosen, preferably about 1 hour to 4 hours.

After completion of the reaction, the compound of Formula XIV is advantageously isolated by quenching the step e1) reaction mass in to water to precipitate compound of Formula XIV as solid. The precipitated compound of Formula XIV may be separated by methods known in the art, for example filtration.

The resultant product may optionally be further dried. Drying can be suitably carried out in a tray dryer, vacuum oven, air oven and the like. The drying can be carried out at a temperature ranging from about 40° C. to about 60° C. A high purity level of the resulting Formula XIV, obtained by the aforementioned process, may have a chemical purity of at least about 95%, as measured by HPLC, preferably at least about 98%, as measured by HPLC and more preferably at least about 99.0%, as measured by HPLC; and contains less than 0.5% of total impurities of byproducts HOBt, PyBOP, tris(pyrrolidino phosphine) oxide, isomer impurities of Formula 8, Formula 9, Formula 10 and Formula 11, as measured by HPLC; preferably less than 0.3%, as measured by HPLC.

In another embodiment, the obtained compound of Formula XIV having less than 0.1%, as measured by HPLC of each of impurity of Formula 8, Formula 9, Formula 10 or Formula 11; preferably less than 0.05%, as measured by HPLC; more preferably less than 0.03%, as measured by HPLC.

Step f1):

The step f1) of the aforementioned process involves deprotection of benzyl protecting group of the compound of Formula XIV in presence of a suitable deprotecting agent to obtain a compound of Formula XV.

The suitable deprotecting agent used herein for deprotection of the compound of Formula XV is include, but is not limited to palladium on carbon/ammonium formate, palladium on carbon/ammonium acetate, palladium on carbon/hydrogen gas, palladium hydroxide/hydrogen gas, raney nickel/hydrogen gas, platinum oxide/hydrogen gas, zinc/hydrogen gas and the like; preferably palladium on carbon/ammonium formate.

The deprotection reaction of compound of Formula XIV with a suitable deprotecting agent may be carried out in a suitable solvent. The suitable solvent includes but is not limited to alcohols, esters, ethers, acetic acid, water and mixtures thereof. The alcohols include, but are not limited to methanol, ethanol, isopropanol and the like; esters include, but are not limited to methyl acetate, ethyl acetate, propyl acetate, butyl acetate and the like; ethers include, but are not limited to tetrahydrofuran and the like; water and mixture thereof; preferably methanol.

The deprotection reaction may be carried out at a temperature of about 0° C. to reflux temperature; preferably at 0° C. to about 50° C. After completion of the reaction, the reaction mass may be filtered and resulting compound of Formula XV may be isolated by subjecting the filterate to evaporation under vacuum to obtain a residue. Optionally the obtained residue is treated with a suitable solvent such as acetone and stirred for about 2 hours and the resultant compound of Formula XV may be isolated by techniques known in the art, for example filtration.

The resultant product may optionally be further dried. Drying can be suitably carried out in a tray dryer, vacuum oven, air oven and the like. The drying can be carried out at a temperature ranging from about 40° C. to about 60° C. A high purity level of the resulting Formula XV, obtained by the aforementioned process, may have a chemical purity of at least about 95%, as measured by HPLC, preferably at least about 98%, as measured by HPLC and more preferably at least about 99.5%, as measured by HPLC; and contains less than 0.5% of total impurities of Formula 12, Formula 13, Formula 14 and Formula 15 as measured by HPLC; preferably less than 0.3%, as measured by HPLC.

In another embodiment, the obtained compound of Formula XV having less than 0.1%, as measured by HPLC of each of impurity of Formula 12, Formula 13, Formula 14 or Formula 15; preferably less than 0.05%, as measured by HPLC; more preferably less than 0.03%, as measured by HPLC.

Step g1):

The step g1) of the aforementioned process involves reaction of the compound of Formula XV with a compound of Formula IX or a salt thereof in presence of a coupling agent (C6), an additive (A6) and a base (B6) in a suitable solvent (S6) to obtain carfilzomib of Formula I.

In a preferred embodiment, the present invention provides an improved process for preparation of carfilzomib of Formula I or a pharmaceutically acceptable salt thereof, comprising: reacting a compound of Formula XV with a compound of Formula IX or a salt thereof in presence of a coupling agent (C6), an additive (A6) and a base (B6) in a suitable solvent (S6) to obtain carfilzomib or a pharmaceutically acceptable salt thereof; wherein the coupling agent (C6) is used in an amount of about 0.9 to about 1.3 w/w mole equivalents per mole of Formula XV; wherein the additive (A6) is used in catalytic amount of about 0.05 to about 0.5 w/w mole equivalents per mole of Formula XV.

In a preferred embodiment, the compound of Formula IX is having less than 0.1% of its corresponding isomers or its impurities of Formula E, Formula F, Formula G, Formula H, Formula I and Formula J:

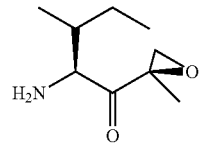

Formula E

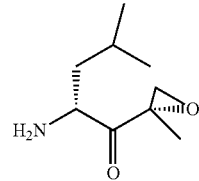

Formula F

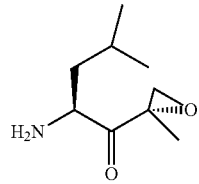

Formula G

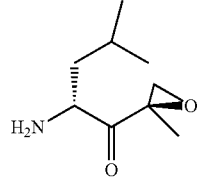

Formula H

Formula I

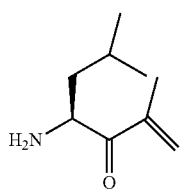

Formula J

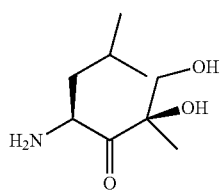

The coupling agent (C6), an additive (A6), base (B6) and solvent (S6) are used herein for reaction of compound of Formula XV with a compound of Formula IX or a salt thereof, preferably free base is same as used for step e1) as mentioned above.

In a preferred embodiment, the coupling agent (C6) used herein is benzotriazol-1-yl-oxytripyrrolidinophosphonium hexafluorophosphate (PyBOP) and is used in an amount of about 1.2 w/w mole equivalents per mole of Formula XV; additive (A6) used herein is 1-Hydroxybenzotriazole (HOBt) and is used in an amount of about 0.1 w/w mole equivalents per mole of Formula XV.

The reaction temperature should be sufficient to effect coupling reaction. Typically the reaction temperature may be from about −10° C. to about reflux temperature. Preferably the reaction temperature is about 25° C. to about 50° C. The reaction may take from about 0.5 hours to about 6 hours depending upon the coupling agent and additive, solvent and temperature chosen, preferably about 1 hour to 4 hours.

After completion of the reaction, the obtained carfilzomib may be isolated by subjecting the reaction mass to evaporation under vacuum to obtain a residue.

Alternatively, the resultant residue of carfilzomib can be converted in to its pharmaceutically acceptable salt thereof; preferably maleate salt by using the process described as above in the present specification.

In another embodiment, the present invention provides the conversion of carfilzomib pharmaceutically acceptable salt in to its free base of carfilzomib amorphous form by using the process described as above in the present specification.

A high purity level of the resulting amorphous carfilzomib, obtained by the aforementioned process, may have a chemical purity of at least about 98%, as measured by HPLC, preferably at least about 99%, as measured by HPLC and more preferably at least about 99.9%, as measured by HPLC and contains less than 0.1%, as measured by HPLC of each of impurity of Formula 28, Formula 29, Formula 30, Formula 31, Formula 32, Formula 33, Formula 34, Formula 35, Formula 36, Formula 37, Formula 38, Formula 39, Formula 40 or Formula 41; preferably less than 0.05%, as measured by HPLC; more preferably less than 0.03%, as measured by HPLC.

In another embodiment, the present invention provides carfilzomib obtained by the aforementioned process, containing less than 0.05% as measured by HPLC of one or more of impurities of Formula 1 to Formula 41; preferably 0.03% as measured by HPLC.

In another embodiment, the present invention provides a compound of Formula 41:

Formula 41

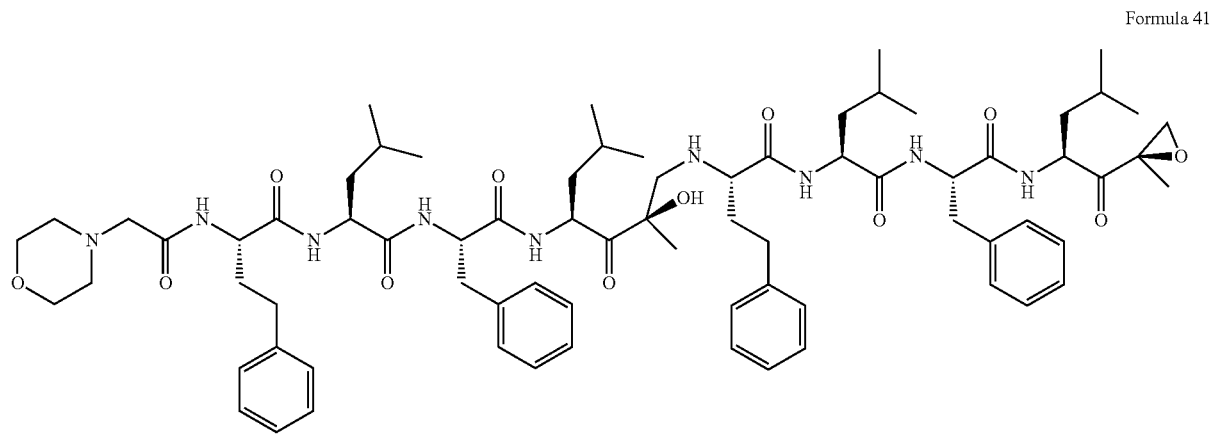 [SMILES: CC(C)C[C@H](NC(=O)[C@H](CCc1ccccc1)NC[C@@](C)(O)C(=O)[C@H](CC(C)C)NC(=O)[C@H](Cc1ccccc1)NC(=O)[C@H](CC(C)C)NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

In another embodiment, the present invention provides a compound of Formula 41 characterized by $^1$H-NMR (DMSO-d6): δ 0.80 (m, 6H), 0.83 (m, 6H), 0.83 (m, 6H), 0.85 (m, 6H), 0.87 (m, 3H), 1.11 (S, 3H), 1.24 (m, 1H), 1.32 (m, 2H), 1.36 (m, 3H), 1.36 (m, 2H), 1.4 (S, 3H), 1.53 (m, 1H), 1.53 (m, 1H), 1.60 (m, 2H), 1.63 (m, 1H), 1.63 (m, 1H), 1.66 (m, 1H), 1.84 (m, 2H), 2.38 (m, 1H), 2.45 (m, 4H), 2.5 (m, 2H), 2.63 (m, 1H), 2.75 (m, 1H), 2.75 (m, 1H), 2.9 (m, 1H), 2.95 (m, 1H), 2.96 (m, 1H), 2.96 (m, 2H), 3.12 (d, 1H), 3.6 (m, 4H), 4.32 (m, 1H), 4.32 (m, 1H), 4.35 (m, 1H), 4.36 (m, 1H), 4.54 (m, 1H), 4.54 (m, 1H), 5.1 (t, 1H), 5.4 (s, 1H), 7.09-7.18 (m, 10H), 7.11-7.26 (m, 10H), 7.88 (d, 1H), 8.04 (m, 1H), 8.09 (m, 1H), 8.11 (m, 1H), 8.29 (d, 1H).

The repetition of '818 patent, which involves all the coupling reactions with excess quantity of coupling agent, an additive and solvent results less percentage of product yields in all stages when compared to the theoretical yields. In contrast the present invention involve use of less quantity of coupling agents, an additives and solvents for the preparation of carfilzomib, which observes less reaction time with higher product convertion there by process results higher yields and purity.

A comparative step wise results of US'818 patent process and the present aforementioned process are reported in the following table:

| Step | Process | Reagents (mole eqt) | Solvent | Purity by HPLC | Reported Yield (w/w %) | Theoretical yield (w/w %) |
|---|---|---|---|---|---|---|
| Reaction of Formula II with Formula III | US'818 process | PyBOP (1.6); HOBt (1.6) | Acetonitrile (45 vol) | 88.12% | 1% | 1.6% |
| | Present process | PyBOP (1.2); HOBt (0.1) | DMF (5 vol) | 99.53% | 1.4% | |
| Reaction of Formula V with Formula VI | US'818 process | PyBOP (1.6); HOBt (1.6) | Acetonitrile (22 vol) | 89.35% | 0.99% | 1.35% |
| | Present process | PyBOP (1.2); HOBt (0.1) | DMF (5vol) | 97.1% | 1.2% | |
| Reaction of Formula XIII with Formula XII | US'818 process | PyBOP (1.6); HOBt (1.6) | DMF (24 vol) | 92.1% | 0.6% | 1.04% |
| | Present process | PyBOP (1.2); HOBt (0.1) | DMF (5 vol) | 97.6% | 0.95% | |
| Reaction of Formula XV with Formula IX | US'818 process | PyBOP (1.6); HOBt (1.6) | Acetonitrile (50 vol) | 26% | 0.8% (isolated as amorphous) | 1.27% |
| | Present process | PyBOP (1.2); HOBt (0.1) | Acetonitrile (50 vol) | 99% | 1% (isolated as maleate salt) | |

In another embodiment, the present invention provides a process for preparation of tert-butyl ((2S)-4-methyl-1-((2R)-2-methyloxirane-2-yl)-1-oxo-pentan-2-yl)-carbamate of Formula XVI, Formula XVI

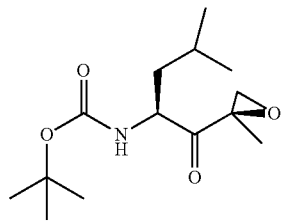

comprising:
i) reacting a compound of Formula XVII with alkyl magnesium halide to obtain a compound of Formula XVIII,
ii) crystallizing the compound of Formula XVIII from a suitable solvent system to obtain crystalline compound of Formula XVIII, Formula XVII

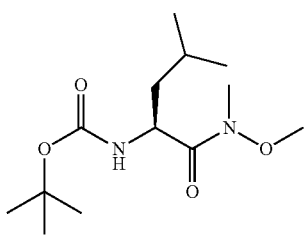

-continued

Formula XVIII

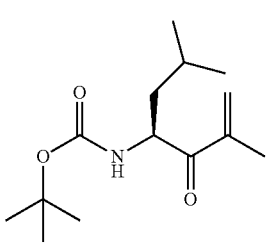

iii) reducing the crystalline compound of Formula XVIII in presence of a suitable reducing agent to obtain a diastereomeric mixture of compound of Formula XIXa and Formula XIXb,
iv) crystallizing the mixture of compound of Formula XIXa and Formula XIXb from a suitable solvent system to obtain a mixture of crystalline compound of Formula XIXa and Formula XIXb, Formula XIXa

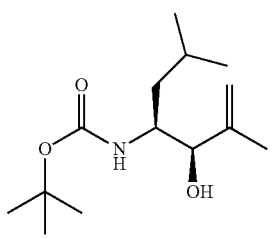

Formula XIXb

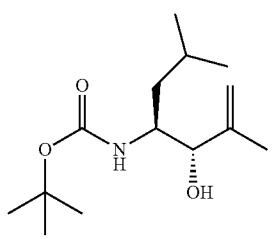

v) epoxidation and followed by oxidation of diastereomeric mixture of crystalline compound of Formula XIXa and Formula XIXb to obtain a diastereomeric mixture of compound of Formula XVI and Formula XVIa, Formula XVI

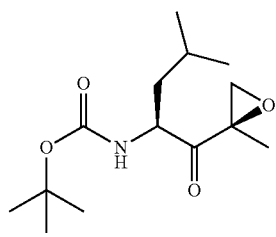

Formula XVIa

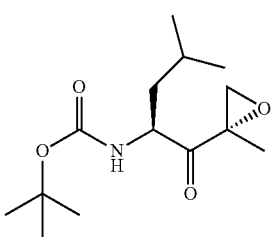

vi) separating the compound of Formula XVI from the diastereomeric mixture of compound of Formula XVI and Formula XVIa by chromatography, and vii) crystallizing the compound of Formula XVI from a suitable solvent system to obtain crystalline compound of Formula XVI.

The starting material of Formula XVII is known in the art and can be prepared by any known method, for example WO2009/045467 or may be by prepared by the process described in example part.

Step i) of reaction of compound of Formula XVII with alkyl magnesium halide such as iso-propenyl magnesium bromide is carried out in a suitable organic solvent, which includes but is not limited to esters, ketones, ethers and mixtures thereof. The esters include, but are not limited to ethyl acetate, isopropyl acetate and the like; ketones include, but are not limited to acetone, methyl isobutyl ketone, methyl ethyl ketone and the like; ethers include, but are not limited to tetrahydrofuran, dimethyl ether, diisopropyl ether, methyl tertiary butyl ether, 1,4-dioxane and the like and mixtures thereof preferably tetrahydrofuran.

The reaction of compound of Formula XVII with iso-propenyl magnesium bromide is carried out at a temperature of about 25° C. to about reflux temperature; preferably at about 25° C. to about 50° C.

After completion of the reaction, the reaction mass may be quenched into ammonium chloride solution and compound of Formula XVIII may be extracted with water immiscible organic solvent such as ethyl acetate, methylene chloride, methyl tertiary butyl ether; preferable ethyl acetate and distilling out the water immiscible organic solvent under vacuum to obtain a compound of Formula XVIII as residue. The obtained residue may be purified by column chromatography using ethyl acetate and cyclohexane as an eluent system and the compound containing solvent fractions are combined and distilled under vacuum to obtain a compound of Formula XVIII as residue. The residue obtained is purified by a solvent crystallization method to isolating the compound of Formula XVIII as a crystalline solid.

In an embodiment, the compound of Formula XVIII may be purified by recrystallization to obtain compound of Formula XVIII as a crystalline solid.

In another embodiment, the present invention provides a process for the preparation of compound of Formula XVIII as crystalline solid, comprising:
i) providing a solution of compound of Formula XVIII in a suitable solvent,
ii) optionally cooling the step i) solution to less than 20° C.,
iii) adding an anti-solvent to the step ii) solution, and
iv) isolating the crystalline compound of Formula XVIII; wherein the suitable solvent is selected from the group comprising alcohols, ketones, esters, nitriles and the like and mixture thereof; and the anti-solvent is selected from the group comprising aliphatic hydrocarbons, cyclic hydrocarbons, ethers and the like and water and mixture thereof.

The step i) of providing a solution of Formula XVIII includes heating to dissolve the compound of Formula XVIII obtained by the process described above in a suitable solvent at a temperature of about 25° C. to about reflux temperature; preferably at about 25° C. to about 35° C.

The suitable solvent for dissolving compound of Formula XVIII include, but is not limited to alcohols, ketones, esters, nitriles and the like and mixture thereof. The alcohols include, but are not limited to methanol, ethanol, propanol, isopropanol and the like; ketones include, but are not limited to acetone, methyl isobutyl ketone, methyl ethyl ketone and the like; esters include, but are not limited to methyl acetate, ethyl acetate, isopropyl acetate and the like; nitriles include, but are not limited to acetonitrile, propionitrile and the like and mixture thereof preferably acetone. The optional step of cooling the step i) solution to less than 20° C.; preferably about −10° C. to about 0° C.

Then, adding an antisolvent to the step ii) reaction solution and stirring the solution for a period of about 1 hour to about 2 hours to precipitating out the crystalline compound of Formula XVIII. Then, the resultant compound of Formula XVIII can be recovered by any conventional techniques known in the art, for example filtration and the resultant product may optionally be further dried.

The suitable anti-solvent for precipitating the compound of Formula XVIII include, but is not limited to aliphatic hydrocarbons, cyclic hydrocarbons, ethers and the like and water and mixture thereof. The aliphatic hydrocarbons include, but are not limited to n-hexane, n-heptane, n-pentane and the like; cyclic hydrocarbons include, but are not limited to cyclopentane, cyclohexane and the like; ethers include, but are not limited to methyl tertiary butyl ether, diethyl ether and the like; and water and mixture thereof preferable water.

Figure 9:
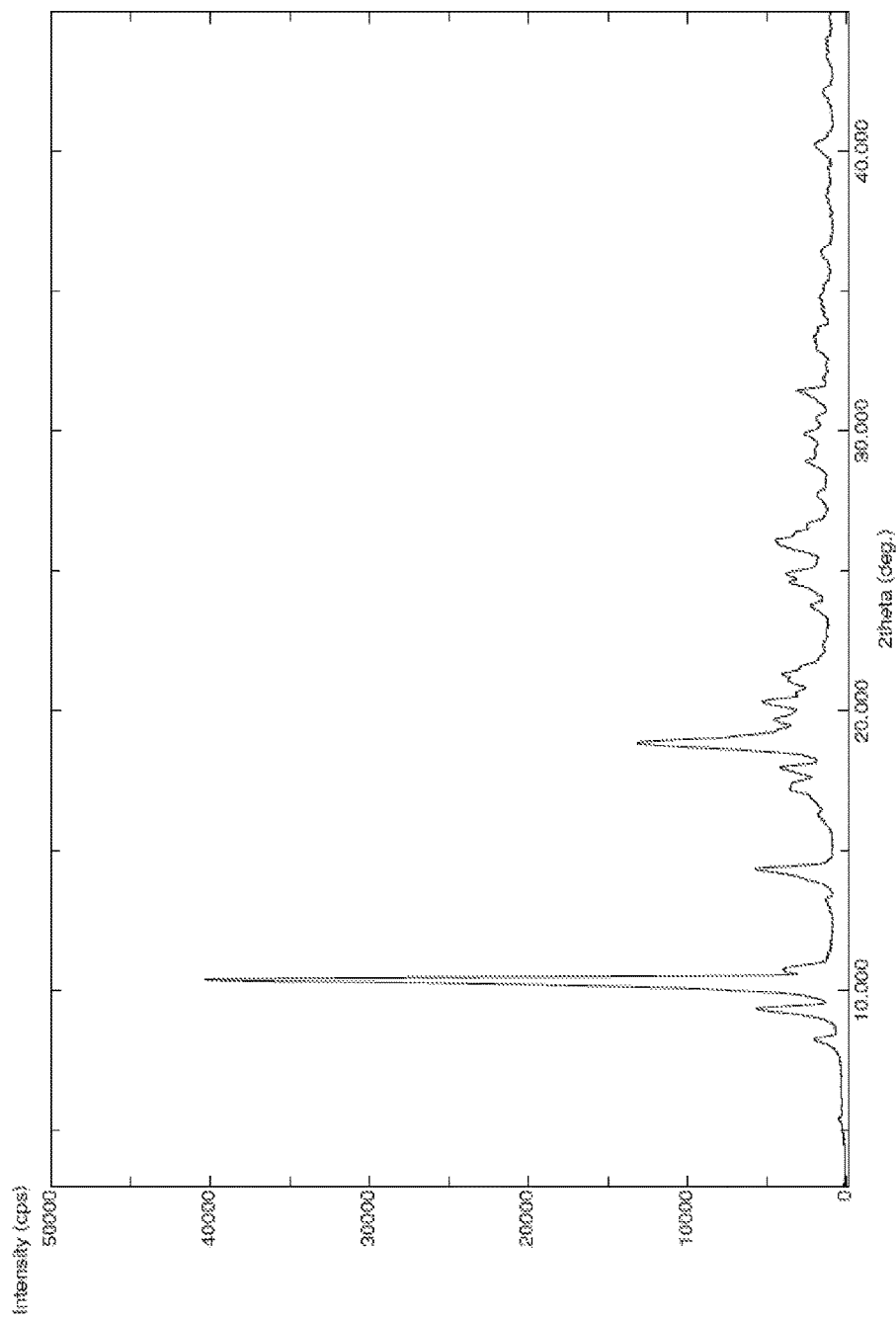
FIG. 9 is the characteristic powder X-ray diffraction (XRD) pattern of crystalline compound of Formula XVIII.

In another embodiment, the present invention provides crystalline compound of Formula XVIII characterized by a powder X-Ray diffraction (PXRD) pattern substantially in accordance with FIG. 9.

The compound of Formula XVIII obtained according to the process described just as above can be converted in to a diastereomeric mixture of compound of Formula XIXa and Formula XIXb using a reducing agent.

The reducing agent used herein includes but is not limited to sodium borohydride with cerium trichloride, lithium tri-tert-butoxyaluminium hydride; preferable sodium borohydride with cerium trichloride.

The reduction of compound of Formula XVIII can be carried out in a suitable organic solvent. The suitable organic solvent includes but is not limited to alcohols, ethers and the like and mixture thereof. The alcohols include, but are not limited to methanol, ethanol, propanol, isopropanol and the like; ethers include, but are not limited to tetrahydrofuran, dimethyl ether and the like and mixture thereof; preferably methanol. The reduction of compound of Formula III is carried out at a temperature of about −15° C. to about 35° C.; preferably at about −10 to 0° C.

After completion of the reaction, the reaction mass may be quenched with acetic acid and compound of Formula XIX may be extracted with a water immiscible organic solvent such as ethyl acetate, methylene chloride, methyl tertiary butyl ether; preferable ethyl acetate and distilling out the water immiscible organic solvent under vacuum to obtain a diastereomeric mixture of compound of Formula XIXa and Formula XIXb as residue. The residue obtained is purified by a solvent crystallization method to isolate the diastereomeric mixture of compound of Formula XIXa and Formula XIXb as a crystalline solid.

In an embodiment, the diastereomeric mixture of compound of Formula XIXa and Formula XIXb may be purified by recrystallization using a solvent to obtain corresponding pure compounds as a crystalline solid.

In another embodiment, the present invention provides a process for the preparation of diastereomeric mixture of compound of Formula XIXa and Formula XIXb as a crystalline solid, comprising:
  i) providing a solution of diastereomeric mixture of a compound of Formula XIXa and Formula XIXb in a suitable solvent,
  ii) cooling the step i) solution to less than 10° C.,
  iii) adding an anti-solvent to the step ii) solution, and
  iv) isolating the crystalline compound of Formula XIX;
    wherein the suitable solvent is selected from the group comprising alcohols, ketones, esters, nitriles and the like and mixture thereof; and the anti-solvent is selected from the group comprising aliphatic hydrocarbons, cyclic hydrocarbons, ethers and the like and water and mixture thereof.

The step i) of providing a solution of diastereomeric mixture of a compound of Formula XIXa and Formula XIXb includes heating to dissolve the diastereomeric mixture of Formula XIXa and XIXb obtained by the process described above, in a suitable solvent at a temperature of about 25° C. to about reflux temperature; preferably at about 25° C. to about 35° C.

The suitable solvent for dissolving a diastereomeric mixture of a compound of Formula XIXa and Formula XIXb include, but are not limited to alcohols, ketones, esters, nitriles and the like and mixtures thereof. The alcohols include, but are not limited to methanol, ethanol, propanol, isopropanol and the like; ketones include, but are not limited to acetone, methyl isobutyl ketone, methyl ethyl ketone and the like; esters include, but are not limited to methyl acetate, ethyl acetate, isopropyl acetate and the like; nitriles include, but are not limited to acetonitrile, propionitrile and the like and mixture thereof; preferably methanol.

The step ii) process involves cooling the step a) resulted solution to less than 10° C.; preferably about 0° C. to about 5° C.

The step iii) process involves addition of an anti-solvent to the above step ii) reaction solution and stirring the solution for about 2 hours to precipitate the crystalline diastereomeric mixture of a compound of Formula XIXa and Formula XIXb. Then, the resultant pure diastereomeric mixture of compound of Formula XIXa and XIXb can be recovered by any conventional techniques known in the art, for example filtration and the resultant product may optionally be further dried.

The suitable anti-solvent for precipitating the diastereomeric mixture of a compound of Formula XIXa and Formula XIXb include, but is not limited to aliphatic hydrocarbons, cyclic hydrocarbons, ethers and the like and water and mixture thereof. The aliphatic hydrocarbons include, but are not limited to n-hexane, n-heptane, n-pentane and the like; cyclic hydrocarbons include, but are not limited to cyclopentane, cyclohexane and the like; ethers include, but are not limited to methyl tertiary butyl ether, diethyl ether and the like; and water and mixture thereof preferable water.

Figure 10:
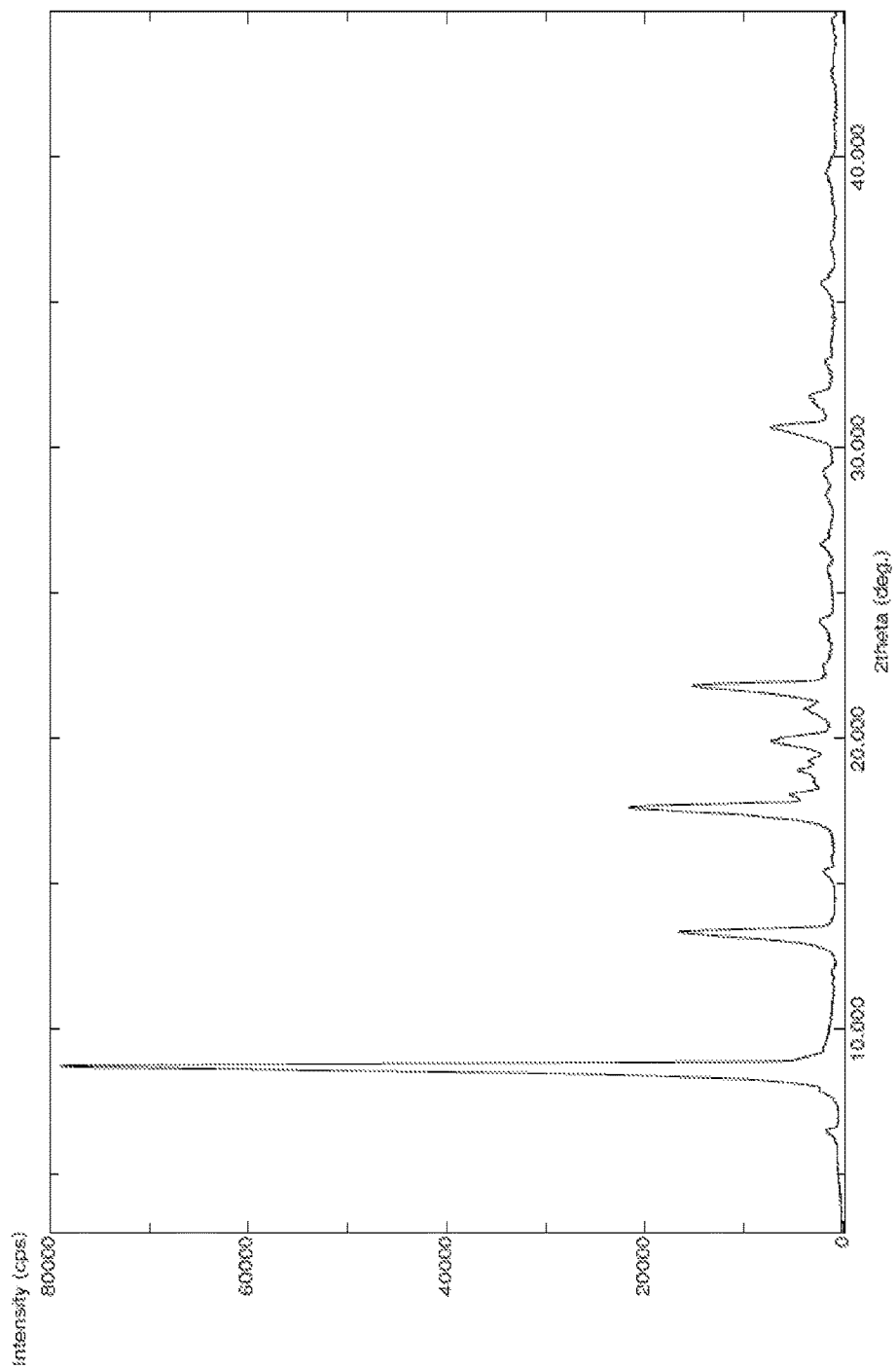
FIG. 10 is the characteristic powder X-ray diffraction (XRD) pattern of crystalline diastereomeric mixture of compound of Formula XIXa and Formula XIXb.

In another embodiment, the present invention provides crystalline diastereomeric mixture of a compound of Formula XIXa and Formula XIXb characterized by a powder X-Ray diffraction (PXRD) pattern substantially in accordance with FIG. 10.

The diastereomeric mixture of compound of Formula XIXa and Formula XIXb obtained according to the process described as above can be converted in to diastereomeric mixture of compound of Formula XVIa and Formula XVIb by epoxidation and followed by oxidation.

The epoxidizing agent used herein includes but is not limited to m-chloroperbenzoic acid, VO(acac)$_2$, hydrogen peroxide and the like; preferable m-chloroperbenzoic acid.

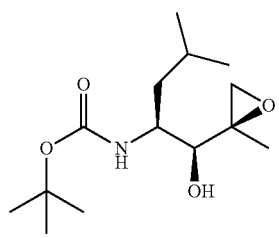

Formula XXa

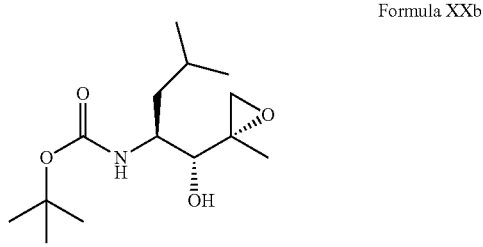

Formula XXb

The epoxidation is carried out in a suitable organic solvent such as methylene chloride at a temperature of about 0° C. to about 50° C.; preferably at about 0° C. to about 35° C.

After completion of the reaction, diastereomeric mixture of compound of Formula XXa and Formula XXb may be isolated by extracting the reaction mass with water immiscible organic solvent such as ethyl acetate, methylene chloride, methyl tertiary butyl ether; preferable methylene chloride and distilling out the water immiscible organic solvent under vacuum to obtain a diastereomeric mixture of compound of Formula XXa and Formula XXb as residue.

Then the obtained diastereomeric mixture of compound of Formula XXa and Formula XXb can be converted in to a diastereomeric mixture of compound of Formula XVI and Formula XVIa in presence of a suitable oxidizing agent.

The oxidizing agent used herein include but is not limited to Dess-Martin periodinane, tetrapropylammonium perruthenate with 4-methylmorpholine-N-oxide; preferable Dess-Martin periodinane.

The oxidation is carried out in a suitable organic solvent such as acetonitrile at a temperature of about 0° C. to about 50° C.; preferably at about 25 to about 30° C.

After completion of the reaction, the diastereomeric mixture of compound of Formula XVI and Formula XVIa may be extracted with water immiscible organic solvent such as ethyl acetate, methylene chloride, methyl tertiary butyl ether; preferable ethyl acetate and distilling the water immiscible organic solvent under vacuum to obtain diastereomeric mixture of compound of Formula XVI and Formula XVIa as residue.

The compound of Formula XVI may be separated from the obtained diastereomeric mixture of compound of Formula XVI and Formula XVIa by subjecting the mixture to column chromatography by eluting with ethyl acetate and cyclohexane solvent system and the product containing solvent fractions are collected and distilled under vacuum to obtain compound of Formula XVI as a residue.

The resulting compound of Formula XVI, obtained by the aforementioned process, may have a chemical purity of at least about 99%, as measured by HPLC and about 0.5 to 1% of compound of Formula XVIII as measured by HPLC.

In another embodiment, the present invention provides an improved process for the preparation of compound of Formula XVI, comprising purifying the compound of Formula XVI as obtained by the process described above or may be obtained by any known process, as a starting material or as an intermediate by solvent and anti-solvent method to obtain pure compound of Formula XVI which is having chemical purity of at least about 99.9%, as measured by HPLC and less than about 0.1% of Formula XVIII as measured by HPLC.

In another embodiment, the present invention provides a process for the purification of tert-butyl ((2 S)-4-methyl-1-((2R)-2-methyloxirane-2-yl)-1-oxo-pentan-2-yl)-carbamate of Formula XVI, comprising:
  i) providing a solution of tert-butyl ((2S)-4-methyl-1-((2R)-2-methyloxirane-2-yl)-1-oxo-pentan-2-yl)-carbamate of Formula XVI in a suitable solvent,
  ii) cooling the step i) solution to less than 5° C.,
  iii) optionally adding seed compound of Formula XVI to the step ii) solution, and
  iv) isolating the pure compound of Formula XVI; wherein the suitable solvent is selected from aliphatic hydrocarbons, cyclic hydrocarbons, ethers and the like and mixture thereof.

In another embodiment, the present invention provides a process for preparation of tert-butyl ((2S)-4-methyl-1-((2R)-2-methyloxirane-2-yl)-1-oxo-pentan-2-yl)-carbamate of Formula XVI having less than 0.1% of compound of Formula XVIII as measured by HPLC, comprising purifying the compound of Formula XVI by the process described above.

The step i) of providing a solution of tert-butyl ((2S)-4-methyl-1-((2R)-2-methyloxirane-2-yl)-1-oxo-pentan-2-yl)-carbamate of Formula XVI includes heating to dissolve the compound of Formula XVI obtained by the process described as above, in a suitable solvent at a temperature of about 25° C. to about reflux temperature; preferably at about 25° C. to about 35° C.

The suitable solvent for dissolving compound of Formula XVI include, but not limited to aliphatic hydrocarbons, cyclic hydrocarbons, ethers and the like and mixtures thereof. The aliphatic hydrocarbons include, but are not limited to n-hexane, n-heptane, n-pentane and the like; cyclic hydrocarbons include, but are not limited to cyclopentane, cyclohexane and the like; ethers include, but are not limited to methyl tertiary butyl ether, diethyl ether and the like and mixture thereof preferably n-heptane.

The resultant solution may be cooled to less than 5° C., preferably about −10° C. to 0° C. Optionally the solution may be seeding with a seed compound of Formula XVI to precipitating out the crystalline compound of Formula XVI. The precipitated crystalline compound of Formula XVI may be isolated by methods known in the art, for example filtration followed by drying at suitable temperatures.

Figure 8:
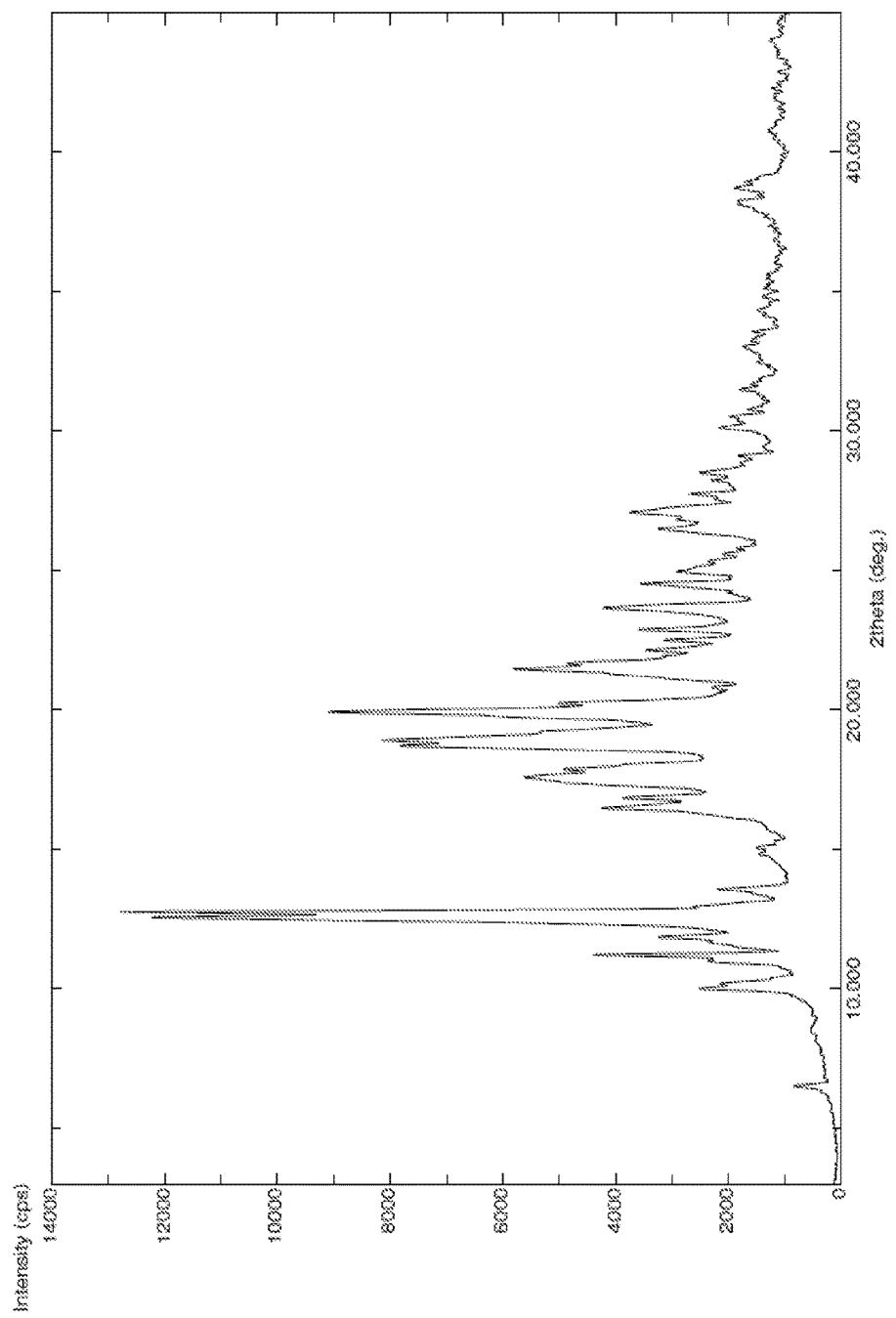
FIG. 8 is the characteristic powder X-ray diffraction (XRD) pattern of crystalline compound of Formula XVI.

In another embodiment, the present invention provides crystalline tert-butyl ((2S)-4-methyl-1-((2R)-2-methyloxirane-2-yl)-1-oxo-pentan-2-yl)-carbamate of Formula XVI characterized by a powder X-Ray diffraction (PXRD) pattern substantially in accordance with FIG. 8.

In another embodiment, the present invention provides compound of Formula XVI containing less than 0.1% of compound of Formula XVIII as measured by HPLC.

In another embodiment, the present invention provides an improved process for the preparation of carfilzomib, comprising preparing the tert-butyl ((2S)-4-methyl-1-((2R)-2-methyloxirane-2-yl)-1-oxo-pentan-2-yl)-carbamate of Formula XVI as process described above, and converting the tert-butyl ((2S)-4-methyl-1-((2R)-2-methyloxirane-2-yl)-1-oxo-pentan-2-yl)-carbamate of Formula XVI in to carfilzomib by any process known in the art or by the process described in the above specification.

In another embodiment, the present invention provides a process for the preparation of carfilzomib, comprising providing a compound of Formula XVI as obtained by the process described above, as a starting material or as an intermediate, where the purity of the carfilzomib having at least about 99% and less than 0.1% of compound of Formula XVIII as measured by HPLC, preferably at least about 99.5% and less than 0.05% of compound of Formula XVIII as measured by HPLC.

The X-Ray powder diffraction can be measured by an X-ray powder diffractometer equipped with a Cu-anode ([λ]=1.54 Angstrom), X-ray source operated at 30 kV, 15 mA. Two-theta calibration is performed using an NIST SRM 640c Si standard. The sample was analyzed using the following instrument parameters: measuring range=3-45° 2θ; step width=0.020°; and scan speed=5°/minute.

As used herein, the pharmaceutical acceptable salts include acid addition salts formed with inorganic acids or with organic acids. The inorganic acids may be selected from hydrochloric acid, hydrobromic acid, sulfuric acid, phosphoric acid, nitric acid, sulfamic acid, and the like; organic acids may be selected from acetic acid, oxalic acid, fumaric acid, succinic acid, tartaric acid, salicylic acid, benzoic acid, glycolic acid, methane sulfonic acid, ethanesulfonic acid, benzenesulfonic acid, p-toluenesulfonic acid, lactic acid, maleic acid, malonic acid, malic acid and the like.

In another embodiment, the present invention provides carfilzomib or a pharmaceutically acceptable salt thereof and its intermediates, obtained by the above process, as analyzed using high performance liquid chromatography ("HPLC") with the conditions are tabulated below:

| | |
|---|---|
| Column | Halo C18 (100 × 4.6) mm, 2.7 μm |
| Column temperature | 35° C. |
| Mobile phase | Mixture of buffer and Acetonitrile (30:70) v/v |
| Buffer | Dipotassium hydrogen phosphate |
| Diluent | Water and Acetonitrile (30:70) v/v |
| Flow rate | 1.0 mL/min |
| Wavelength | By UV at 210 nm |
| Injection Volume | 10 μL |
| Elution | Gradient |

In another embodiment, the present invention provides a pharmaceutical composition, comprising carfilzomib or a pharmaceutically acceptable salt thereof prepared by the processes of the present invention and at least one pharmaceutically acceptable excipient. Such pharmaceutical composition may be administered to a mammalian patient in any dosage form, e.g., injectable solution, solid, liquid, powder etc.

EXAMPLES

The following non limiting examples illustrate specific embodiments of the present invention. They are not intended to be limiting the scope of the present invention in any way.

Example 1: Preparation of Compound of Formula IV

A mixture of N-boc-L-leucine (45 g, 1.05 eq) and toluene (500 ml) was heated to 50-55° C. and stirred for 30 min at same temperature. The reaction mass was distilled completely under vacuum at less than 55° C. to obtain residue. To the obtained residue dimethyl formamide (250 ml) was charged at 25-30° C. and allowed to cool to 2-6° C. To the reaction mass HOBt (2.4 g, 0.1 eq), PyBOP (107 g, 1.2 eq) and L-phenyl alanine benzyl ester hydrochloride (50 g, 1 eq) and diisopropyl ethyl amine (89 g, 4 eq) were sequentially added at 2-6° C. and stirred for 5 min at same temperature. Then the reaction mass was heated to 25-30° C. and stirred for 2-3 hr at same temperature. After completion of the reaction, reaction mass was quenched in to water (2500 ml) at 25-30° C. and stirred for 3-4 hr at same temperature. Precipitated solid was filtered, washed with water (250 ml) and dried to get the title compound. Yield: 77.5 g; PXRD: FIG. 1; DSC: endothermic peak at about 104° C.; Chemical purity by HPLC: 99.97%; HOBt: Not detected, PyBOP: 0.01% and tris(pyrrolidino phosphine) oxide: Not detected by HPLC.

Example 2: Preparation of Compound of Formula VII

A mixture of methylene chloride (90 ml) and trifluoro acetic acid (210 ml) was allowed to cool to 2-6° C. and compound of Formula IV (100 g, 1 eq) was added at same temperature. Then the reaction mass was heated to 25-30° C. and stirred for 2 hr at same temperature. To the reaction mass methylene chloride (1.5 lit) was added and pH adjusted to 7-8 with 20% sodium carbonate at 25-30° C. and stirred for 20 min at same temperature. Separated the organic layer and washed with water (300 ml) and 10% sodium chloride (300 ml) sequentially. Organic layer was separated and concentrated under vacuum at below 35° C. to obtain residue. The obtained residue was dissolved in dimethyl formamide (500 ml) and allowed to cool to 2-6° C. To the reaction mass HOBt (2.9 g, 0.1 eq), PyBOP (133.5 g, 1.2 eq), N-boc-homo phenyl alanine (59.7 g, 1 eq) were added slowly at 2-6° C. To the reaction mass HOBt (2.9 g, 0.1 eq), PyBOP (133.5 g, 1.2 eq), N-boc-homo phenyl alanine (59.7 g, 1 eq) and diisopropyl ethyl amine (110.5 g, 4 eq) were added slowly at 2-6° C. Then the reaction mass was heated to 25-30° C. and stirred for 2-3 hr at same temperature. After completion of the reaction, reaction mass was quenched in to water (5 lit) at 25-30° C. and stirred for 2-3 hr at same temperature and the precipitated solid was filtered, washed with water (500 ml) and dried to get the title compound. Yield: 130 g; PXRD: FIG. 2; DSC: endothermic peak at about 150° C.; Chemical purity by HPLC: 99.97%; HOBt: 0.1%, PyBOP: Not detected and tris(pyrrolidino phosphine) oxide: 0.02% by HPLC.

Example 3: Preparation of Compound of Formula VIII

A mixture of methanol (150 ml), methylene chloride (150 ml), compound of Formula VII (30 g) and 10% Pd/C (6 g) were charged in to 2 lit auto clave at 25-35° C. and purged hydrogen gas at 25-30° C. for a period of 36 hr. After completion of the reaction, filtered the reaction mass and filterate was distilled under vacuum at below 40° C. To the obtained compound n-heptane (120 ml) was added at 25-35° C. and stirred for 1-2 hr at same temperature. The solid obtained was filtered and dissolved in ethyl acetate (120 ml) at 25-35° C. The obtained solution was added in to n-heptane (450 ml) at 25-35° C. and stirred for 2 hr at same temperature. Precipitated solid was filtered, washed with n-heptane (90 ml) and dried to get the title compound. Yield: 24 g; PXRD: FIG. 3; DSC: endothermic peak at about 64° C.; Chemical purity by HPLC: 97.2%.

Example 4: Preparation of Compound of Formula X

A mixture of methylene chloride (105 ml) and [(1S)-3-Methyl-1-[[(2R)-2-methyloxiranyl] carbonyl]butyl]carbamic acid 1,1-dimethylethyl ester (7.5 g, 1 eq) was allowed to cool to 2-6° C. To the reaction mass trifluoroacetic acid (15 ml) was added at same temperature. Then the reaction mass was heated to 25-30° C. and stirred for 2 hr at same temperature. After completion of reaction, reaction mass was distilled completely under vacuum at below 35° C. and the obtained residue was dissolved in dimethyl formamide (30 ml).

In another reaction flask a mixture of dimethyl formamide (45 ml) and compound of Formula VIII (15 g, 1 eq) was allowed to cool to 2° C. to 6° C. To the reaction mass HOBt (0.4 g, 0.1 eq), PyBOP (23.2 g), dimethyl formamide solution of (2S)-2-Amino-4-methyl-1-[(2R)-2-methyloxiranyl]-1-pentanonetrifluoroacetate (30 ml) and diisopropyl ethyl amine (14.4 g, 4 eq) was slowly added sequentially at 2° C. to 6° C. and stirred for 2-4 hr at same temperature. After completion of the reaction, reaction mass was quenched in to water (750 ml) at 25-30° C. and stirred for 2-3 hr at same temperature. Precipitated solid was filtered and washed with water (75 ml) to obtain crude compound of Formula X.

Figure 4:
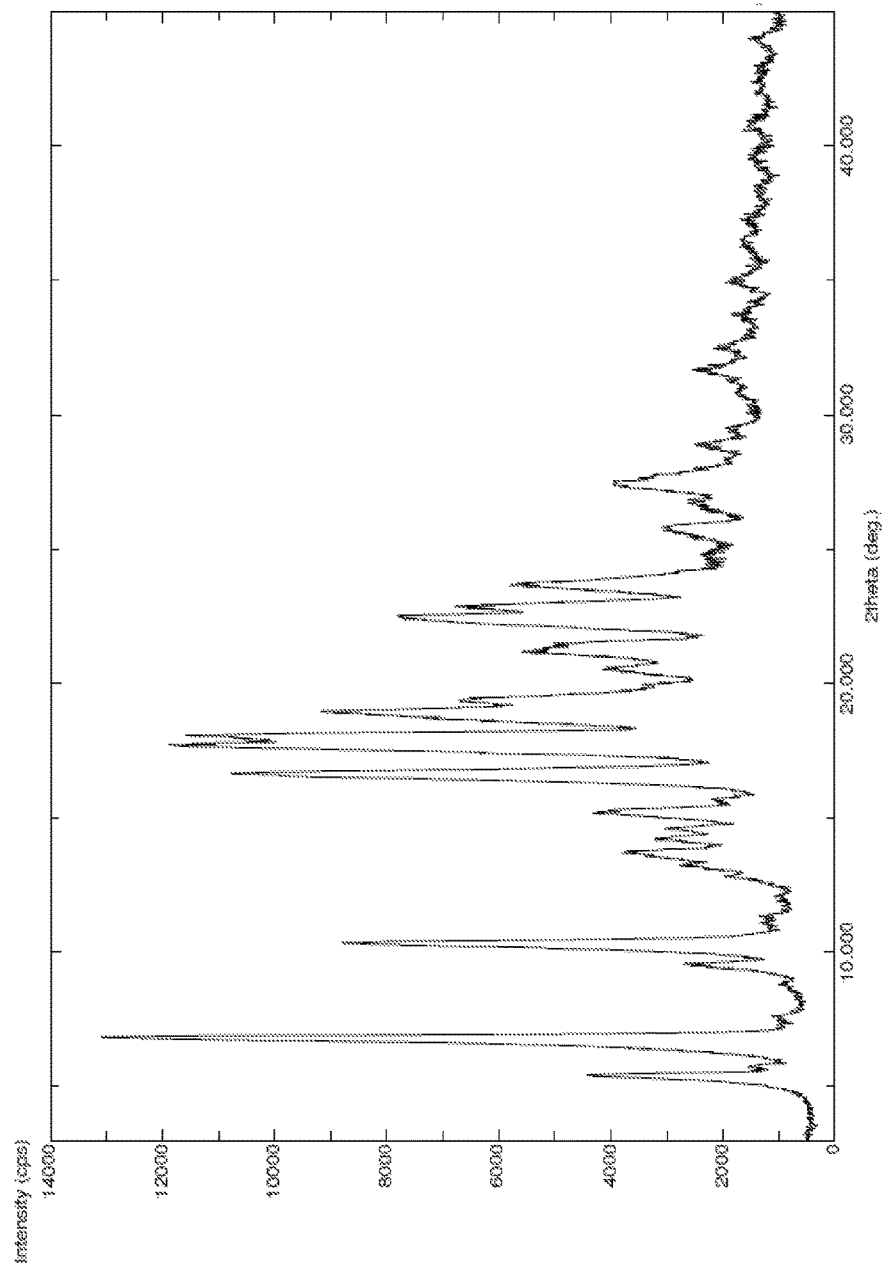
FIG. 4 is the characteristic powder X-ray diffraction (XRD) pattern of a crystalline compound of Formula X.

The obtained crude compound of Formula X was dissolved in ethyl acetate (225 ml) at 25-35° C. and heated to reflux for 30 min. filtered the undissolved material and reaction mass was allowed to cool to 2-6° C. Precipitated solid was filtered, washed with chilled ethyl acetate (30 ml) and dryed to get the title compound. Yield: 14 g; PXRD: FIG. 4; DSC: endothermic peak at about 151.7° C. and exothermic peak at about 164° C.; Chemical purity by HPLC: 97.0%.

Example 5: Preparation of Carfilzomib Maleate Salt

A mixture of methylene chloride (140 ml) and compound of Formula X (14 g, 1 eq) was allowed to cool to 2-6° C. and trifluoroacetic acid (84 ml) was added at same temperature and stirred for 2-3 hr at same temperature. After completion of reaction, reaction mass was distilled completely under vacuum at below 35° C. and the obtained compound was slurred in n-heptane (70 ml) at 25-35° C. Filtered the solids and washed with n-heptane (70 ml) to obtain trifluoro acetic acid salt of Formula XI. PXRD: FIG. 5; DSC: endothermic peak at about 115° C.; or the reaction mass was basified and isolated the compound of Formula XI as its free base. PXRD: FIG. 6; DSC: exothermic peaks at about 76.8° C. and 141.8° C.

A mixture of dimethyl formamide (42 ml) and 2-morpholino acetic acid of Formula XII (3.73 g) was allowed to cool to 2-6° C. To the reaction mass HOBt (0.27 g, 0.1 eq), PyBOP (12.6 g, 1.2 eq), Formula XI free base (dissolved in 28 ml dimethyl formamide) and diisopropyl ethyl amine (10.34 g, 4 eq) were slowly added sequentially at 2° C. to 6° C. and stirred for 2-4 hr at same temperature. After completion of the reaction, reaction mass was quenched in to water (700 ml) at 25-30° C. and stirred for 2-3 hr at same temperature. Precipitated solid was filtered, washed with water (75 ml). The obtained compound was dissolved in ethyl acetate (700 ml), washed with 5% sodium bisulphate (2×140 ml), 5% sodium bicarbonate (2×140 ml) and water (140 ml) sequentially. Organic layer was separated and passed through silicycle-M 60 silica gel bed and compound containing fractions were collected and distilled completely under vacuum at 25-35° C. to obtaine residue. The obtained residue was dissolved in a mixture of acetonitrile (70 ml) and tetrahydrofuran (35 ml) at 25-35° C. and stirred for clear solution. To the reaction mass maleic acid (2.32 g) was added at 25-30° C. and stirred for 30 min at same temperature. To the reaction mass acetonitrile (70 ml) was charged and stirred for 1-2 hr at 25-30° C. Precipitated solid was filtered, washed with acetonitrile (70 ml) and dried. To the obtained compound n-propanol (210 ml) was added and heated to reflux for 30-60 min. Reaction mass was allowed to cool to 25-35° C. Precipitated solid was filtered, washed with chilled n-propanol (28 ml) and dried to get crystalline maleate salt. Yield: 8 g; Chemical purity by HPLC: 99.8%; PXRD: FIG. 7; DSC: Endothermic peak at 185.4° C.; TGA: No weight loss; HOBt: 0.15%, PyBOP: Not detected and tris(pyrrolidino phosphine) oxide: 0.05% by HPLC.

Example 6: Preparation of Compound of Formula XIV

A mixture of methylene chloride (60 ml) and trifluoro acetic acid (240 ml) was allowed to cool to 2-6° C. To the reaction mass compound of Formula VII (100 g, 1 eq) was added at same temperature. Then the reaction mass was heated to 25-30° C. and stirred for 2 hr at same temperature. To the reaction mass methylene chloride (1.5 lit) was added and pH adjusted to 7-8 with 20% sodium carbonate at 25-30° C. and stirred for 20 min at same temperature. Separated the organic layer and washed with water (300 ml) and 10% sodium chloride (300 ml) sequentially. Organic layer was separated and concentrated under vacuum at 25-35° C. to obtain residue. The obtained residue was dissolved in dimethyl formamide (500 ml) and allowed to cool to 2-6° C. To the reaction mass HOBt (2.2 g, 0.1 eq), PyBOP (99.2 g, 1.2 eq), morpholine acetic acid (29.5 g, 1.2 eq) and diisopropyl ethyl amine (82.1 g, 4 eq) were slowly added sequentially at 2-6° C. Then the reaction mass was heated to 25-30° C. and stirred for 2-3 hr at same temperature. After completion of the reaction, reaction mass was quenched in to water (5 lit) at 25-30° C. and stirred for 2 hr at same temperature and the solid precipitated was filtered, washed with water (500 ml) and dried to get the title compound. Yield: 94 g; Chemical purity by HPLC: 97.6%; HOBt: 0.35%, PyBOP: 0.01% and tris(pyrrolidino phosphine) oxide: 0.04% by HPLC.

Example 7: Preparation of Compound of Formula XV

Compound of Formula XIV (100 g) was dissolved in methanol (4.5 lit) at 25-30° C. To the reaction mass ammonium formate (38.5 g dissolved in 500 ml methanol) and palladium on carbon (20 g) were added and stirred for 2 hr at same temperature. After completion of the reaction, filtered the reaction mass and filterate was distilled under vacuum at below 45° C. to obtain residue. To the obtained residue water (1 lit) was added at 25-30° C. and stirred for 2-3 hr at same temperature. The solid was filtered, washed with acetone (500 ml) and dried. To the obtained solid n-propanol (3 lit) was added and heated to reflux for 1 hr. Then the reaction mass was allowed to cool to 25-30° C. and stirred for 2-4 hr at same temperature. Precipitated solid was filtered, washed with n-propanol (200 ml) and dried to get the title compound. Yield: 77 g; Chemical purity by HPLC: 99.7%.

Example 8: Preparation of Carfilzomib Maleate Salt

A mixture of methylene chloride (250 ml) and [(1S)-3-Methyl-1-[[(2R)-2-methyloxiranyl]carbonyl]butyl]carbamic acid 1,1-dimethylethyl ester (50 g, 1 eq) was allowed to cool to 2-6° C. To the reaction mass trifluoroacetic acid (100 ml) was added at same temperature. Then the reaction mass was heated to 25-30° C. and stirred for 2 hr at same temperature. After completion of reaction, reaction mass was distilled completely under vacuum at below 35° C. and the obtained residue was dissolved in acetonitrile (500 ml).

In another reaction flask a mixture of acetonitrile (4500 ml) and compound of Formula XV (100 g, 1 eq) was allowed to cool to −10° C. to −5° C. To the reaction mass HOBt (38.1 g, 0.1 eq), PyBOP (146.8 g, 1.2 eq), acetonitrile solution of (2S)-2-Amino-4-methyl-1-[(2R)-2-methyloxiranyl]-1-pentanonetrifluoroacetate (500 ml) and diisopropyl ethyl amine (91.2 ml, 4 eq) were added sequentially at −10° C. to −5° C. and stirred for 3-4 hr at same temperature. After completion of the reaction, reaction mass was distilled completely under vacuum at below 35° C. to obtain residue and the obtained residue was dissolved in ethyl acetate and washed the clear solution with 5% sodium bicarbonate (3×100 ml), water (1 lit), 5% sodium chloride (1 lit) sequentially. Organic layer was separated and passed through silica gel bed and the product containing fractions were collected and distilled completely under vacuum at below 35° C. to obtain residue. The obtained residue was dissolved in a mixture of acetonitrile (250 ml) and tetrahydrofuran (250 ml) at 25-30° C. To the reaction mass maleic acid (20.5 g) was added at 25-30° C. and stirred for 30 min at same temperature. To the reaction mass acetonitrile (500 ml) was charged and stirred for 1-2 hr at 25-30° C. The solid obtained was filtered, washed with acetonitrile (1.5 lit) and dried. To the obtained compound n-propanol (1 lit) was added and heated to reflux for 10 min. Then the reaction mass was allowed to cool to 2-6° C. Precipitated solid was filtered, washed with chilled n-propanol (1 lit) and dried to get the title compound. Yield: 100 g; PXRD: FIG. 7; Chemical purity by HPLC: 99.8%; HOBt: 0.15%, PyBOP: Not detected and tris(pyrrolidino phosphine) oxide: 0.05% by HPLC.

Example 9: Preparation of Amorphous Form of Carfilzomib

A mixture of methylene chloride (180 ml) and carfilzomib maleate salt (6 g) was allowed to cool to 2-6° C. To the reaction mass sodium bicarbonate solution (1.27 g dissolved in 60 ml water) was added slowly at 2-6° C. and stirred for 10 min at same temperature. Organic layer was separated and washed with sodium bisulphate (2×60 ml) and water (2×60 ml) sequentially. Organic layer was separated and distilled under vacuum completely to obtain residue. The obtained residue was dissolved in a mixture of ethyl acetate (90 ml) and methylene chloride (12 ml) and passed the solution through neutral silica bed and separated the product containing fractions and distilled completely under vacuum at below 40° C. to obtain residue. The obtained residue was dissolved in methanol (42 ml) at 25-30° C. Then the methanol solution was slowly added in to pre cooled water (420 ml) at 4-10° C. and stirred for 1 hr at same temperature. Precipitated solid was filtered, washed with water (60 ml) and dried to get the title compound. Yield: 2.4 g; Chemical purity by HPLC: 99.8%; HOBt: Not detected, PyBOP: Not detected, tris(pyrrolidino phosphine) oxide: Not detected, Formula 28: 0.02%, Formula 29 to Formula 36: Not detected, Formula 37: 0.02%, Formula 38: Not detected, Formula 39: Not detected, Formula 40: 0.02% and Formula 41: Not detected by HPLC.

Example 10: Preparation of tert-butyl ((2S)-1-(methoxy (methyl) amino)-4-methyl-1-oxopentane-2-yl) carbamate of Formula XVII A mixture of N-Boc-L-Leucine monohydrate (216 g) and toluene (2 lit) was heated to 45-50° C. and was distilled completely under vacuum at same temperature to obtain a residue. To the obtained residue methylene chloride (1 lit) was added at 25-30° C. and allowed to cool to −10° C. to −5° C. To the reaction mass PyBOP (584 g), HOBt (128 g), N,O-dimethyl hydroxyl amine hydrochloride (168 g) and diisopropylethylamine (690 ml) were added and allowed to stir at same temperature. After completion of the reaction, reaction mass was washed with 8% sodium bicarbonate solution (2 lit), water (2 lit), 10% sodium chloride solution (2 lit) sequentially. Organic layer was separated and distilled under vacuum completely and followed by co-distilled with cyclohexane (500 ml) to obtain residue. To the obtained residue cyclohexane (2 lit) was added and stirred for 30 min at 25-30° C. Filtered the reaction mass and the filtrate was concentrated under vacuum to obtain a residue. The obtained residue was dissolved in cyclohexane (1 lit) and passed through neutral alumina column. Concentrated the product containing column fractions completely under vacuum to obtain residue and the obtained residue was dissolve in n-hexane (100 ml) at 25-30° C. and allowed to cool to −15 to −10° C. and stirred for 2 hr at same temperature. Filtered the un-wanted solids and concentrated the filterate under vacuum at 45-50° C. to obtain title compound. Yield: 210 g Example 11: Preparation of tert-butyl ((4S)-2,6-dimethyl-3-oxo hept-1-en-4-yl))carbamate of Formula XVIII A mixture of compound of Formula XVII (100 g) and toluene (1500 ml) was heated to 75-80° C. and was distilled completely under vacuum at same temperature to obtain residue. The obtained residue was dissolved in tetrahydrofuran (100 ml) at 25-30° C. In another reaction flask isopropenyl magnesium bromide (2.19 lit) was charged at 25-30° C. and slowly added the above tetrahydrofuran solution over 2 hr at 25-40° C. and stirred for 45 min at same temperature. After completion of the reaction, quenched the reaction mass in to 15% ammonium chloride (1.5 lit) at 0-5° C. and organic layer was separated and concentrated under vacuum at below 40° C. to obtain residue. The obtained residue was purified by silicycle silica by using ethyl acetate and cyclohexane solvent system. Product containing solvent fractions were combined and concentrated under vacuum at below 40° C. to obtain residue. The obtained residue was dissolved in acetone (100 ml) at 25-30° C. and allowed to cool to −5 to 0° C. To the clear solution water (1.5 lit) was added slowly at −5 to 0° C. Precipitated solid was filtered, washed with water (100 ml) and dried to get the title compound as a crystalline solid. Yield: 72 g; PXRD: FIG. 9; Chemical purity by HPCL: 99.44%; Chiral purity by HPLC: 99.73%.

Example 12: Preparation of tert-butyl N-[(3R/S, 4S)-3-hydroxy-2,6-dimethylhept-1-en-4-yl]carbamate of Formula XIX A mixture of compound of Formula XVIII (115 g) and methanol (500 ml) was allowed to cool to 0-5° C. To the reaction mass cerium (III) chloride heptahydrate solution (203 g dissolved in 500 ml methanol) was added slowly at 0-5° C. Then the reaction mass was allowed to cool −5 to 0° C. and sodium borohydride (10.2 g) was added in lot wise over 1 hr at same temperature. After completion of the reaction, acetic acid (20 ml) was added drop wise at same temperature and concentrated reaction mass under vacuum at below 40° C. to obtain a solid. The obtained solid was dissolved in ethyl acetate (1 lit) and washed with water (500 ml) and 10% sodium chloride solution (500 ml) sequentially. Organic layer was separated and concentrated under vacuum at below 40° C. to obtain title compound as a solid. The obtained solid was dissolved in methanol (100 ml) at 25-30° C. and allowed to cool to 0-5° C. To the reaction mass water (150 ml) was added at 0-5° C. Precipitated solid was filtered, washed with water (100 ml) and dried to get the title compound as a crystalline solid. Yield: 95 g; PXRD: FIG. 10; Chemical purity by HPLC: 99.48%, Chiral purity by HPLC: 99.99%.

Example 13: Preparation of tert-butyl N-[(1R/S, 2S)-1-((2R/S)-2-methyloxirane-2-yl)-1-hydroxy-4-methylpentan-2-yl]carbamate of Formula XX A mixture of compound of Formula XIX (20 g) and methylene chloride (200 ml) was allowed to cool to 0-5° C. To the reaction mass mCPBA (22.6 g) was added in lot wise at 0-5° C. and heated to 25-30° C. After completion of the reaction, reaction mass was allowed to cool to 0-5° C. and solid was filtered. Then the product containing filterate was

Example 14: Preparation of tert-butyl ((2S)-4-methyl-1-((2R)-2-methyloxirane-2-yl)-1-oxo pentan-2-yl) carbamate of Formula XVI Compound of Formula XX (16 g) was dissolved in acetonitrile (80 ml) at 25-30° C. To the reaction mass a mixture of acetonitrile (80 ml) and Dess-Martin Periodinane (37.3 g) were added over a period of 1 hr at 0-5° C. Then the reaction mass was heated to 25-30° C. and stirred for 2 hr at same temperature. After completion of the reaction, reaction mass was quenched in to 8% sodium bicarbonate solution (160 ml) at 0-5° C. and extracted with ethyl acetate. Ethyl acetate layer was concentrated under vacuum at below 40° C. to obtain oily mass. The obtained oily mass was purified by column chromatography using a mixture of 0.5% ethyl acetate and cyclohexane as an eluent. Then the product containing solvent fractions were combined and concentrated under vacuum at below 40° C. to obtain title compound as residue. Chemical purity by HPLC: 99.0%; Compound of Formula XVIII by HPLC: 0.5%.

The obtained residue was dissolved in n-heptane (4 ml) at 25-30° C. and stirred for 10 min at same temperature. Reaction mass was allowed to cool to −5 to 0° C. and stirred for 30 min at same temperature, to the reaction mass seed compound of Formula XVI (16 mg) was added at same temperature. Precipitated solid was filtered and dried to get the title compound as a crystalline solid. Yield: 4.5 g; PXRD: FIG. 8; Chemical purity by HPLC: 99.88%, Compound of Formula XVIII by HPLC: 0.05%, Chiral purity by HPLC: 100%.

Comparative Example 1: Preparation of Compound of Formula IV

A mixture of acetonitrile (900 ml), N-boc-L-leucine (19.8 g, 1 eq), L-phenyl alanine benzyl ester hydrochloride (25 g, 1 eq) and diisopropyl ethyl amine (44.2 g, 4 eq) were charged in to a reaction flask at 25-30° C. and stirred for 10 min at same temperature. Then the reaction mass was allowed to cool to 0° C. and HOBt (18.5 g, 1.6 eq), PyBOP (71.3 g, 1.6 eq) were added in lot wise over 5 min at same temperature and stirred under nitrogen for overnight at same temperature. After completion of reaction, reaction mass was distilled completely under vacuum and the obtained crude was dissolved in ethyl acetate (500 ml), washed with saturated sodium bicarbonate solution, water followed by sodium chloride solution. Organic layer was dryed with magnesium sulphate and distilled under vacuum to obtain title compound. Yield: 25 g; Chemical purity by HPLC: 88.12%; HOBt: 4.1%, PyBOP: Not detected and tris(pyrrolidino phosphine) oxide: 5.41% by HPLC.

Comparative Example 2: Preparation of Compound of Formula VII

A mixture of 70% trifluoro acetic acid/methylene chloride (150 ml) was allowed to cool to 0° C. To the reaction mass compound of Formula IV (25 g, 1 eq) was added at same temperature. Then the reaction mass was heated to 25-30° C. and stirred for 2 hr at same temperature. After completion of reaction, distilled the reaction mass completely under vacuum and the obtained trifluoroacetic acid salt of Formula V was dissolved in acetonitrile (550 ml). To the reaction mass N-boc-homo phenyl alanine (25 g, 1 eq) and diisopropyl ethyl amine (27.5 g, 4 eq) were added at 25-30° C. Reaction mass was allowed to cool to 0° C. and HOBt (11.5 g, 1.6 eq), PyBOP (44.4 g, 1.6 eq) were added in lot wise over 5 min at same temperature and stirred for overnight under nitrogen at 25-30° C. Then the reaction mass was allowed to cool to 0° C. and the solid obtained was filtered, washed with chilled acetonitrile to get the title compound. Yield: 24.8 g; Chemical purity by HPLC: 89.35%; HOBt: 9.9%, PyBOP: 0.02% and tris(pyrrolidino phosphine) oxide: 0.24% by HPLC.

Comparative Example 3: Preparation of Compound of Formula XIV

A mixture of 80% trifluoro acetic acid/methylene chloride (12 ml) and compound of Formula VII (0.25 g, 1 eq) were combined in a reaction flask at 25-30° C. and stirred for 1 hr at same temperature. After completion of reaction, reaction mass was distilled completely under vacuum and the obtained oily trifluoroacetic acid salt of Formula VIII was dissolved in dimethyl formamide (6 ml). To the reaction mass morpholine acetic acid (0.07 gm) and diisopropyl ethyl amine (0.5 g, 10 eq) were added at 25-30° C. Then reaction mass was allowed to cool to 0° C. and PyBOP (0.3 g, 1.6 eq) was added in lot wise for 5 min at same temperature. Reaction mass was heated to 25-30° C. and stirred for overnight under nitrogen. After completion of reaction, reaction mass was diluted with brine solution and extracted with ethyl acetate and washed with saturated sodium bicarbonate solution, water followed by sodium chloride solution. Organic layer was separated and distilled under vacuum to obtain title compound. Yield: 0.19 g; Chemical purity by HPLC: 92.14%; HOBt: 2.03%, PyBOP: 0.24% and tris(pyrrolidino phosphine) oxide: 3.4% by HPLC.

Comparative Example 4: Preparation of Compound of Formula XV

Compound of Formula XIV (0.19 g) was dissolved in 1:1 mixture of methanol and ethyl acetate (5 ml) at 25-30° C. To the reaction mass 10% Pd/C (0.05 g) was added and stirred under hydrogen atmosphere for 2 hr at same temperature. After completion of reaction, filtered the reaction mass through hyflo bed and filterate was distilled under vacuum to obtain title compound. Yield: 0.12 g; Chemical purity by HPLC: 95.90%; HOBt: 0.41% and tris(pyrrolidino phosphine) oxide: 1.42% by HPLC.

Comparative Example 5: Preparation of Carfilzomib

Trifluoroacetic acid salt of Formula IX (0.08 g), acetonitrile (5 ml), compound of Formula XV (01 g, 1 eq), diisopropyl ethyl amine (0.3 g) and HOBt (0.04 g, 1.6 eq) were combined in a reaction flask at 25-30° C. Reaction mass was allowed to cool to 0° C. and PyBOP (0.15 g, 1.6 eq) was added lot wise in 5 min at same temperature. Then the reaction mass was stirred for overnight under nitrogen at 5° C. After completion of reaction, reaction mass was diluted with brine solution and extracted with ethyl acetate and the organic layer was washed with saturated sodium bicarbonate solution, water followed by sodium chloride solution. Organic layer was separated and distilled under vacuum and the obtained crude compound was dissolved in methanol and slowly added in to water (100 ml) under rapid stirring at 0° C. Precipitated solid was filtered to get the title compound. Yield: 0.08 g; Chemical purity by HPLC: 25.91%; HOBt: 59.34%, PyBOP: 2.04% and tris(pyrrolidino phosphine) oxide: 1.7% by HPLC.

It will be understood that various modifications may be made to the embodiments disclosed herein. Therefore the above description should not be constructed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. An improved process for the preparation of carfilzomib of Formula I or a pharmaceutically acceptable salt thereof, Formula I

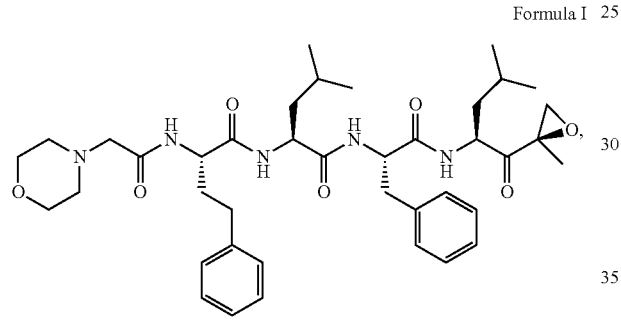

comprising:

a) reacting a compound of Formula II with a compound of Formula III or a salt thereof in the presence of a coupling agent (C1), an additive (A1) and a base (B1) in a solvent (S1) to obtain a compound of Formula IV, Formula II

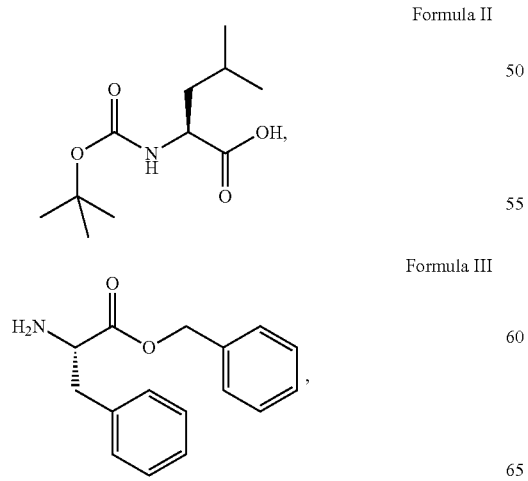

Formula III

Formula IV

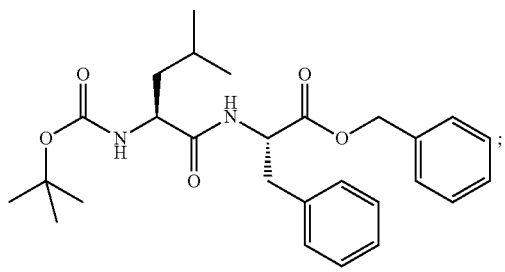

b) reacting the compound of Formula IV with a suitable acid to obtain a compound of Formula V or a salt thereof, Formula V

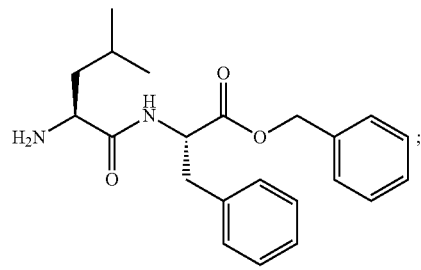

c) reacting the compound of Formula V or a salt thereof with a compound of Formula VI in presence of a coupling agent (C2), an additive (A2) and a base (B2) in a solvent (S2) to obtain a compound of Formula VII, Formula VI

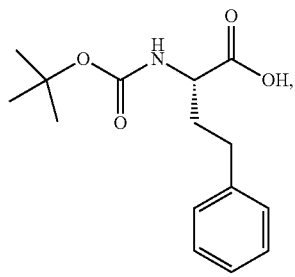

Formula VII

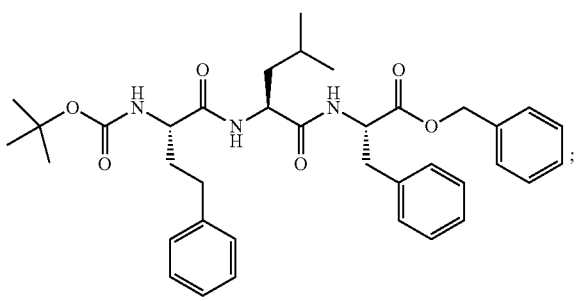

d) deprotecting the compound of Formula VII in presence of a deprotecting agent to obtain a compound of Formula VIII, Formula VIII

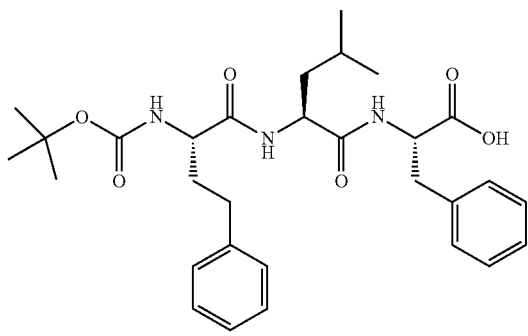

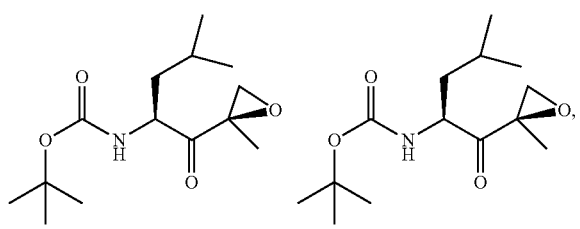

e) reacting the compound of Formula VIII with a compound of Formula IX or a salt thereof in the presence of a coupling agent (C3), an additive (A3) and a base (B3) in a solvent (S3) to obtain a compound of Formula X, Formula IX

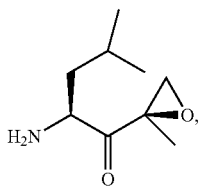

Formula X

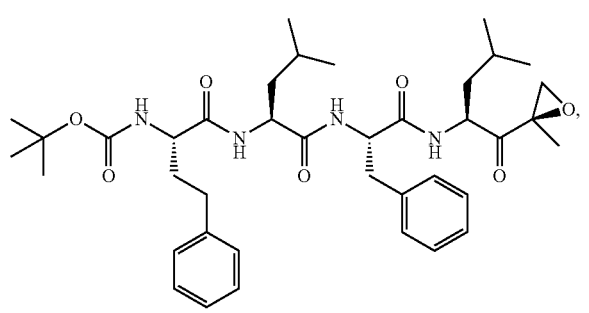

f) reacting the compound of Formula X with a acid to obtain a compound of Formula XI or a salt thereof, Formula XI

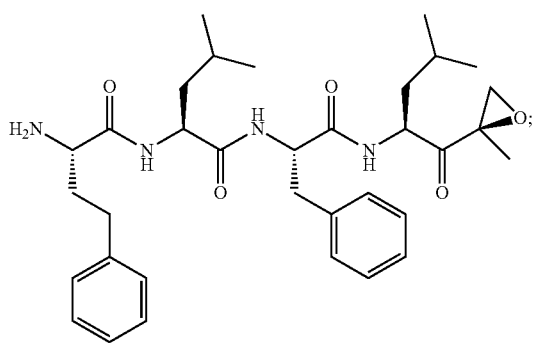

and g) reacting the compound of Formula XI or a salt thereof with a compound of Formula XII or a salt thereof in presence of a coupling agent (C4), an additive (A4) and a base (B4) in a suitable solvent (S4) to obtain carfilzomib or a pharmaceutically acceptable salt thereof, Formula XII

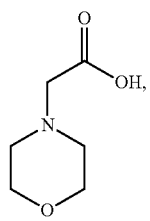

wherein the amount of the coupling agent (C1), (C2), (C3) and (C4) used is about 0.9 to about 1.3 w/w mole equivalents per mole of Formula III, Formula IV, Formula VIII and Formula X respectively and wherein the amount of the additive (A1), (A2), (A3) and (A4) used is about 0.05 to about 0.5 w/w mole equivalents per mole of Formula III, Formula IV, Formula VIII and Formula X respectively.

2. The process of claim 1, wherein the amount of D-isomers and isoleucine compounds corresponding to each of the compounds of Formula II, Formula III, Formula VI and Formula IX is less than 0.1% measured by HPLC.

3. The process of claim 2, wherein the compound of Formula II includes less than 0.1% measured by HPLC of its corresponding D-isomer and isoleucine of Formula A and Formula B, Formula A

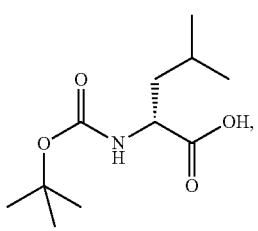

Formula B

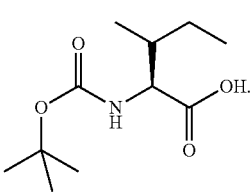

4. The process of claim 2, wherein the compound of Formula III includes less than 0.1% measured by HPLC of its corresponding D-isomer of Formula C, Formula C

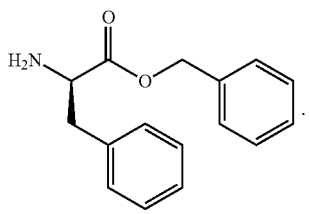

5. The process of claim 1, wherein each of the coupling agents (C1), (C2), (C3) and (C4) is selected from the group consisting of benzotriazol-1-yl-oxytripyrrolidinophosphonium hexafluorophosphate, benzotriazol-1-yloxy-tris (dimethylamino)-phosphonium hexafluorophosphate, bromo-tripyrrolidino-phosphonium hexafluorophosphate, Propylphosphonic anhydride, N-(3-dimethylaminopropyl)-N'-ethylcarbodiimide, 1,1'-Carbonyldiimidazole, diisopropylcarbodiimide, dicyclohexyl carbodiimide, and mixtures thereof.

6. The process of claim 1, wherein each of the additives (A1), (A2), (A3) and (A4) is selected from the group consisting of 1-Hydroxybenzotriazole, 1-Hydroxy-7-aza-1H-benzotriazole, 2-(1H-Benzotriazol-1-yl)-N,N,N',N'-tetramethylaminium tetrafluoroborate/hexafluoro phosphate, 2-(7-Aza-1H-benzotriazol-1-yl)-N,N,N',N'-tetramethylaminium hexafluorophosphate), and mixture thereof.

7. The process of claim 1, wherein each of the bases (B1), (B2), (B3) and (B4) is is selected from the group consisting of diisopropylethyl amine, Imidazole or its salts, 1,8-Diazabicyclo[5.4.0]undec-7-en, tertiary amines or its hydro halide salts thereof.

8. The process of claim 1, wherein each of the solvents (S1), (S2), (S3) and (S4) is selected from the group consisting of ethers selected from one of tetrahydrofuran and 2-methyltetrahydrofuran; esters selected from one of methyl acetate, ethyl acetate, propyl acetate, and butyl acetate; halogenated hydrocarbons selected from one of methylene chloride, ethylene chloride and chloroform; amides selected from one of dimethyl formamide, dimethyl acetamide and N-methyl pyrrolidinone; aromatic solvents selected from one of toluene, xylene, and chlorobenzene; nitriles selected from one of acetonitrile, propionitrile and benzonitrile; and mixtures thereof.

9. The process of claim 1, wherein the step a) is carried out using about 1.2 w/w mole equivalents of benzotriazol-1-yl-oxytripyrrolidinophosphonium hexafluorophosphate per mole of Formula III as coupling agent (C1), about 0.1 w/w mole equivalents of 1-hydroxybenzotriazole per mole of Formula III as an additive (A1) in presence of diisopropylethyl amine as base in dimethyl formamide.

10. The process of claim 1, wherein the acid of step b) is selected from the group consisting of hydrochloric acid, hydrobromic acid, sulfuric acid, phosphoric acid, acetic acid, trifluoro acetic acid, trichloro acetic acid, methane sulfonic acid, and mixture thereof.

11. The process of claim 1, wherein the step b) is carried out in an organic solvent selected from the group consisting of methanol, ethanol, isopropanol, acetone, methyl isobutyl ketone, methyl ethyl ketone, tetrahydrofuran, dimethyl ether, diisopropyl ether, methyl tertiary butyl ether, 1,4-dioxane, methylene chloride, ethylene chloride, and mixture thereof.

12. The process of claim 1, wherein the step b) is carried out using trifluoro acetic acid in methylene chloride.

13. The process of claim 2, wherein the compound of Formula VI includes less than 0.1% measured by HPLC of its corresponding D-isomer Formula D, Formula D

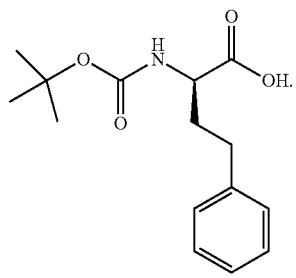

14. The process of claim 1, wherein the step c) is carried out using about 1.2 w/w mole equivalents of benzotriazol-1-yl-oxytripyrrolidinophosphonium hexafluorophosphate per mole of Formula IV as coupling agent (C2), about 0.1 w/w mole equivalents of 1-hydroxybenzotriazole per mole of Formula IV as an additive (A2) in presence of diisopropylethyl amine as base in dimethyl formamide.

15. The process of claim 1, wherein the deprotecting agent is selected from the group consisting of palladium on carbon/ammonium formate, palladium on carbon/ammonium acetate, palladium on carbon/hydrogen gas, palladium hydroxide/hydrogen gas, raney nickel/hydrogen gas, platinum oxide/hydrogen gas and zinc/hydrogen gas.

16. The process of claim 1, wherein the step d) is carried out in a solvent selected from the group consisting of methanol, ethanol, isopropanol, methyl acetate, ethyl acetate, propyl acetate, butyl acetate, tetrahydrofuran, methylene chloride, ethylene chloride, water, and mixture thereof.

17. The process of claim 1, wherein the step d) is carried out with palladium on carbon/hydrogen gas in a solvent mixture of methanol and methylene chloride.

18. The process of claim 2, wherein the compound of Formula IX includes less than 0.1% measured by HPLC of any one or more of the isomers of Formula E, Formula F, Formula G, Formula H, Formula I and Formula J, Formula E

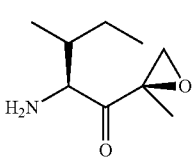

Formula F

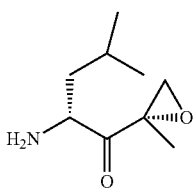

Formula G

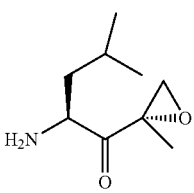

Formula H

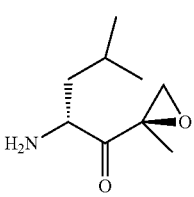

Formula I

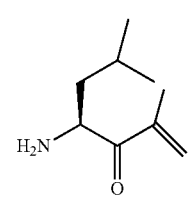

Formula J

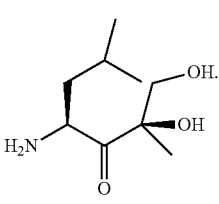

19. The process of claim 1, wherein the step e) is carried out using about 1.2 w/w mole equivalents of benzotriazol-1-yl-oxytripyrrolidinophosphonium hexafluorophosphate per mole of Formula VIII as coupling agent (C3), about 0.1 w/w mole equivalents of 1-hydroxybenzotriazole per mole of Formula VIII as an additive (A3) in presence of diisopropylethyl amine as base in dimethyl formamide.

20. The process of claim 1, wherein the acid of step f) is selected from the group consisting of hydrochloric acid, hydrobromic acid, sulfuric acid, phosphoric acid, acetic acid, trifluoro acetic acid, trichloro acetic acid, methane sulfonic acid, and mixture thereof.

21. The process of claim 1, wherein the step f) is carried out in an organic solvent selected from the group consisting of methanol, ethanol, isopropanol, acetone, methyl isobutyl ketone, methyl ethyl ketone, tetrahydrofuran, dimethyl ether, diisopropyl ether, methyl tertiary butyl ether, 1,4-dioxane, methylene chloride, ethylene chloride, and mixture thereof.

22. The process of claim 1, wherein the step f) is carried out using trifluoro acetic acid in methylene chloride.

23. The process of claim 1, wherein the step g) is carried out using about 1.2 w/w mole equivalents of benzotriazol-1-yl-oxytripyrrolidinophosphonium hexafluorophosphate per mole of Formula X as coupling agent (C4), about 0.1 w/w mole equivalents of 1-hydroxybenzotriazole per mole of Formula X as an additive (A4) in presence of diisopropylethyl amine as base in dimethyl formamide.

24. The process of claim 1, wherein the step e) further comprises:
   a) dissolving the compound of Formula X in one or more solvents at a temperature of about 30° C. to about reflux temperature;
   b) cooling the obtained solution to less than 10° C.; and
   c) filtering the cooled solution to recover the compound of Formula X.

25. The process of claim 24, wherein the one or more solvents is selected from the group consisting of methanol, ethanol, isopropanol, n-propanol, t-butanol, methyl acetate, ethyl acetate, isopropyl acetate, tetrahydrofuran, 2-methyltetrahydrofuran, acetonitrile, propionitrile, acetone, methyl ethyl ketone, methyl isobutyl ketone, methylene chloride, and mixtures thereof.

26. The process of claim 24, wherein the step of dissolving the compound of Formula X in one or more solvents is done at a temperature of about 50° C. to about 80° C.

27. The process of claim 24, wherein the recovered compound of Formula X includes less than 0.1% measured by HPLC of any one or more of a compound of Formula 20, Formula 21, Formula 22, Formula 23, Formula 24, Formula 25, Formula 26, and Formula 27.

28. A compound of Formula X having less than 0.1% measured by HPLC of any one or more of a compound of Formula 20, Formula 21, Formula 22, Formula 23, Formula 24, Formula 25, Formula 26, and Formula 27.

29. The process of claim 1, further comprising:
   h) isolating the carfilzomib as its pharmaceutically acceptable salt thereof as an intermediate; and
   g) converting the salt of carfilzomib to obtain carfilzomib.

30. The process of claim 29, wherein the salt of carfilzomib is carfilzomib maleate.

31. The process according to claim 1, further comprising:
   h) forming a pharmaceutical composition comprising the carfilzomib or the pharmaceutically acceptable salt thereof and at least one pharmaceutically acceptable excipient.

* * * * *